(12) United States Patent
Burton

(10) Patent No.: US 12,193,834 B2
(45) Date of Patent: Jan. 14, 2025

(54) ANAESTHESIA AND CONSCIOUSNESS DEPTH MONITORING SYSTEM

(71) Applicant: David Burton, Camberwell (AU)

(72) Inventor: David Burton, Camberwell (AU)

(*) Notice: Subject to any disclaimer, the term of this patent is extended or adjusted under 35 U.S.C. 154(b) by 216 days.

(21) Appl. No.: 16/806,107

(22) Filed: Mar. 2, 2020

(65) Prior Publication Data

US 2020/0268313 A1 Aug. 27, 2020

Related U.S. Application Data

(63) Continuation of application No. 13/499,895, filed as application No. PCT/AU2010/001050 on Aug. 13, 2010, now Pat. No. 10,595,772.

(30) Foreign Application Priority Data

Aug. 14, 2009 (AU) ................................ 2009903805

(51) Int. Cl.
*A61B 5/021* (2006.01)
*A61B 5/00* (2006.01)
(Continued)

(52) U.S. Cl.
CPC ........ *A61B 5/4821* (2013.01); *A61B 5/02116* (2013.01); *A61B 5/02125* (2013.01);
(Continued)

(58) Field of Classification Search
CPC ... A61B 5/4821; A61B 5/7203; A61B 5/7275; A61B 5/0205; G01R 29/26
See application file for complete search history.

(56) References Cited

U.S. PATENT DOCUMENTS

| 4,195,626 A | 4/1980 | Schweizer |
| 5,140,423 A * | 8/1992 | Lee .................. H04N 5/208 |
| | | 348/625 |

(Continued)

FOREIGN PATENT DOCUMENTS

| CN | 1567331 A * | 1/2005 | |
| EP | 1495715 A1 * | 1/2005 | ........... A61B 5/1106 |

(Continued)

OTHER PUBLICATIONS

Machine translation of CN1567331A (Year: 2005).*

(Continued)

*Primary Examiner* — Alexander Satanovsky
*Assistant Examiner* — Sangkyung Lee
(74) *Attorney, Agent, or Firm* — Morgan, Lewis & Bockius LLP

(57) ABSTRACT

Methods and systems incorporating non-linear dynamic (NLD) analysis such as entropy or other complexity analysis monitoring continuous or evoked signals from a biological subject are presented, where such a system comprises of processing steps including: a) the combination of a biological signal evoked as a result of patient stimulation presented to a biological subject and a non-linear analysis method capable of capturing temporal changes in signal order or regularity; b) any combination of processed evoked or continuous central nervous or peripheral physiological mechanisms b) a means to generate a measure indicative of a patient's level of anaesthesia and consciousness depth (A&CD), sedation or sleep/wake state. Methods and systems incorporating a NLD analysis means to improve the discrimination between different signals origins including any combination of: a) central nervous system (CNS), b) peripheral control or nervous system (PNS), c) autonomic control or nervous system (ANS), d) arousals, and e) artifacts.

18 Claims, 32 Drawing Sheets

(51) Int. Cl.
*A61B 5/0205* (2006.01)
*A61B 5/024* (2006.01)
*A61B 5/08* (2006.01)
*A61B 5/145* (2006.01)
*A61B 5/325* (2021.01)
*G01R 29/26* (2006.01)
*G16H 50/30* (2018.01)

(52) U.S. Cl.
CPC .......... *A61B 5/02405* (2013.01); *A61B 5/325* (2021.01); *A61B 5/4029* (2013.01); *A61B 5/4064* (2013.01); *A61B 5/415* (2013.01); *A61B 5/4839* (2013.01); *A61B 5/7203* (2013.01); *A61B 5/721* (2013.01); *A61B 5/7275* (2013.01); *G01R 29/26* (2013.01); *A61B 5/0205* (2013.01); *A61B 5/08* (2013.01); *A61B 5/14542* (2013.01); *A61B 5/4047* (2013.01); *A61B 5/4088* (2013.01); *A61B 5/7207* (2013.01); *A61B 5/7257* (2013.01); *A61B 5/7285* (2013.01); *G16H 50/30* (2018.01)

(56) References Cited

U.S. PATENT DOCUMENTS

| | | |
|---|---|---|
| 6,016,444 A | 1/2000 | John |
| 6,272,652 B1 * | 8/2001 | Starr .................. H03M 13/353 714/701 |
| 7,190,292 B2 * | 3/2007 | Bizjak ................... H03G 7/002 341/110 |
| 2002/0173729 A1 | 11/2002 | Viertio-Oja et al. |
| 2002/0183605 A1 | 12/2002 | Devlin et al. |
| 2004/0015158 A1 * | 1/2004 | Chen .................. A61B 5/02007 606/11 |
| 2004/0138578 A1 * | 7/2004 | Pineda .................... A61N 2/006 600/544 |
| 2004/0193068 A1 | 9/2004 | Burton et al. |
| 2004/0243017 A1 | 12/2004 | Causevic |
| 2006/0084881 A1 * | 4/2006 | Korzinov ............... A61B 5/366 600/509 |
| 2006/0217628 A1 | 9/2006 | Huiku |
| 2007/0112277 A1 * | 5/2007 | Fischer ................ A61B 5/6817 600/544 |
| 2007/0179552 A1 | 8/2007 | Dennis et al. |
| 2007/0185947 A1 * | 8/2007 | Yoshitake ............. H03B 29/00 708/271 |
| 2009/0076339 A1 | 3/2009 | Quintin et al. |
| 2009/0099474 A1 * | 4/2009 | Pineda .................. A61B 5/386 600/545 |

FOREIGN PATENT DOCUMENTS

| | | | |
|---|---|---|---|
| JP | 2000325330 A | * 11/2000 | |
| JP | 2005334424 A | * 12/2005 | |
| WO | WO-2006049194 A1 * | 5/2006 | .......... A61B 5/0059 |
| WO | WO-2007058950 A2 * | 5/2007 | .......... A61B 5/0017 |
| WO | 2008/077242 A1 | 7/2008 | |
| WO | 2009/033181 A1 | 3/2009 | |

OTHER PUBLICATIONS

Machine translation of JP2000325330 (Year: 2000).*
Machine translation of JP2005334424A (Year: 2005).*
Machine translation of WO2006049194A1 (Year: 2006).*

* cited by examiner

STRUCTURED APPROACH TO EFFECTIVE SEDATION, PAIN AND ANAESTHESIA (SPA)
MONITORING - CONTEMPORARY APPROACH

STRUCTURED APPROACH TO EFFECTIVE SEDATION, PAIN AND ANAESTHESIA (SPA) MONITORING (CONTEMPORARY APPROACH) DEMONSTRATING MONITORING KEY OUTCOMES (GOALS), CAUSAL MECHANISMS, TOGETHER WITH CORRESPONDING UNDERLYING MEASUREMENT MARKERS AS THEY RELATE TO BOTH DISCRETE AND INTERRELATED MEASUREMENTS.

CLINICAL GOALS
- HYPNOSIS
- AMNESIA
- ANALGESIA
- IMMOBILITY
- ANXIOLYSIS. [1]

CAUSAL PHYSIOLOGICAL MECHANISMS
- HYPNOSIS: NERVOUS SYSTEM;
- AMNESIA: CNS; HORMONE GENERATION CONTRIBUTING TO MEMORY CONSOLIDATION
- ANALGESIA: SENSORY SYSTEM; PAIN RECEPTORS, PNS; CNS; PULMONARY ANAESTHESIA GAS EXCHANGE; HORMONE GENERATION (BLUNTS PAIN RECEPTORS)
- IMMOBILITY: MOTOR SYSTEMS; PULMONARY ANAESTHESIA GAS EXCHANGE;
- ANXIOLYSIS: VITAL SIGNS. [2]

PHYSIOLOGICAL MARKERS
- HYPNOSIS: NEUROLOGICAL SIGNALS
- AMNESIA: CLINICAL OBSERVATIONS OF INTRAOPERATIVE AWARENESS, HORMONE (A.K.A. ADRENELINE) GENERATION CONTRIBUTING TO MEMORY CONSOLIDATION AND ELEVATED INTRAOPERATIVE RECALL RISK (DUE TO BURNING OF LONG TERM MEMORY);
- ANALGESIA: CLINICAL OBSERVATIONS OF PAIN AND CONCENTRATION OF ANAESTHESIA VAPOURS TO PREVENT SURGICAL STIMULI (PAIN) MOVEMENT (MAC); AROUSALS, BODY MOVEMENTS;
- IMMOBILITY: CLINICAL SIGNS OF MOVEMENT, ELEVATED EMG ACTIVITY, MAC, PAMR AROUSALS, BODY MOVEMENTS;
- ANXIOLYSIS: ELEVATED VITAL SIGNS, INTRAOPERATIVE AWARENESS TRIGGERED HORMONAL GENERATION (A.K.A. ADRENELINE WITH THE RISK OF BURNING OF LONG-TERMS MEMORY/RECALL. [3]

DISCRETE MONITORED SIGNALS
- HYPNOSIS: NEUROLOGICAL/COGNITION SIGNALS INCLUDING EEG, AEP, AEP ENTROPY AND HIERARCHICAL-AEP (HAEP) MEASURES OF PERIPHERAL PAMR VS SENSORY ABR VERSUS PCPS INCLUDING STANDARD/DEVIANT AND MMN MEASURES
- AMNESIA: NEUROLOGICAL SIGNALS INCLUDING EEG, AEP, HAEP, CLINICAL OBSERVATIONS OF AWARENESS; EEG OR AEP AROUSALS;
- ANALGESIA: CLINICAL OBSERVATIONS OF PAIN, MAC;
- IMMOBILITY: EMG, MAC, EVOKED PAMR, CONTINUOUS PAM, MASSETER EMG, EEG OR AEP BODY MOVEMENTS;
- ANXIOLYSIS: ELEVATED VITAL SIGNS. [4]

INTERRELATED SIGNALS
- HYPNOSIS: NEUROLOGICAL/COGNITION MEASURES OF HYPNOSIS ACCOMPANIED WITH ELEVATED EMG/PAMR SIGNALS, OR HYPNOSIS ACCOMPANIED WITH ELEVATED VITAL SIGNS SUCH AS DURING MUSCLE-SUPPRESSANT INDUCED PARALYSIS WITH AWARENESS;
- AMNESIA: NEUROLOGICAL/COGNITION MEASURES OF HYPNOSIS ACCOMPANIED WITH ELEVATED VITAL SIGNS SUCH AS DURING MUSCLE-SUPPRESSANT INDUCED PARALYSIS WITH AWARENESS;
- ANALGESIA: NEUROLOGICAL/COGNITION MEASURES OF HYPNOSIS ACCOMPANIED WITH EEG OR AEP AROUSALS (AR), BODY MOVEMENTS (BM), SURGICAL STIMULI TIME-ALIGNED AR AND/OR BM;
- IMMOBILITY: EMG, MAC, EVOKED PAMR, PAM EMG, MASSETER EMG, SURGICAL STIMULI EVENT-CORRELATED AR AND/OR BM;
- ANXIOLYSIS: ELEVATED VITAL SIGNS. [5]

*FIG. 15*

A STRUCTURED APPROACH TO SEDATION, PAIN AND/OR ANAESTHESIA MONITORING

| A STRUCTURED APPROACH TO SEDATION, PAIN AND/OR ANAESTHESIA MONITORING |
|---|
| TRADITIONAL TRIAL AND ERROR APPROACHES DEPLOYED DURING SEDATIVE, PAIN-SUPPRESSOR AND ANAESTHETIC DRUG DEVELOPMENT OR PATIENT MONITORING ARE LIKELY TO BE AUGMENTED OR REPLACED WITH THE MORE SPECIFIC BIOMARKER ASSESSMENT APPROACHES, CAPABLE OF TEASING OUT THE INDEPENDENT AND INTERRELATED EFFECTS, ALONG WITH IMPLICATED COGNITIVE/PSYCHOLOGICAL MECHANISM AND MEASUREMENTS. [1] |

| SPECIFIC PHYSIOLOGICAL AND/OR COGNITIVE / PSYCHOLOGICAL SEDATION, PAIN AND/OR ANAESTHESIA-EFFECTS |
|---|
| EFFECTS INCLUDE (BUT ARE NOT LIMITED TO)-HYPNOSIS; AMNESIA,; ANALGESIA; MOBILITY; ANXIOLYSIS; VITAL SIGN CHANGES [2] |

| SPECIFIC PHYSIOLOGICAL AND/OR COGNITIVE / PSYCHOLOGICAL SEDATION, PAIN AND/OR ANAESTHESIA-MECHANISMS |
|---|
| *PHSYIOLOGICAL CONTROL SYSTEMS (MOST APPLICABLE TO A&CD)*: CENTRAL NERVOUS SYTEM (CNS); PERIPHERAL NERVOUS SYSTEM; SENSORY SYSTEM; MOTOR SYSTEMS; AUTONOMIC NERVOUS SYSTEM; OTHER PHYSIOLOGIC CONTROL SYSTEMS INCLUDING CENTRAL INTEGRATIVE (MAINLY LEARNING, MEMORY, AND POSSIBLE LATERALITY OF BRAIN FUNCTION), ENDOCRINE CONTROL MECHANISMS; PITUITARY HORMONES, ADRENAL GLANDS (HORMONES SUCH AS EPINEPHRINE/a.k.a ADRENALINE IMPLICATED DURING STRESS AND THE RELATED MEMORY CONSOLIDATION). *CELLULAR FUNCTIONS*. *INTEGRATIVE ORGAN FUNCTIONS (MOST APPLICABLE TO A&CD)*: MUSCLE; HEART; CIRCULATION; RESPIRATION; PULMONARY CIRCULATION, GAS EXCHANGE, AND CONTROL OF BREATHING; REGULATION OF BODY TEMPERATURE; [3] |

| SPECIFIC PHYSIOLOGICAL AND/OR COGNITIVE / PSYCHOLOGICAL SEDATION, PAIN AND/OR ANAESTHESIA-SIGNALS |
|---|
| *CNS/NEUROLOGICAL SIGNALS INCLUDE (BUT NOT LIMITED TO)*: FOREHEAD EEG SIGNALS; A1 EEG AND/OR AEP SIGNAL; A2 EEG AND/OR AEP SIGNAL; FP2 AND/OR AEP SIGNAL; FP1 AND/OR AEP SIGNAL; F7 AND/OR AEP SIGNAL (CHECK ??); F8 AND/OR AEP SIGNAL (CHECK ??); FPZ AND/OR AEP SIGNAL; Nz EEG AND/OR AEP SIGNAL; Iz EEG AND/OR AEP SIGNAL; ACTIVE NOISE CANCELLATION OUTPUT DRIVE; AEP STIMULUS OUTPUT; EEG MARKERS OF PAIN. *MUSCLE SIGNALS INCLUDE (BUT NOT LIMITED TO)*: EMG SIGNALS OF THE MASSETER, PAMR OR SUBMENTAL REGIONS. [4] |

| SPECIFIC PHYSIOLOGICAL AND/OR COGNITIVE / PSYCHOLOGICAL SEDATION, PAIN AND/OR ANAESTHESIA-SIGNAL MEASURES |
|---|
| *ANAESTHESIA-SPECIFIC EVENTS AND EPISODES; ePAMR DISCRIMINATORS OF MUSCLE SUPPRESSION; LINKAGES BETWEEN ANXIOLYSIS AND INTRAOPERATIVE RECALL-RISK; ONLINE MONITORING REQUIREMENTS; A SERIES OF NEW ONLINE A&CD DISPLAY INDICES; SIMULTANEOUS PAMR, ABR AND MLAEP MONITORING; NEURAL SOURCE ESTIMATION (NSE); AUTOMATED CLINICAL MARKERS OF SPA&CD; SEE NOTES FOR EXPANDED DETAILS. [5]* |

| SPECIFIC PHYSIOLOGICAL AND/OR COGNITIVE / PSYCHOLOGICAL SEDATION, PAIN AND/OR ANAESTHESIA-SIGNAL MEASUREMENT BIOLOGICAL MARKERS/EVENTS [6] |
|---|

| SPECIFIC BUT INDEPENDENT PHYSIOLOGICAL AND/OR COGNITIVE/PSYCHOLOGICAL SEDATION, PAIN AND/OR ANAESTHESIA-SIGNAL MEASUREMENT BIOLOGICAL MARKERS/EVENTS (SUCH AS NOCICEPTIVE-ANTINOCICEPTIVE BALANCE) [7] | SPECIFIC BUT INTERRELATED PHYSIOLOGICAL AND/OR COGNITIVE/PSYCHOLOGICAL SEDATION, PAIN AND/OR ANAESTHESIA-SIGNAL MEASUREMENT BIOLOGICAL MARKERS/EVENTS (SUCH AS ANAESTHESIA-INDUCED MUSCLE SUPPRESSION WITH ELEVATED ANXIOLYSIS AND AWARENESS) [8] |

*FIG. 17*

MAPPING OF THE PRINCIPAL A&CD FUNCTIONAL MEASUREMENT REQUIREMENTS APPLICABLE TO DIRECT AND INTERACTIVE ANAESTHETIC EFFECTS

| ANAESTHETIC EFFECTS | REF CHAP. | PHYSIOLOGICAL VARIABLE | PHYSIOLOGICAL PARAMETER | INDICATOR MEASURE |
|---|---|---|---|---|
| HYPNOSIS | 2-7 | EEG; AEP | EEG;ENTROPY;MF;SKEW;BISPECTRUM AND OUTPUTS;MLAEP; PCP; MMN | A&Cd; AEP AWARENESS COtx (AEP CONSCIOUSNESS TRANSITION) |
| AMNESIA | 2-7 | EEG; AEP | PCP;MMN | AEP AWARENESS |
| ANALGESIA | 2-7 | AEP | MLAEP DAS AND ENTROPY | AROUSALS/NOXIOUS STIMULI |
| IMMOBILITY | 2-7 | EMG; PAMR | EMG POWER; PAMR INDEX | EMG POWER AND ANAESTHETIC BALANCE |
| ANXIOLYSIS | 2-7 | OXIMATER | HRV;PTT;ECG; BPV | Sa02;ECG;HRV;BPV;PAW;PTT |

| INTERRELATED ANAESTHETIC EFFECTS | | PHYSIOLOGICAL VARIABLE | PHYSIOLOGICAL PARAMETER | INDICATOR MEASURE |
|---|---|---|---|---|
| ANXIOLYSIS AND HYPNOSIS | 2-7 | OXIMETER; EEG; AEP | HRV;PTT;ECG;BPV/ EEG ENTROPY; MF; SKEW;BISPECTRUM AND PRODUCTS;MLAEP;PCP;N-EFFECT;MMN | INTRAOPERATIVE RECALL FACTOR (IRF) |
| IMMOBILITY AND HYPNOSIS | 2-7 | EMG;PAMR; EEG; AEP | EEG;ENTROPY;MF;SKEW;BISPECTRUM AND PRODUCTS; MLAEP;PCP;N-EFFECT;MMN/ EMG POWER; PAMR INDEX | ANAESTHETIC BALANCE |

| AROUSALS AND MOVEMENTS | | PHYSIOLOGICAL VARIABLE | PHYSIOLOGICAL PARAMETER | INDICATOR2 MEASURE |
|---|---|---|---|---|
| AROUSAL-NOXIOUS STIMULI | 5;7 | AEP; EEG;PTT;ECG;HRV | FREQUENCY SHIFT; SIGNAL MORPHOLOGY; CONTEXT | AROUSAL-NOXIUOS STIMULI EVENT AND INDEX |
| AROUSAL-CORTICAL (GENERAL) | 5;7 | PTT;ECG;HRV | FREQUENCY SHIFT; CONTEXT | AROUSAL-NOXIUOS STIMULI EVENT AND INDEX |
| AROUSAL-SUBCORTICAL (GENERAL) | 5;7 | PTT;ECG | SIGNAL MORPHOLOGY; CONTEXT | AROUSAL-CORTICAL EVENT AND INDEX |
| MICROAROUSAL | 5;7 | EEG | FREQUENCY SHIFT; CONTEXT | MICROAROUSAL EVENT AND INDEX |
| BODY MOVEMENT | 5;7 | EEG;EMG | BASELINE SHIFT AND SIGNAL MORPHOLOGY; CONTEXT | BODY MOVEMENT EVENT AND INDEX |
| MOVEMENT TIME | 5;7 | EMG;EEG;PTT | BASELINE SHIFT AND SIGNAL MORPHOLOGY; CONTEXT | MOVEMENT TIME EVENT AND INDEX |

| ARTIFACT | | PHYSIOLOGICAL VARIABLE | PHYSIOLOGICAL PARAMETER | INDICATOR MEASURE |
|---|---|---|---|---|
| EOG | 2;3;4 | EOG | LOW FREQUENCY; SIGNAL MORPHOLOGY | EOG EVENT AND INDEX |
| EYE-MOVEMENTS | 2;3;4 | EYE-MOVEMENT | LOW FREQUENCY; SIGNAL MORPHOLOGY | EYE-MOVEMENT EVENT AND INDEX |
| 50/60 CYCLE OR RELATED | 2;3;4 | ALL CHANNELS | FREQUENCY SPECTRUM THRESHOLDS | ALL CHANNELS EVENT AND INDEX |
| ELECTROSURGICAL DISTURBANCE | 2;3;4;7 | ALL CHANNELS | HIGH FREQUENCY SPECTRUM THRESHOLDS | ALL CHANNELS EVENT AND INDEX |
| EMG BURST | 2;3;AI | EMG | BASELINE INCREASE | EMG EVENT AND INDEX |

| CRUCIAL CHARACTERISTIC PERIODS | | PHYSIOLOGICAL VARIABLE | PHYSIOLOGICAL PARAMETER | INDICATOR MEASURE |
|---|---|---|---|---|
| PHARMACODYNAMIC TRACKING | 2;AI | EEG | EEG;ENTROPY;MF;SKEW;BISPECTRUM AND PRODUCTS; | DOSAGE GUIDANCE |
| ISO-ELECTRIC CORTICAL SILENCE | 2;AI | EEG | SEF95; SIGNAL MORPHOLOGY; SKEW | ISO-ELECTRIC CORTICAL SILENCE EVENT |
| NEAR ISO-ELECTRIC CORTICAL SILENCE | 2;AI | EEG | SEF95; SIGNAL MORPHOLOGY; SKEW | NEAR ISO-ELECTRIC CORTICAL SILENCE EVENT |
| BURST SUPPRESSION | 2;AI | EEG | SEF95; SIGNAL MORPHOLOGY; SKEW | BURST SUPPRESSION INDEX |
| WAKE DISTURBANCE PERIODS | 2;3;4;7 | ALL CHANNELS | AROUSALS, ARTIFACT;EEG-SPECTRAL;BODY-MOVEMENT; MOVEMENT TIME | WAKE EVENT |
| GAMMA CONSC DISCRIMINATION | 2 | EEG | SPECTRAL ENTROPY | GAMMA POWER |
| NEURAL SOURCE ESTIMATION | 2;A2 | EEG | SOURCE RECONSTRUCTION | LATERALISATION-ANTERIORISATION |
| SIGNAL QUALITY STATUS | 2;7;AI | ALL CHANNELS | IMPEDANCE, CONTINUOUS TRACKING OF SIGNALS CHARACTERISTICS | SIGNAL QUALITY INDEX (SQi) |
| SIGNAL DROP-OUT | 2;7;AI | ALL CHANNELS | IMPEDANCE, CONTINUOUS TRACKING OF SIGNALS CHARACTERISTICS | SIGNAL QUALITY INDEX (SQi) |

*Figure 18*

SUMMARY OF CONVENTIONAL AND ANAESTHESIA-SPECIFIC EVENTS

| EVENT TYPE | ABBREVIATION | CLASSIFICATION METHOD |
|---|---|---|
| CONVENTIONAL AROUSAL, MOVEMENT AND ARTIFACT EVENT CLASSIFICATIONS | | |
| AROUSALS FROM SLEEP | Ar | [98; 332; 332] |
| BODY MOVEMENT | BM | [372] |
| MOVEMENT TIME | MT | [372] |
| MICRO-AROUSAL | Arm | [266] (1.5-3 S DURATION) |
| CORTICAL AROUSAL | cAr | [45; 342; 344; 345] |
| SUBCORTICAL (AUTONOMIC) AROUSAL | sAr | [45; 342; 344; 345] |
| ARTIFACT | Af | [456] |
| PROPOSED ANAESTHESIA-SPECIFIC AROUSAL, MOVEMENT AND ARTIFACT EVENT CLASSIFICATIONS | | |
| NOXIOUS STIMULI EVENTS | | |
| NOXIOUS STIMULI | Nx | NEW ANAESTHESIA-SPECIFIC EVENT; |
| NOXIOUS STIMULI AROUSAL (OVERALL) | ArNx | NEW ANAESTHESIA-SPECIFIC EVENT |
| NOXIOUS STIMULI CORTICAL AROUSAL | cArNx | NEW ANAESTHESIA-SPECIFIC EVENT |
| NOXIOUS STIMULI SUB-CORTICAL AROUSAL | sArNx | NEW ANAESTHESIA-SPECIFIC EVENT; [45; 342; 344; 345] |
| NOXIOUS STIMULI BODY MOVEMENT | BMNx | NEW ANAESTHESIA-SPECIFIC EVENT |
| AROUSAL EVENTS | | |
| OVERALL ANAESTHESIA-SPECIFIC AROUSALS | AAr | COMBINATION OF CONVENTIONAL AND ANAESTHESIA-SPECIFIC AROUSALS |
| QUICK AROUSAL | Arq | PER CONVENTIONAL EXCEPT (0.25-3 S DURATION) AND SLEEP STATE SUBSTITUTED FOR UNCONSCIOUSNESS |
| QUICK CORTICAL AROUSAL | cArq | PER CONVENTIONAL EXCEPT (0.25-3 S DURATION) AND SLEEP STATE SUBSTITUTED FOR UNCONSCIOUSNESS |
| QUICK SUBCORTICAL AROUSAL | sArq | PER CONVENTIONAL EXCEPT (0.25-3 S DURATION) AND SLEEP STATE SUBSTITUTED FOR UNCONSCIOUSNESS |
| QUICK MICRO-AROUSAL | Armq | PER CONVENTIONAL EXCEPT (0.25-3 S DURATION) AND SLEEP STATE SUBSTITUTED FOR UNCONSCIOUSNESS, AND INCLUDES OVERALL CORTICAL AND SUBCORTICAL EVENTS |
| QUICK MICRO-AROUSAL CORTICAL | cArmq | PER CONVENTIONAL EXCEPT (0.25-3 S DURATION) AND SLEEP STATE SUBSTITUTED FOR UNCONSCIOUSNESS |
| QUICK MICRO-AROUSAL SUBCORTICAL | sArmq | PER CONVENTIONAL EXCEPT (0.25-3 S DURATION) AND SLEEP STATE SUBSTITUTED FOR UNCONSCIOUSNESS |

From Figure 19

| MOVEMENT EVENTS | | |
|---|---|---|
| QUICK BODY MOVEMENT | BMq | PER CONVENTIONAL EXCEPT (0.25-3 S DURATION) AND SLEEP STATE SUBSTITUTED FOR UNCONSCIOUSNESS |
| ARTIFACT | | |
| ARTIFACT | AAf | INCLUDES CONVENTIONAL AND ANAESTHESIA-SPECIFIC DEFINITIONS AND ALL SIGNAL BLACK OUT-PERIODS. |
| TOTAL ARTIFACT TIME | AAft | TOTAL TIME OCCUPIED BY CONVENTIONAL AND ANAESTHESIA-SPECIFIC ARTIFACT DURING THE PRECEDING 60 S PERIOD (CONVENTIONAL DEFINITION INCLUDING ALL SIGNAL BLACK OUT PERIODS.) |
| RECOMMENDED AROUSAL, ARTIFACT AND NOXIOUS STIMULI ANAESTHESIA-SPECIFIC ONLINE INDICES | | |
| OVERALL ANAESTHESIA-SPECIFIC AROUSAL INDEX | AAri | RUNNING SCORE OF ALL CONVENTIONAL AND ANAESTHESIA-SPECIFIC AROUSALS DURING PRECEDING 60 S PERIOD |
| OVERALL ANAESTHESIA-SPECIFIC CORTICAL AROUSAL INDEX | AcAri | RUNNING SCORE OF ALL CONVENTIONAL AND ANAESTHESIA-SPECIFIC CORTICAL AROUSALS DURING PRECEDING 60 S PERIOD |
| OVERALL ANAESTHESIA-SPECIFIC SUBCORTICAL AROUSAL INDEX | AsAri | RUNNING SCORE OF ALL CONVENTIONAL AND ANAESTHESIA-SPECIFIC SUBCORTICAL AROUSALS DURING PRECEDING 60 S PERIOD |
| OVERALL ANAESTHESIA-SPECIFIC BODY MOVEMENT INDEX | ABMi | RUNNING SCORE OF TOTAL SCORE OF CONVENTIONAL (BM) AND QUICK ANAESTHESIA-SPECIFIC (BMq) EVENTS DURING PRECEDING 60 S PERIOD |

*Figure 19* CONTINUED

ANAESTHESIA AND CONSCIOUSNESS DEPTH MONITORING SYSTEM

FIELD OF INVENTION

The present invention relates to the field of evoked electrophysiological potential signal monitoring and in particular can be applied as a means to determine the sentient state of an individual, and as a means to authenticate the physiological, electrical or electromagnetic source of a signal.

BACKGROUND OF INVENTION

The process of monitoring the sentient state of a subject is an essential pre-requisite to reliable tracking of many physiological parameters or the effective clinical deployment of many monitoring systems.

Additionally, and in the context of general monitoring of physiological signals, the requirements to distinguish the source of a signal can be a critical step. In particular, a physiological monitoring system output measure typically relies upon the assumption that the output measure is predominantly based on a known source of interest. In the case of cerebral monitoring during anaesthesia, for example, output measurement indices relied upon as a basis for the determination of anaesthesia-depth can incorporate authentic neural signals of interest emanating from the central nervous system (CNS), electromyography signals emanating from muscle activity and generated by the peripheral control system (PCS), or artifact generated as a results of factors such as arousals, body movements, electrical noise or electromagnetic noise.

In the case of monitoring sentient state the determination of an individual's response to external stimulus can be representative of a unique aspect of consciousness state. In particular an individual's coherence with the environment or vigilance to external prompts, or in this particular case the response to an external stimulus provides important information regarding an individual's state of alertness from a safety or operational proficiency perspective. Furthermore, in the context of anaesthesia-depth, sedation or testing procedures such as hearing function determination, the sentient state of an individual can be crucial in terms of accurate interpretation of dosage guidance or hearing function.

Definitions Applicable to Body and Claims Section of Patent Document

Sentinel, sedation, anaesthesia and/or pain (SSAP): refers to patient states comprising those of consciousness, alertness, attention, awake, responsiveness, sleep-state; vigilance; awareness; calmness; agitation; anxiolysis; fatigue; brain function; physiological status; cognition; psychological; psychological and/or sentient states.

SSAP monitoring: refers to a monitoring system capable of monitoring one or more of the above listed SSAP states.

MAIN CLAIM PRINCIPLES

AEP Latency-Interal Analysis

AEP latency-interval analysis demonstrated substantial congruence between clinical signs of anaesthesia-depth and AEP latency-interval parameters. In particular, the value of early (0-15 ms) and broad-band (0-140 ms) latency anaesthesia monitoring candidates were established. AEP latency-interval analysis demonstrated substantial congruence between clinical signs of anaesthesia-depth and AEP latency-interval parameters. In particular, the value of early (0-15 ms) and broad-band (0-140 ms) latency anaesthesia monitoring candidates were established.

The early latency region (0 to 15 ms), may be markers of muscle-suppression, and a useful tool for anaesthesia monitoring. In particular, the PAMR signals may provide accurate discrimination between neurogenic (CNS) and ePAMR (peripheral) signals. While conventional anaesthesia monitoring mainly relies on the forehead monitoring of electromyography (EMG) originating from facial muscles, the close proximity of these signals to EEG signals can lead to the inadvertent combining of these distinctively different signal groups. However, while the coupling between early latency ePAMR and EEG signals can lead to mistaken hypnosis guidance, independent component or latency-interval analysis of the ePAMR signals could enable a unique and potentially valuable anaesthesia muscle-suppression tracking method.

Subtraction of Long and Short Evoked Signal Discrimination Techniques:

It was established that subtraction of long and short (256, 512 and 1024 sweep) moving time averages (MTA) can improve the discrimination between neural signals of interest versus unwanted artifact.

ABR Spectral Click Detection and Evoked Potential Signal Validation Techniques:

It was established that FFT processed auditory brainstem responses (ABRs) were capable of tracking stimulus connection and troublesome spectral disturbances such mains and electrosurgical interference.

AEP Initialisation Assurance and Compensation:

The need for enabling an automatic means to ensure appropriate AEP averaging initialisation (start-up baseline) time before relying on AEP-average measures was established. In particular, the 256-sweep AEP MTA examined in this study required 38 s before the first complete AEP value could be computed. The MTA initialisation time constraints coupled with the high degree of artifact at the start of monitoring, and the fast unconsciousness onset resulting from the typical start of anaesthesia bolus injection, demonstrated the need to consider faster AEP averaging methods for future studies.

Combination of Non-Linear Dynamic and Conventional Evoked Potential Predictors of Anaesthesia Consciousness-State:

The deployment of optimal combinations of classical evoked potential analysis methods (such as but not limited to differential/first derivative analysis) and non-linear dynamic analysis methods as a means to predict SPA&CD.

Processed Arx MTA, Non-Linear Dynamic Evoked Potential Predictors of Anaesthesia Consciousness-State:

The deployment of optimal combinations of faster (2.2. online delay versus 38 s with 256-sweep) moving time averages incorporating autogression modelling with an external input function (arx), classical evoked potential analysis methods (such as but not limited to differential/first derivative analysis) and non-linear dynamic analysis methods as a means to predict SPA&CD.

Any Combination of Processed Arx MTA, Slow MTA, Non-Linear Dynamic Evoked Potential Predictors of Online Anaesthesia-Specific Events:

The deployment of optimal combinations of fast arx and slower MTA, classical evoked potential analysis methods (such as but not limited to differential/first derivative analysis) and non-linear dynamic analysis methods as a means to online events relevant to SPA&CD monitoring such as consciousness transitions and noxious stimuli events, and greater discrimination between signal disturbances and physiological signals of relevance. Additionally, the optional detection of quick events ranging between 0.5 and 3 seconds for the detection of body movements, arousals and other physiological signal disturbances combined with cluster analysis as a means to predict anaesthesia reversal.

A& CD Functional Measurement Requirements:

Functional measurement requirements included the need to track electrode impedance and signal quality status; the need to monitor anaesthesia-specific events and episodes (outlined below); and the need to track specific and interrelated anaesthesia-effects. Specific anaesthetic-effects were defined as hypnosis, amnesia, analgesia, immobility, and anxiolysis, while interrelated effects were defined as episodes of awareness accompanied with anaesthetic-induced muscle-suppression or elevated anxiolysis.

Anaesthesia-Specific Events and Episodes:

Important anaesthesia-specific online events were identified including arousals (Ar: overall), conical arousals (cAr), microarousals (Arm), body movements (BM), and movement time (MT). Anaesthesia-specific events established as potentially valuable online A&CD markers included noxious stimuli events (Nx), quick (0.25 to 3 s duration) body movements (BMq), and quick arousals (Arq). Noxious stimuli were further classified according to body movement (NxBM), conical (NxC), and subcortical (NxS) types, while quick arousals were further classified according to quick cortical (cArq) and quick subcortical (sArq) types. Additionally, a series of online anaesthesia-specific indices were established as a means to enable the anesthesiologist to track the severity and rate of important events such as movements, arousals and particularly noxious stimuli, applicable to anaesthesia-reversal and implicated with intraoperative awareness.

Artifact processing requirements were established and included the detection and cancellation of EOG signals, eye-movements, 50/60 cycle or related interference, electrosurgical disturbances, EMG signal bursts or EMG modulation of EEG signals, in order to avoid excessive filtering or rejection of neural correlates of interest.

Episodes of intraoperative awareness accompanied by elevated anxiolysis or muscle paralysis; the onset or occurrence of near or iso-electric cortical silence; near or burst-suppression periods; wake disturbance periods, and elevated gamma power as a marker of consciousness state were established as relevant changes which should be tracked during anaesthesia monitoring. The requirements and design principles were developed to capture integrated vital sign measures representative of anaesthesia-induced interactions between peripheral, central and anxiolysis physiological parameters. An example of how this information is conveyed to the anesthetists in terms of useful anesthetics balance measures (CNS activity corresponding to consciousness-depth changes versus peripheral activity changes representative of patient mobility risk) is shown in FIG. 6 and FIG. 7.

ePAMR Discriminators of Muscle Suppression:

Improved decoupling of EEG and EMG measurement techniques using independent EMG (masseter and/or PAMR) signals, were established. PAMR and masseter signal measures were introduced as potentially valuable markers of anaesthetic muscle suppression. In particular, evoked early latency signals across the PAMR region were found to be substantial anaesthesia consciousness state discriminators, with the potential to delineate between EEG and EMG signals. Improved decoupling between EEG and EMG signals could lead to more precise prediction of consciousness states and potentially help detect the onset or incidence of intraoperative awareness. Consequently, the detection of PAMR changes corresponding to stimulus amplitude changes can be representative of anaesthetic muscle suppression.

Linkages Between Anxiolysis and Intraoperative Recall-Risk:

Elevated anxiolysis marked by vascular constriction, racing heart, and increased blood-pressure. Based on these factors the link between elevated anxiolysis and intraoperative awareness recall was established. Consequently, the requirement for vital sign monitoring as an integral function of A&CD monitoring was established.

AEP Noise Coupling Effect and Countermeasures:

There is a coupling-effect between AEP and background artifact signals resulted in increased consciousness-state values and a typical AEP anaesthesia-depth indicator switch-like transition corresponding to consciousness transitions. In particular, severe signal disturbances were found to occur during critical phases of anaesthesia, including fast consciousness transitions and deep anaesthesia electrosurgical periods.

BIS™ data smoothing characteristics conceal potentially valuable anaesthesia-specific indicators such as noxious stimuli events and possibly mask important events leading to anaesthesia-reversal. In contrast, AEP values were found to demonstrate sensitive detection of anaesthesia-specific body movements and noxious stimuli events. AEP non-linear dynamical analysis techniques (AEP entropy) were also shown to be potentially useful discriminators of different arousal, artifact and movement events. The invention uses non-linear dynamic techniques to delineate between the underlying non-linear neurological signals implicated deep hypnosis and the more complex and less deterministic nature of wake periods signals. Subject to more extensive and larger scale studies the further refinement of the first generation entropy AEP algorithms could be promising A&CD measurement candidates, particularly as it relates to describing peripheral and neural anaesthesia-specific events, and decoupling between unwanted signal disturbances, physiological artefact, and neural signals. In order to enhance the discrimination between AEP neurogenic markers of A&CD versus residual noise, multiple MTA (15-sweep; 256; 512; 1025) subtraction techniques, based on the known relationship between SNR and the number (n) of AEP-average sweeps (SNR $\alpha$ $\sqrt{n}$sweeps) are preferably used.

Hybrid A& CD Multivariate Inputs:

Anaesthesia indicators based on optimal combinations of slower trending EEG parameters, coupled with fast (2.2 s) and slow MTA differential and non-linear dynamic (entropy) AEP values, computed across a wide-band of different latency intervals, including early latency (0-28 ms) signals appearing across the PAMR region, and later latency AEP measures (80-140 ms). The combination of these latency-interval measures demonstrated the potential to enable faster detection of consciousness transitions, greater responsiveness to online events, and superior discrimination between peripheral and central physiological signals.

New Standardised A&CD Measurement Methodology:

A standardised A&CD measurement methodology was established as a means to undertake an expanded clinical study with more consistent and accurate anaesthesia-depth indicator performance outcomes. In particular, AROC performance tests were deployed to describe A&CD indicator prediction accuracy, 2-sample t-tests spanning fast slope consciousness transitions enable responsive consciousness transition detection, and standard deviation and average consciousness states values were deployed as a measure of separation between consciousness periods. Univariate, multivariate and binary logistic statistics were calculated as a means to describe associations between consciousness states and BIS™ and AEP anaesthesia-depth indicator values. Additionally, measures of quick (0.5 to 3 seconds) events comprising of arousals (Arq), and body movements (BMq) were identified as potentially useful online anaesthesia-specific markers. Noxious stimuli (Nx) episodes were classified according to body-movement related (BMNx) and conical arousal related (ArNx) events. The augmentation of these anaesthesia-specific events with conventional arousal (Ar), micro-arousal (Arm), body movement (BM), movement time (MT), and artifact (Af) events could have important implications in the context of crucial anaesthesia periods such as the onset or incidence of pain, awareness, mobility or elevated anxiolysis.

These findings established the background for an improved A&CD design requirement specification and the basis from which more extensive clinical studies can be conducted.

Integrated Sensor Attachment (ISA) System:

These requirements included integrated oximetry and associated output products including plethysmography waveform, pulse transit time (PTT), pulse arterial tone (PAT), heart rate variability (HRV), heart rate HR, subcortical (autonomic) arousals (sAr), along with associated blood-pressure derivatives. The provision for airflow monitoring as an integral ISA function was formulated as a means to enable online respiration measurements. The monitoring of these parameters coupled with masseter and PAMR (EMG) activity, EEG and AEP neurophysiological parameters, and ECG signals derived from these signals, were described as a means to accommodate the essential measures relevant to A&CD monitoring. Additionally, ISA system requirements included onboard signal quality indicators, embedded pressure-activated cells capable of regelling and re-abrading electrode connections, and "concertina-type" size-adjustment functionality. Special requirements included intuitive light emitting diode (LED) indicators capable of localised-sensor quality status indication. The sizing element can further utilize other retractable and/or expandable elements to allow each sensor which forms part of the integrated sensor attachment device to be re-positioned (registered) on the patients head in accordance to the optimal location of the said sensor and also in accordance to the various facial or cranial structures evident across different ages, nationalities, and other population variances. Such retractable and expandable embodiments could (but not limited to) include "z" sections "spiral" or any other interlocking shape. In particular shape structures minimizing entanglement, and shape structures able to provide most streamlined and less bulky formats are preferred. For example, the sizing expandable and retractable elements should sit closely to the subject's face and and/or head to avoid being knocked, displaced or dislodged during medical procedures. Similarly the sizable and retractable elements need provide the minimal concealment of the patients head or face during medical procedures.

Patient Interface:

Patient interface requirements were established and included the need for continuous online signal quality and impedance measures. The requirements were established for online and automatic mode-configuration (hybrid or EEG-based); sensitivity and filtering adjustments, and display configurations driven by the format of the connected ISA device and signal quality status.

Signal Processing Requirements:

Signal processing requirements established to counter signal disturbances included the need to counter troublesome monitoring episodes such as study initialisation, episodes of electrosurgical intervention, and start and end of monitoring periods. Additionally, the requirements for adaptable input pre-filtering and digital online filters able to be automatically adjusted in accordance to changing monitoring conditions were established.

Evoked Potential Hierarchical Stimulus Generation Requirements:

Evoked potential hierarchical stimulus generation requirements were established to enable simultaneous tracking of AEP responses during servo-controlled stimulus optimisation.

Stimulus optimisation included adjustments of rate, intensity, standard/deviant ratio, stimuli shape, and stimulus spectral parameters. Other requirements and design principles included the need to generate different stimulus formats based on the specific anaesthesia stage and the corresponding anaesthesia measurement requirements applicable to these different stages. Stimulus formats included standard/deviant stimuli sequences, click, warble, chirp, tone, speech, and specialised audio sequences. The desired evoked response requirements ranged from evoked early latency responses (such as PAMR) as markers of peripheral activity, ABR signal quality and stimulus connection status, and anaesthesia-cognition specific sequences of standard/deviant MMN stimulus test paradigms, designed to capture early warning markers of intraoperative awareness.

AEP Hierarchical Analysis

The AEP hierarchical analysis was established in order to disassemble the composite AEP signals into separate channels of information relevant to anaesthesia-specific response effects. The hierarchical analysis requirements included the need to verify ABR obligatory sensory responses, distinguish evoked peripheral measures (PAMR), and to capture higher level AEP processing contingent potential (PCP) measures, by way (for example) of delineating between N1-effect and those of higher brain MMN brain functional changes which are implicated during long term intraoperative memory consolidation.

Online Monitoring Requirements:

Online monitoring requirements were established including: 1) Techniques capable of tracking of obligatory evoked PAMR (ePAMR) responses as an improved measure of muscle suppression. These techniques have the potential to enable more precise measures of muscle suppression which in turn can contribute to the delineation of the separate immobility and hypnotic anaesthetic-effects. Failure to effectively distinguish between these 2 states can result in awareness during anaesthesia-induced muscle suppression. In contrast to conventional cerebral monitors which tend to track forehead EMG activity generating by facial muscles, the deployment of PAMR and masseter EMG measures can provide greater decoupling between these distinctly separate central and peripheral signal origins; 2) Intraoperative recall-factor (IRf) based on the interrelationship between anxiolysis levels (stress or anxiety) derived from vital-signs and awareness (consciousness level) derived from neurological correlates; 3) The principal effects of anaesthesia comprising of hypnosis, amnesia, immobility, analgesia and anxiolysis, together with interrelated effects including awareness accompanied with elevated anxiolysis or anaesthetic-induced paralysis: 4) The need for accurate and reliable detection of conventional artifact and arousal detection augmented with anaesthesia-specific events; 5) Concurrent online fast (2.2 s response) measures representative of consciousness transitions, together with measures capable of capturing slower trending information including subtle dosage changes; 6) Continuous online adaptation (mediation) of multivariate analyses as a means to optimise A&CD measurements according to the changing monitoring conditions.

A Series of New Online A&CD Display Indices:

A series of new online A&CD display indices (i) were established as a means to track a number of important anaesthesia-specific effects including overall anaesthetic balance (ABi), intraoperative recall factor (IRf), optimally combined measures of electroencephalography (EEGi), optimal combinations of auditory evoked processing contingent potentials (APCPi), burst suppression (BSi), muscle suppression (MSi), and anxiolysis (ANXi). The requirement for ACPi determination comprised of capturing cognitive measures online using a stimulus sequence capable of revealing graduated measures using hierarchical analysis as noted above. Online event detections were found to be important online monitoring A&CD design considerations.

Background intellectual property has been established and comprises of three key documents, including an initial A&CD patent application titled "Methods and Apparatus for Monitoring Consciousness", a second patent application titled "Method and Apparatus for Monitoring Consciousness During Anaesthesia" published as WO 2006/122349 by the World International Property Organisation [7; 8], and a third patent application currently in process. In total one patent has been granted, two have been accepted and seven are pending as it relates to the initial European application [7]. The design and innovation outputs have been established in the form of design requirements, systems flow diagram, and patents forming the basis of a new generation A&CD system now under development.

Simultaneous PAMR, ABR and MLAEP Monitoring:

An important future study requirement is to investigate the mechanisms responsible for the transition from awareness to unconsciousness. This thesis established that simultaneous derivations of PAMR, ABR and MLAEP measures are feasible during routine clinical anaesthesia, but it was also found that these measures essentially behave in a binary manner versus more graduated measures generated by BIS™. Therefore, the question for future research arises as to whether AEPs monitored during anaesthesia behave in this switch-like manner due to a anaesthesia muscle-suppressant "neural-blocking" effects relating to the sedation peripheral auditory functions, or whether this transition is an accurate predictor of the underlying hypnosis effects during anaesthesia.

Automated Clinical Markers of SPA&CD:

The identification of more specific A&CD correlates, more effective clinical observations scales, more sensitive cognitive AEP measures, and a better understanding of the mechanisms responsible for the anaesthesia-specific effects are future research considerations. The investigation into improved clinical-command stimuli and corresponding test techniques capable of overcoming existent limitations remains an important area for future research. Anaesthesia monitoring system clinical assessment and clinical scales of anaesthesia rely upon equivocal clinical response tests rely on patient-co-operation, excessive test intervals, and investigator interpretation. While consciousness transitions can be detected accurately with a few seconds using new fast AEP methods, the traditional command-stimuli tests are based on manually conducting clinical response tests at consecutive intervals of 10 s or more. Despite the widespread deployment of Ramsay, OAA/S and other popular clinical scales, these tools cannot discriminate between crucial short-term versus long-terms memory functions implicated during intraoperative recall. Therefore, the question as to whether fast AEP measures should be deployed to overcome timing and patient-co-operation limitations of conventional scales of anaesthesia remains an important subject for future investigations.

Neural Source Estimation (NSE):

The A&CD monitoring system incorporates neural source estimation (NSE) of one or more evoked or continuous neurological signals and incorporates any combination of steps or means comprising:

The online or "near realtime" monitoring of EEG anteriorisation;

The online or "near realtime" monitoring of cognitive unbinding;

The online or "near realtime" monitoring of EEG lateralisation/hemispherical changes;

The online or "near realtime" monitoring of these factors using as few as 3 electrodes;

One embodiment cabn include (but not limited to) 3 electrodes such as the frontal central (Fpz or nasion), left (Fp1), and right (Fp2) hemispherical registrations, together with anteriorisation using an additional posterior (nape/Inion/Iz) electrode.

The online or "near realtime" monitoring of NSE incorporating any combination of non-linear dynamic EEG time-series, spatiotemporal dynamics implicated during audiovisual processing, spatio-temporal brain dynamics corresponding to processing and/or the integration of sound localisation cues;

The online or "near realtime" monitoring of lateralisation or anteriorisation changes during anaesthesia a combined with any combination of non-linear dynamic (including complexity and entropy type transforms), spectral, power or other amplitude relationships, and/or phase or bispectral and related products.

Dosage Control Method and Systems:

Investigations into more sophisticated dosage control, capable of tracking specific and interrelated effects of anaesthesia as described in this thesis, is an important subject for future research. The ability of closed-loop dosage systems to minimise preventable incidents such as dosage-overshoot, while enabling more precise anaesthesia-specific control across the principal physiological and psychological effects of anaesthesia is a subject for future research. The investigation into the benefits and risks associated with emerging dosage delivery technologies such as low frequency ultrasonic skin transdermal perfusion and nano-pharmaceuticals are also worthy considerations.

SPA&CD Drug Development Method and System:

Drug development based on new experimental techniques and technological approaches remains an essential requirement for future research. In particular, investigations into more specific biomarkers reflective of direct and interrelated anaesthesia-specific effects are important considerations. The development of more sensitive and specific anaesthetics remains an important subject for future research. While conventional anaesthetics have been formulated on the basis of empirical study outcomes (analysis of desirable effects) more effective techniques using biological markers (biomarkers) continue to evolve. Biomarkers can now be identified according to the changes detected across physiological, cognitive, neurochemical and cellular mechanisms corresponding to anaesthetic-effects. More recent drug development techniques are capable of testing anaesthetic-specific activity as it relates to precise groups of neural, nerve or muscle cells responsible for specific anaesthetic effects. Transgenic modification (animal and insect models) in vivo cellular monitoring, and more recent techniques enabling the in vitro monitoring of anaesthetic cellular activity are showing promise in the pursuit of improved sedatives or anaesthetics. These new technologies and experimental techniques could enable the behavioural characterisation of specific neural receptors responsible for memory functions implicated during intraoperative recall. Designing safer drug compounds utilising direct and specific biomarker measures corresponding to the activation or desensitisation of these anaesthetic-specific mechanisms may lead to superior anaesthetics for the future. The question arises as to whether improved anaesthetics could deactivate long term memory receptors during anaesthesia, without inadvertently suppressing cardiac or respiratory functions. Furthermore, the development of more sensitive and safer anaesthetics could enable anaesthesia usage amongst high-risk groups (such as trauma patients), currently excluded from anaesthesia.

Integral SPA&CD Monitoring System Cognitive Marker Data Base and Normative Assessment System:

The investigation into reversible and permanent anaesthesia-induced cognitive dysfunction remains an important topic for future research. Patients are susceptible to a range of adverse incidents during anaesthesia which can temporarily or permanently affect cognition, including oxygen deprivation, excessive anaesthesia (linked to mortality rates), insufficient anaesthesia (can result in intraoperative awareness and PTSD), or restricted circulation of respiratory function (can lead to cognitive impairment). Cognitive assessments of the effects of short and long term memory functions, cognition responsiveness and other tests capable of identifying potential anaesthesia-related cognitive dysfunction should be subjected to both preview and follow-up studies. While studies have reported the link between deep sedation and patient mortality rates, large scale cognition follow up studies remain an important agenda for future research. A study designed to establish and validate a standardised battery of anaesthesia-specific cognitive tests should be considered. The establishment of standardised automation methodologies can potentially streamline the undertaking of larger multi-centre clinical studies. The individual-patient cognitive evaluation outcomes can be compared to larger normative databases or the patient's own cognition performance as a reference to cognitive deterioration, recovery or improvement. The combination of appropriate assessments and decision support based on validated tests and statistical based methodologies could contribute to the development of more individual patient-specific anaesthetic compounds and delivery techniques.

Online Monitoring:

Advancements include the establishment of PAMR tracking representative of the balance between CNS, and peripheral activity bordering the brain region. Online prediction of intra-operative awareness can be achieved by correlating periods of elevated psychological or physiological stress (anxiolysis) with A&CD neurophysiological measures. These periods of intra-operative recall-stress factor (IRf) can be indicative of muscle suppressant induced paralysis, accompanied by consciousness. The online functions include noxious stimulus detection and noise discrimination monitoring methods based on optimal combinations of linear, non-linear dynamic, and latency interval parameters (per clinical study outcomes). Furthermore, faster online consciousness detection (2.2 s response delay), and more cognitively sensitive A&CD monitoring techniques were established based on these optimal AEP analysis combinations. Additionally, estimated neural source estimation based on tracking changes in EEG hemispherical activity and anteriorisation were identified as potentially valuable correlates of A&CD monitoring.

In Terms of Online Monitoring/Processing and Operator Interface:

Display indications were established and organised into four categories comprising of important A&CD monitoring properties, specific A&CD monitoring requirements, special A&CD requirements, and future requirements.

Firstly, important A&CD monitoring properties include the need for exceptional system reliability and robustness suitable for demanding operating theatre clinical applications; consistent and minimal online measurement response delay; a high tolerance to electrosurgical and other signal disturbances; safe and dependable pharmacological tracking: and a high degree of discrimination between A&CD neural, peripheral, noxious stimuli, and background noise signals. Secondly, specific A&CD monitoring indications include an overall A&CD integrated index; fast detection of consciousness transitions; graduated A&CD measures; tracking periods of elevated intra-operative awareness and recall risk (such as unconsciousness accompanied with high anxiolysis); tracking vital sign and corresponding anxiolysis state; tracking anaesthetic balance, and detection of important events and periods. Important events include awareness, noxious stimuli, EMG bust, body movements, signal dropouts, arousals, eye movements, electrosurgical interference, and mains interference. Important periods or signal tracking includes EEG burst suppression and cortical silence. EMG power, gamma power, anxiolysis level, integrated measures of anxiolysis and hypnosis depth, and signal quality and sensor connection status. Thirdly, special A&CD requirements include the integration of clinical observations; spectral display of important A&CD signal periods and events; system adaptation to changing online monitoring conditions including increased environmental or background physiological signal disturbances; and stimulus detection (during AEP monitoring). Future requirements include hierarchical AEP cognition tracking; continuous AEP test and measurement servo optimisation; integrated and more effective clinical anaesthesia/sedation scales; consistent operation during the administration of special case NMDA/opioid anaesthetics, and monitoring patient subgroups such as children, the aged or those with neurological disorders including dementia (see also operator interface design requirements).

Linkages Between Anxiolysis and Intraoperative Recall-Risk:

Elevated anxiolysis marked by vascular constriction, racing heart, and increased blood-pressure. Based on these factors the link between elevated anxiolysis and intraoperative awareness recall was established. Consequently, the requirement for vital sign monitoring as an integral function of A&CD monitoring was established.

SUMMARY OF INVENTION

An integrated sensor attachment apparatus incorporating a single-substrate patient-applied part for monitoring physiological, including cognitive, signals, the apparatus comprising of at least one of; vital sign monitoring sensor, postauricular muscle (PAM) monitoring sensor, masseter sensor, integrated reflective oximeter sensor, integrated or attached ear-located oximeter monitoring sensor.

A further device and method to monitor the pain and/or sedation and/or anesthesia-depth of a subject, the device comprising: A PAMR and a vital sign monitoring signal channel, a microprocessor to compute at least one output indicator of said subject's state of hypnosis, amnesia, analgesia, immobility, anxiety, pain, sedation or awareness measures, a microprocessor to compute measures of PAMR or masseter EMG, a microprocessor to compute masseter EMG, a microprocessor to compute the discrimination between masseter and/or PAMR EMG and central nervous system (CNS) signals.

A further apparatus and method for acquiring physiological data from a living being or in vitro sample for the physiological, psychological, cognitive or cellular status comprising: means for acquiring at least one stimulus-evoked biosignal response; means for calculating at least one measurement value from the at least one acquired evoked biosignals wherein the calculation incorporates the computation of non-linear dynamical (NLD) transform from at least one evoked response biosignal representative of changes within said biosignal.

A biological monitoring apparatus incorporating parts enabling the minimization of unwanted environmental or external system noise, by way of monitoring or sensing unwanted noise within a monitoring environment and then processing this sensed signal to enable a noise cancellation system comprising: an input sensing and/or input monitoring part enabling the cancellation of the unwanted noise within the wanted signal; a part capable of adjusting the noise characteristics of one or more channels of sensed or monitored noise in such a way as to produce an optimal noise cancellation signal; a part capable of combining a noise cancellation signal with a monitored signal of interest so that the resulting signal outcome comprises of the signal of interest with the unwanted signal diminished or eliminated;

Apparatus for determining and monitoring the characteristics of unwanted noise and distortion, the method including: a microprocessor device programmed to continuously track environmental, background physiological and/or other unwanted noise and distortion, at least one microprocessor device, a microprocessor device programmed to continuously compute the association between predefined frequency spectral noise and distortion characteristics and the frequency spectrum characteristics of a monitoring system.

A biological monitoring apparatus incorporating a means of minimizing unwanted environmental or external system noise, by way of automatic, manual or computer-assisted data acquisition sample and hold adaptation incorporating an adjustable input signal sample and hold acquisition window and comprising an adjustable sample and hold aperture window device enabling the sample and hold of the input signal at the points in time where noise or interference signals have least impact on the signal of interest, versus the peaks or higher level noise spikes where such interference can other wise be accentuated;

sample and hold aperture window timing control capable of being synchronized with external equipment timing reference or sensed (such as via external environment noise sensors) to enable the data acquisition aperture to be interleaved between the most prominent noise peaks within the input signal of interest, to ensure the effects of unwanted external cyclic noise are minimized;

a device capable of determining and resolving the timing reference directly related to unwanted external cyclic noise;

a device capable of deriving an optimal acquisition sampling rate and aperture window from an externally connected (wire and/or wireless, wire, optical, magnetic, capacitive or other) timing signal or noise tracking sensor so that the acquisitioned data points are interleaved between the unwanted cyclic noise peaks, which would otherwise be accentuated within the acquisitioned signals of interest;

a sample and window timing device enabling the aperture window to be delayed so as to minimize unwanted external signal interference:

a sample and window timing device enabling the aperture window delay and width to be controlled so as to minimize unwanted external signal interference.

A device for determining optimal combinations of drug delivery compounds corresponding to a subject's monitored states comprising of any of: hypnosis, amnesia, analgesia, immobility, anxiolysis, vital signs, or online events.

BRIEF DESCRIPTION OF THE DRAWINGS

FIG. 8 256-sweep AEP averages plotted from anaesthetised surgical patient data recording showing study time(s) on x-axis and AEP NLD anaesthesia-depth indicator values on y-axis.

FIG. 9 15-sweep arx AEP averages plotted from anaesthetised surgical patient data recording showing study time (s) on x-axis and AEP NLD anaesthesia-depth indicator values on y-axis.

AEP 6-(392.8 s); AEP 6+ (397.2 s), EEG peak 8 (779 s), AEP peak8 (779 s); AEP 8-(776.8 s) and AEP 8+ (781.2 s).

Figure 12:
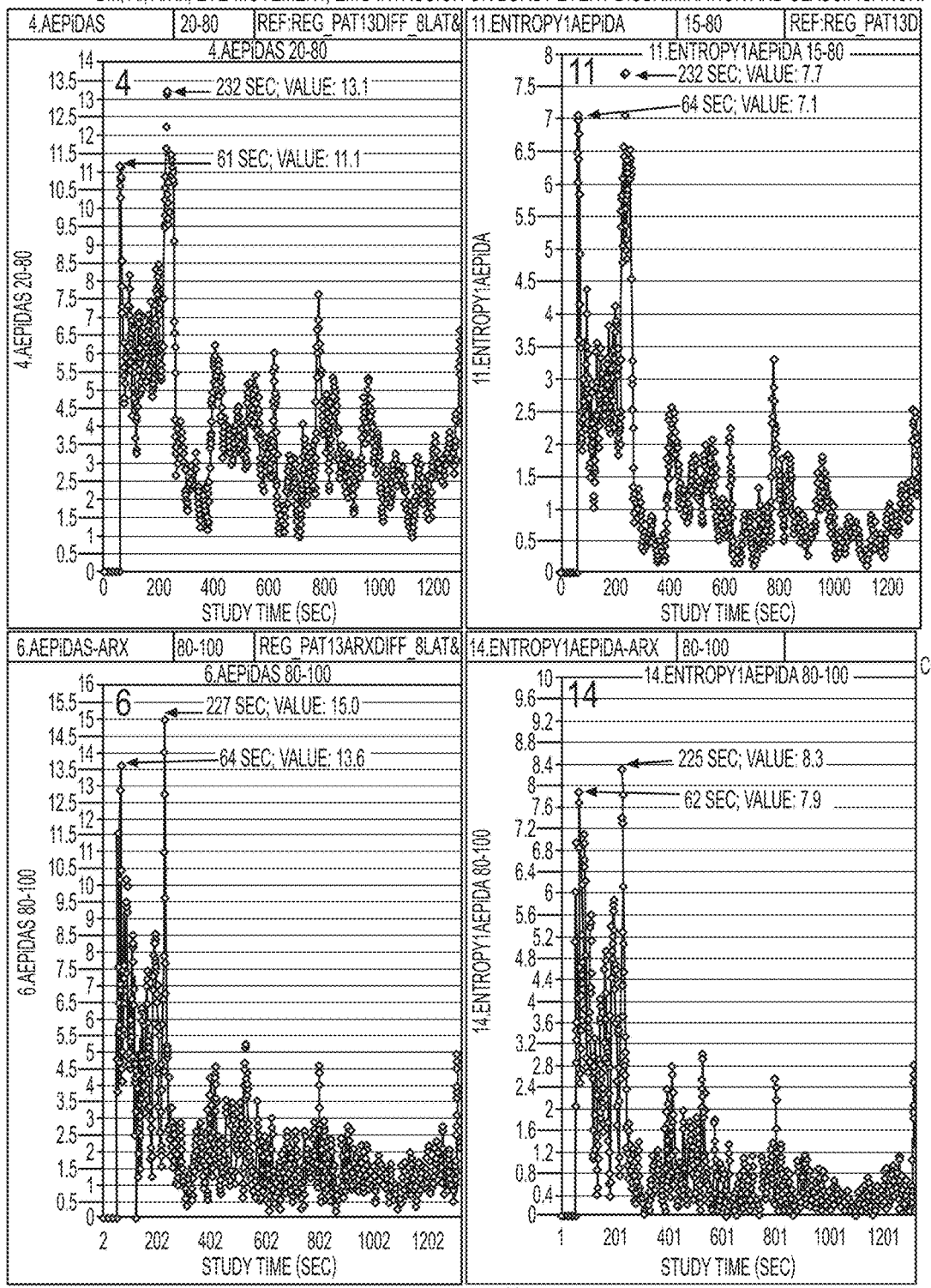
Figure 12:
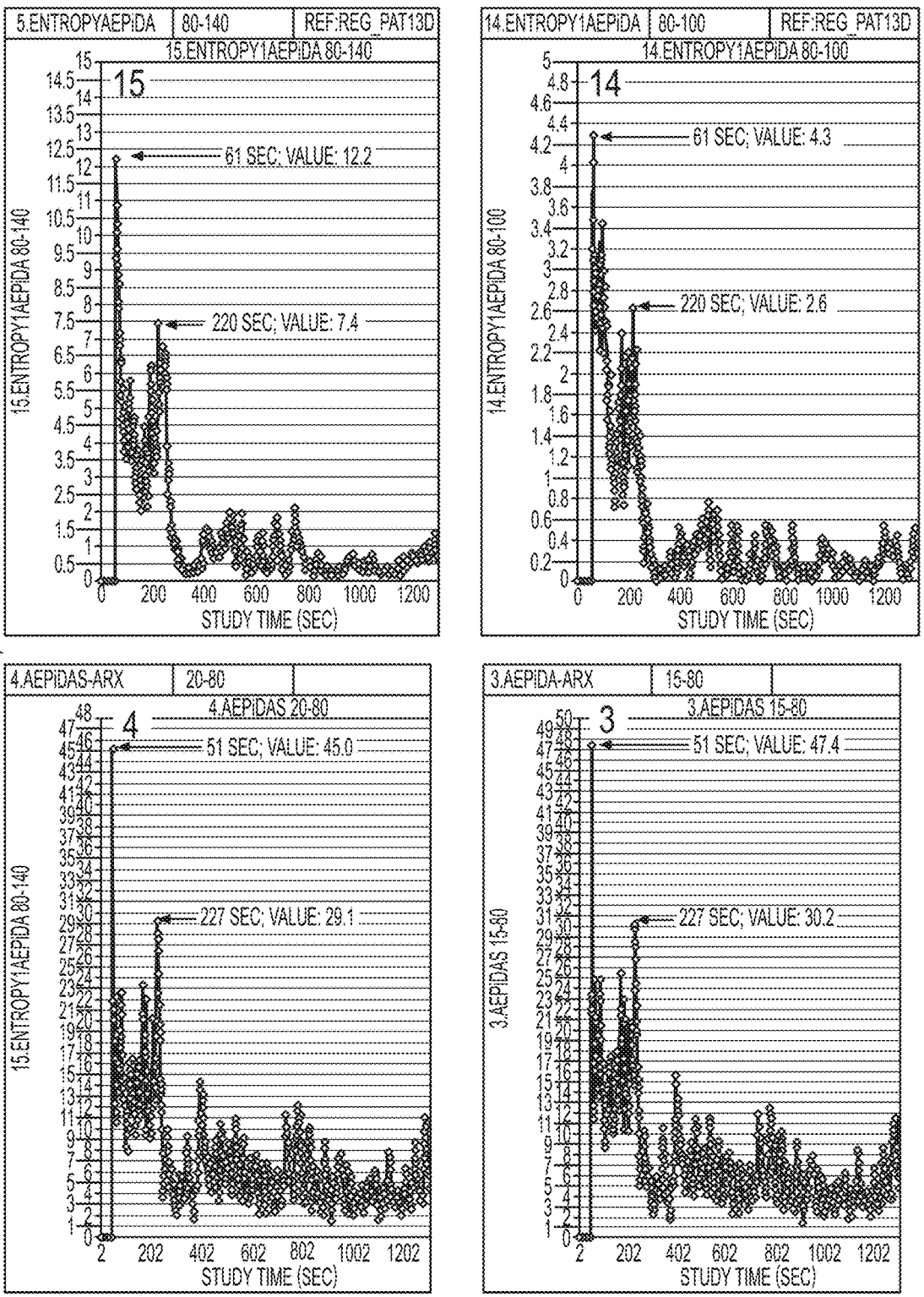

FIG. 12 Online event discrimination and delineation between any combination of CNS, PNS, MT, BM, Ar, ArNx, eye-movement, EMG intrusion or burst event discrimination and classification.

Figure 13:
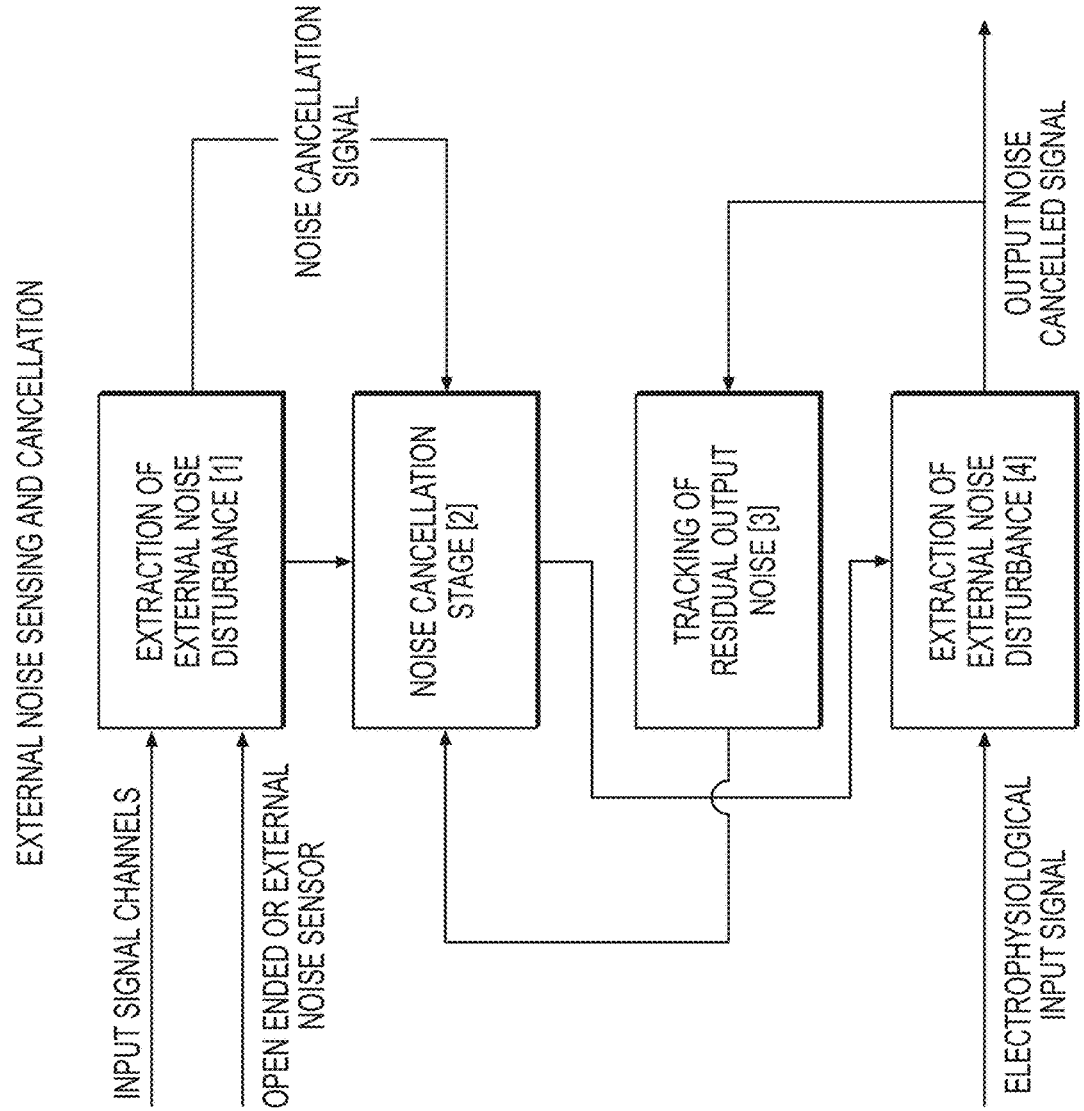

FIG. 13 External noise sensing and cancellation.

Figure 14:
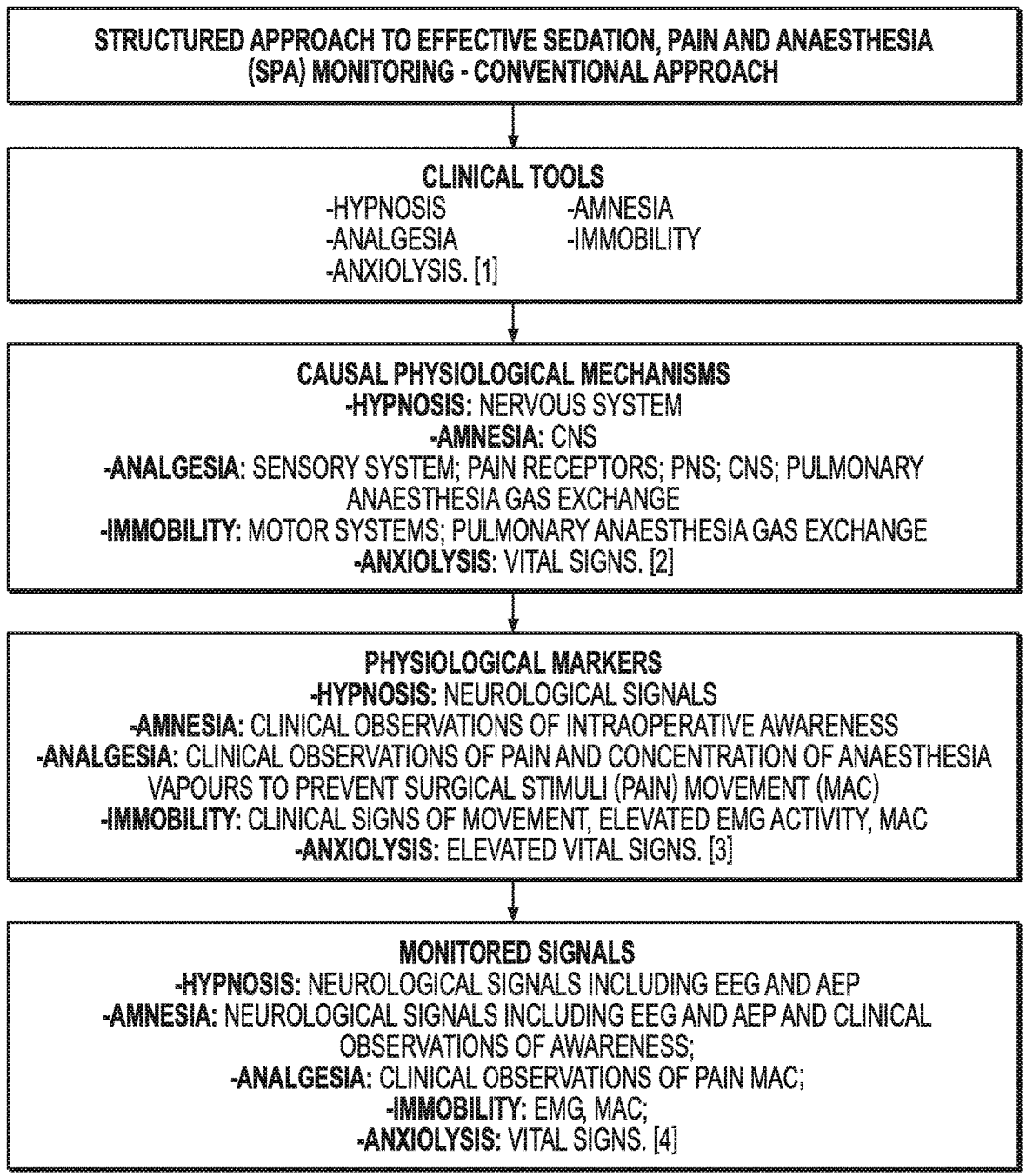

FIG. 14 Structured Approach to Effective Sedation, Pain and Anaesthesia (SPA) Monitoring-conventional approach.

FIG. 15 Structured Approach to Effective Sedation, Pain and Anaesthesia (SPA) Monitoring-contemporary approach.

Figure 16:
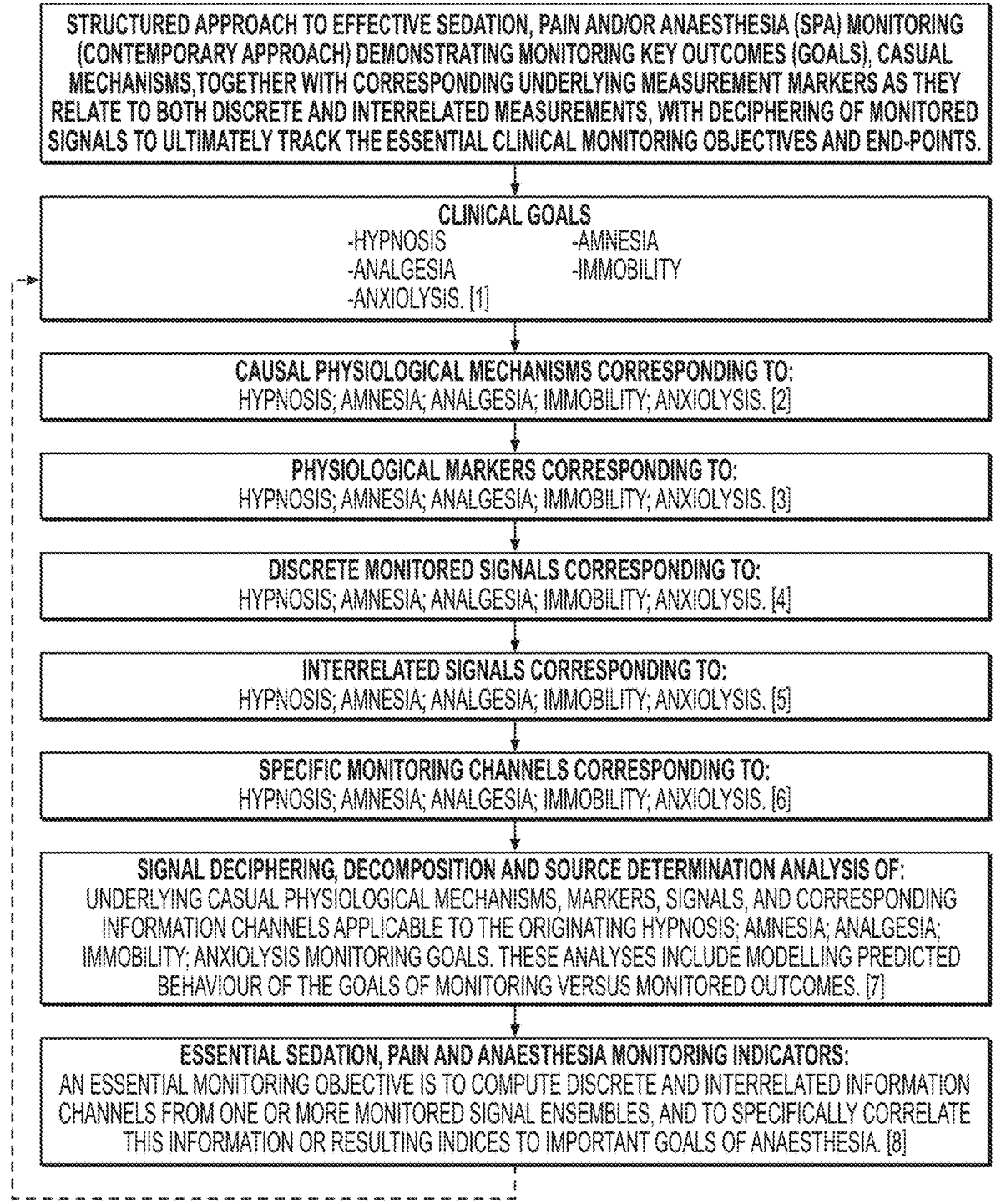

FIG. 16 Structured Approach to Effective Sedation, Pain and Anaesthesia (SPA) Monitoring-contemporary approach.

FIG. 17A STRUCTURED APPROACH TO SEDATION, PAIN AND/OR ANAESTHESIA MONITORING.

FIG. 18 Mapping of the principal A&CD functional measurement requirements applicable to direct and interactive anaesthetic effects.

FIG. 19 Summary of conventional and anaesthesia-specific events.

DETAILED DESCRIPTION

Figure 1:
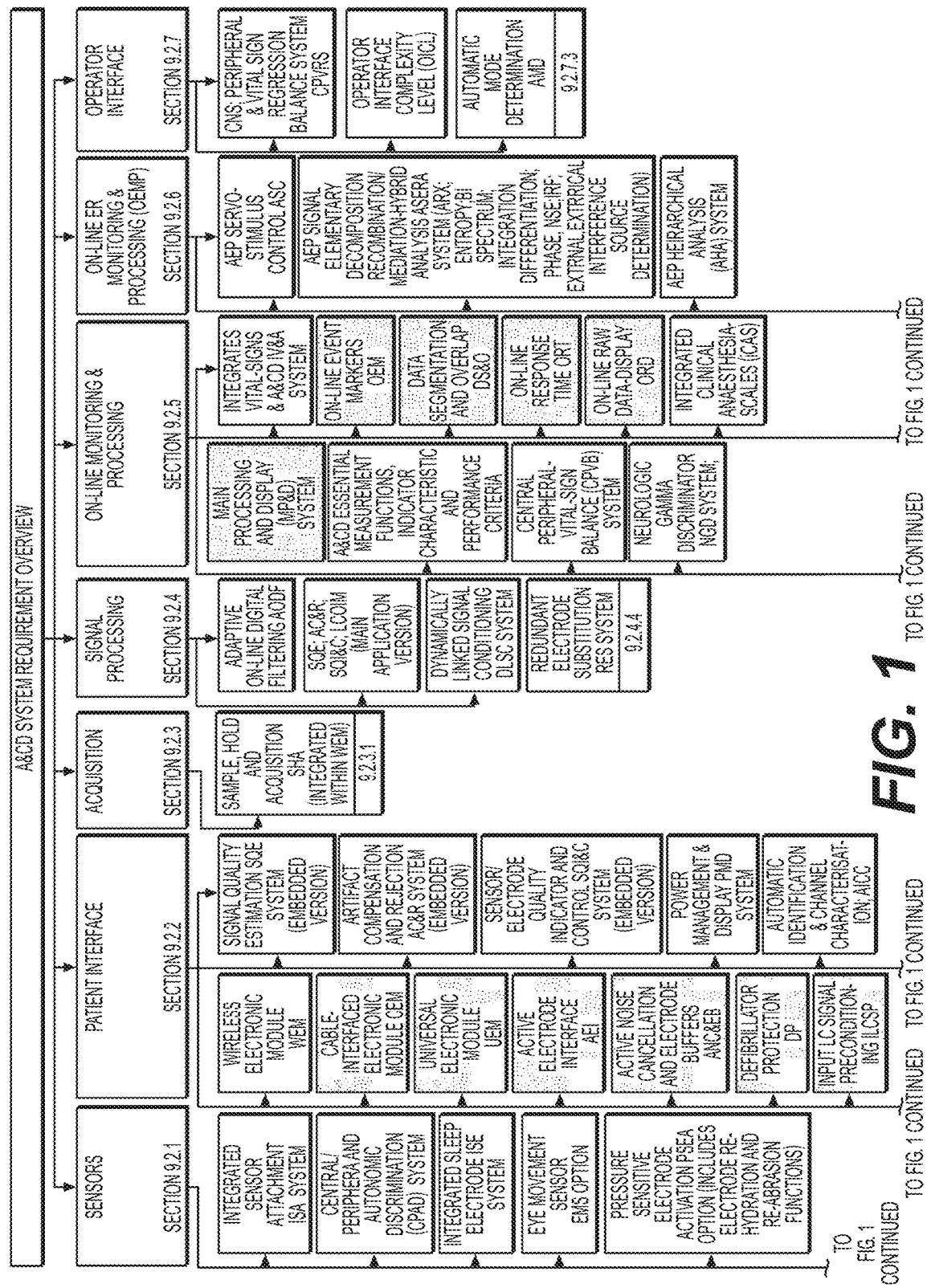
FIG. 1 A&CD system claim structure overview map with numbering of main claim groups.
Figure 1:
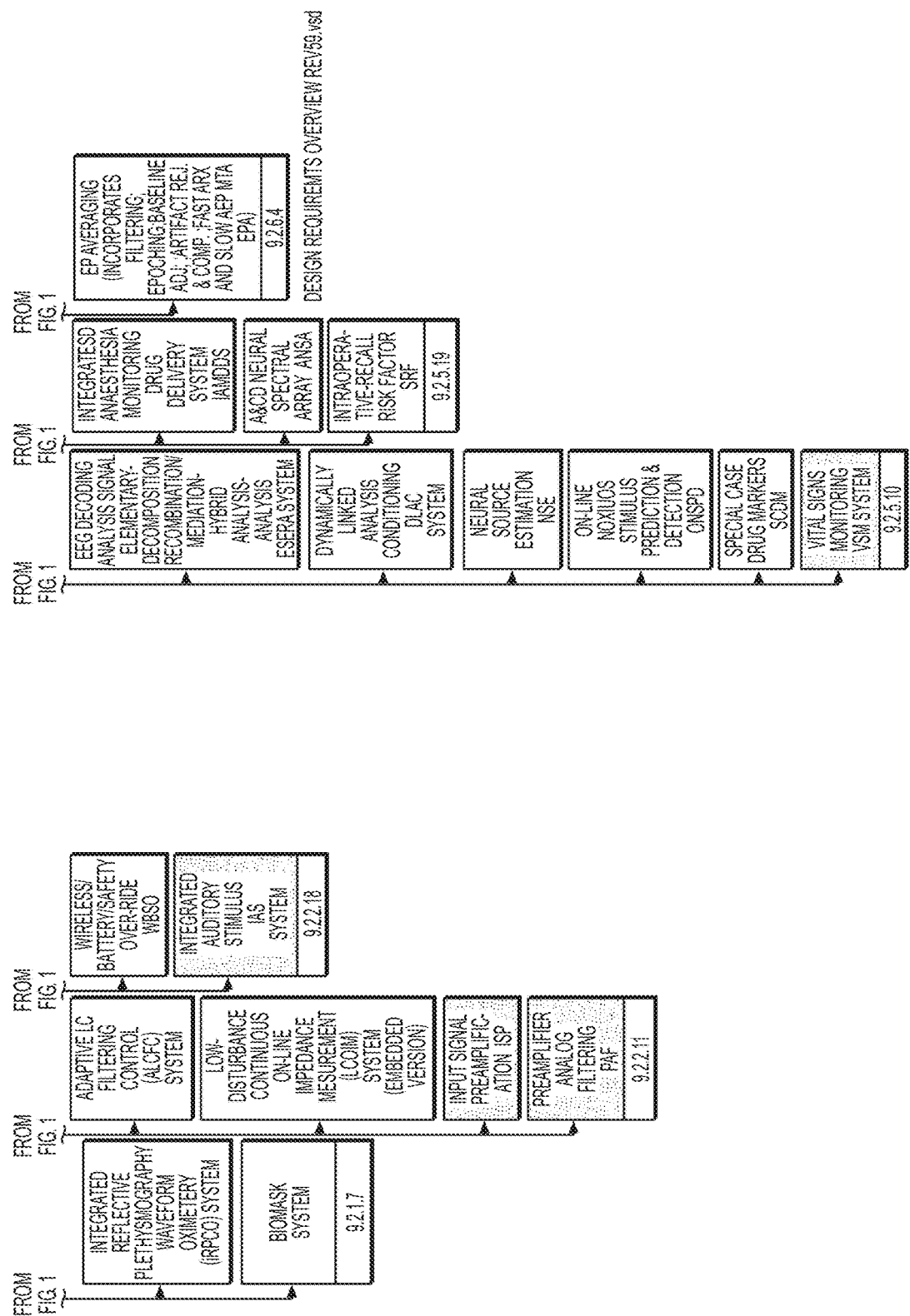

FIG. 1:

FIG. 1 decomposes the system into seven subsystems, each subsystem further decomposed into a number of components. Each of these subsystems and the affiliated components will be described in the form of systems requirements. Green blocks represent systems inventions.

Figure 2:
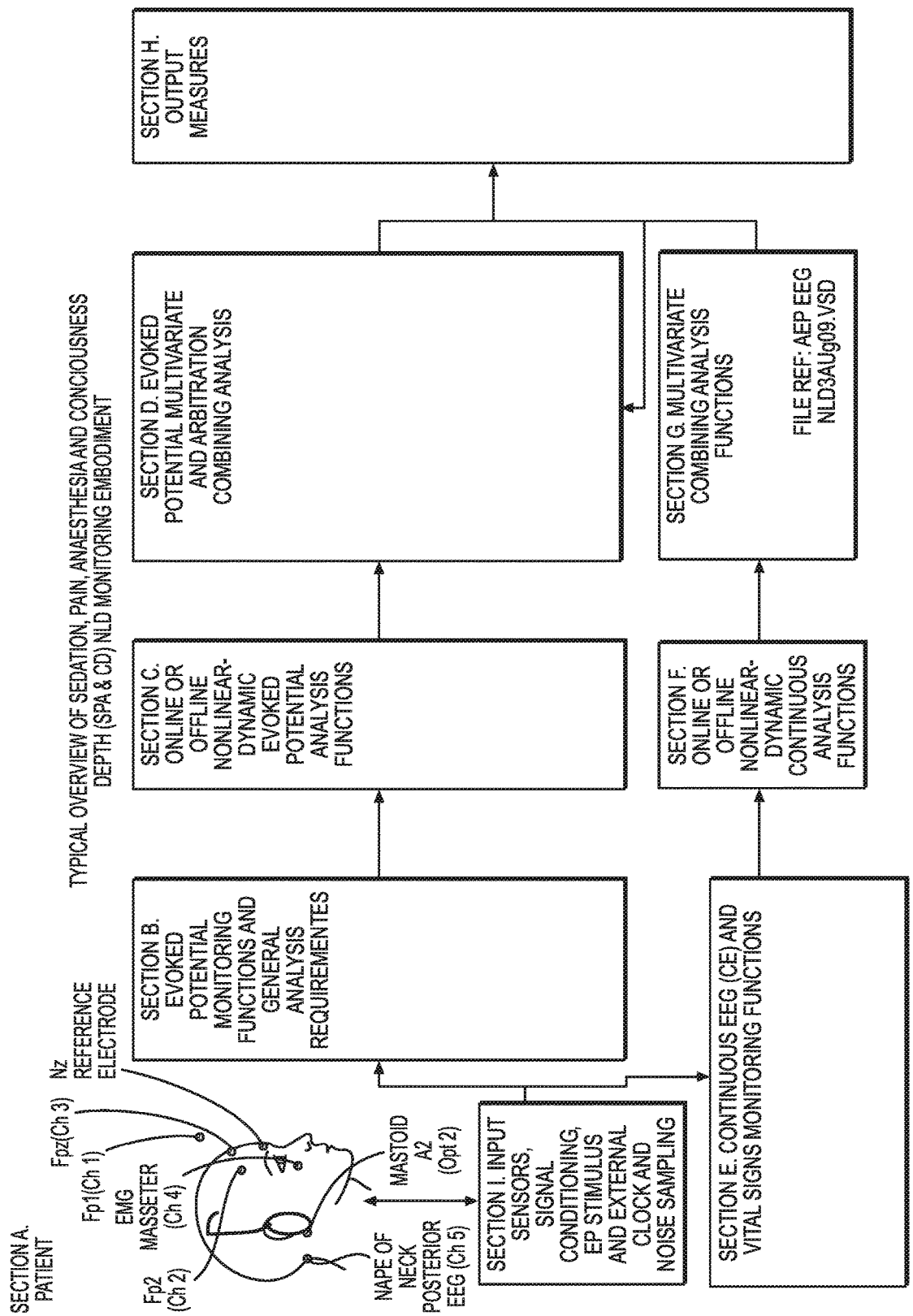
FIG. 2 A&CD system top level overview of sedation, pain, anaesthesia and consciousness depth monitoring system embodiment incorporating evoked and continuous non-linear dynamical biological signal analysis.

FIG. 2:

FIG. 2 presents a high level overview of a typical A&CD system embodiment. Section A shows the patient monitored signals via the patient-applied sensor or the so called integrated sensor attachment device, which is typically applied to the patients forehead and facial regions. A stimulus signal is generated and applied to the patient in order to evoked the desired patient-responses from further processing. The patient sensor-monitored signals are signal conditioned then input to section E where the evoked potential monitoring functions are applied to the evoked signals, and to section E where the continuously monitored signals are further processed. Section C applies special non-linear dynamical processing transforms to the evoked response signals, while section F applies non-linear dynamical processing transforms to the continuous physiological signals. The range of evoked potential analysis transform outcomes are then input to section D, which computes the evoked-potential combinational analysis so that section H can display the relevant corresponding system output measures.

The range of continuous signal analysis transform outcomes are then input to section G, which computes the continuous signal combinational analysis so that section H can display the relevant corresponding system output measures.

Figure 3:
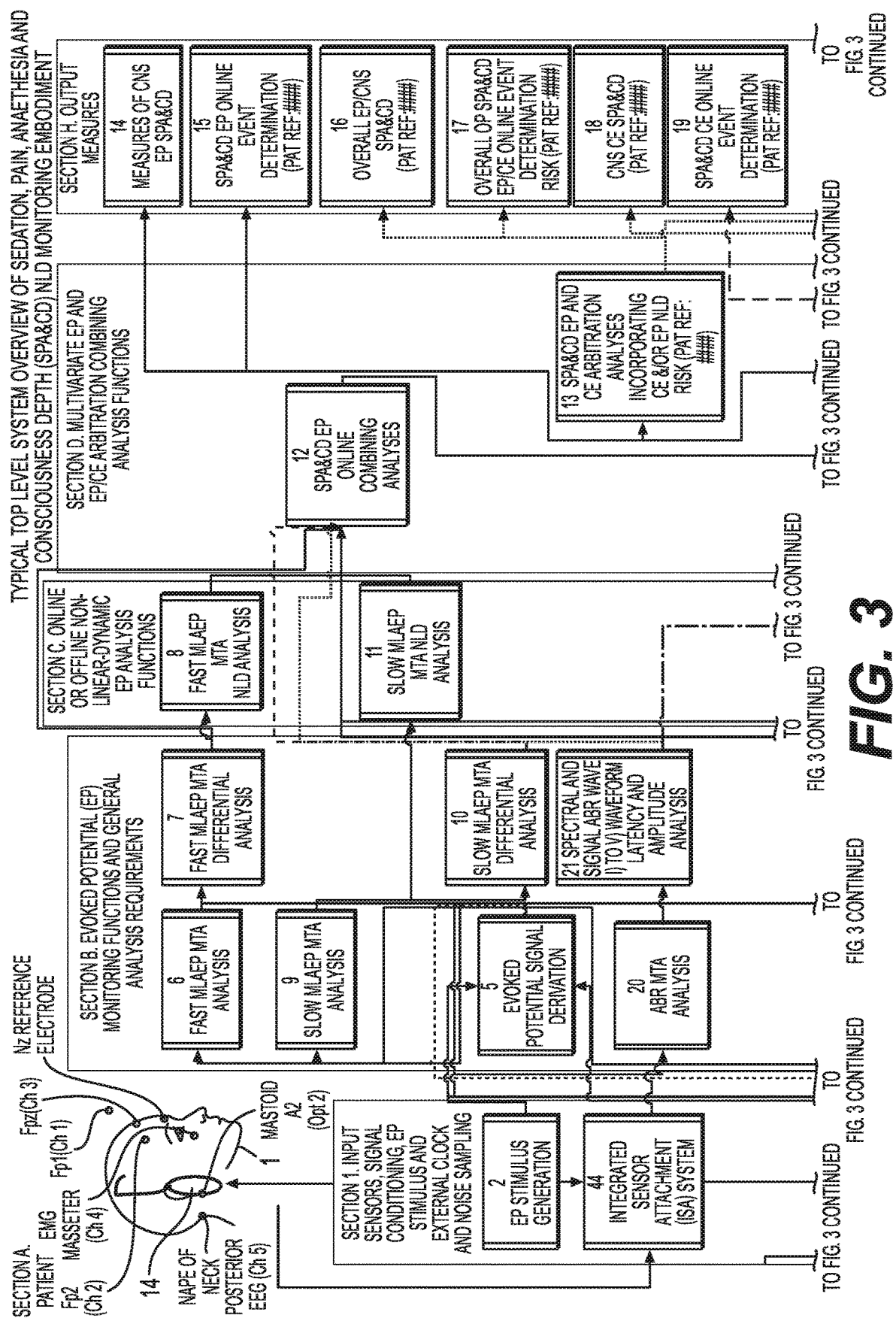
FIG. 3 FLOW DIAGRAM SYSTEM OF TYPICAL SEDATION/PAIN/ANAESTHESIA AND CONSCIOUSNESS DEPTH (SPA&CD) NLD MONITORING EMBODIMENT, AND INCOPORATING PRINCIPAL CLAIM GROUPS.
Figure 3:
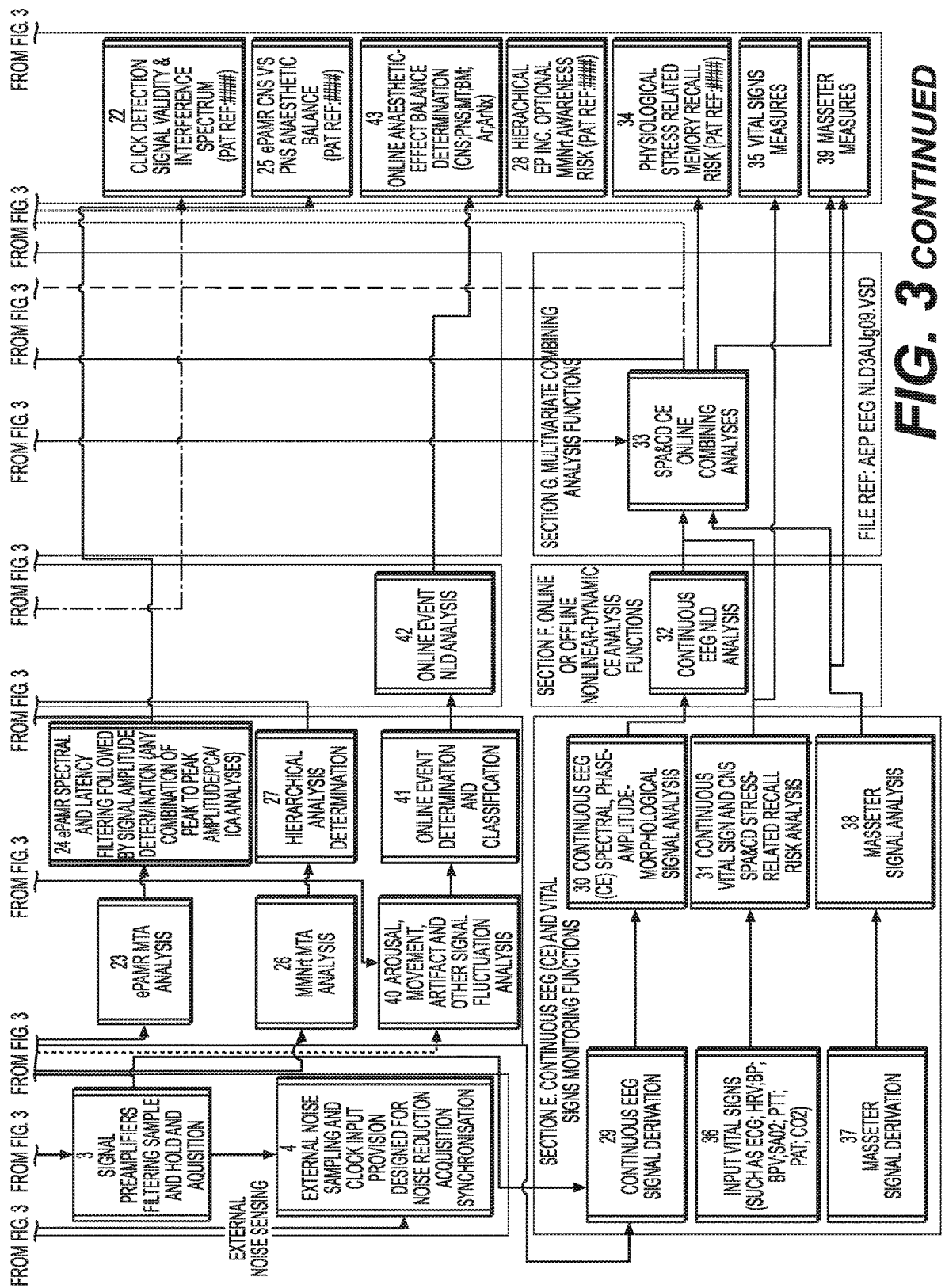

FIG. 3:

FIG. 3 presents a more detailed overview of a typical A&CD system overview.

The physiological parameters monitored from an individual FIG. 3; section A) undergoing both evoked potential (EP; section B) and continuous electroencephalography (CE; section E) monitoring are analysed online (real-time) or offline (section C) in order to compute a series of EP and CE derived non-linear dynamic (NLD) measures of pain/sedation/anaesthesia and consciousness depth (SPA&CD) during clinical or daily routines. These NLD parameters can be combined with (but not limited to) other classical or linear analysis outcomes as a means to compute a series of multivariate CE or processed parameters (section D; block 12); combined CE and EP parameters (section D; block 13) and/or CE multivariate output measures (section H). The output measures can be deployed as stand-alone SPA&CD indicators during clinical audiology, anaesthesia. ICU, sentient or cognitive state monitoring.

Section B shows EP functions and general analysis requirements including the EP stimulus generation function (section B; block 2) and signal preamplification, filtering, sample and hold and acquisition (section B; block 3). The external noise sampling and clock input provision designed for synchronised-acquisition noise-reduction (section B; block 4) described elsewhere in a separate document but in general enable external equipment clock signals and/or external noise sources to be sensed and acquisitioned by the SPA&CD monitoring system as a means to synchronise sample and hold functions in such a manner that signals sampling is 'interleaved' between peak interference periods. The sample-interleaving can be achieved by way of optimal synchronisation between external equipment and/or noise peaks monitored using specialised environmental noise monitoring sensors. Fast middle latency audio evoked potential (MLAEP) moving time average (MTA) derivations are derived (block 6) as a means to compute differential (block 7) and NLD (block 8) fast MTA outcomes. Similarly, slow MLAEP moving time average (MTA) derivations are derived (block 9) as a means to compute differential (block 10) and NLD (block 11) slow MTA outcomes. The differential and NLD fast MTA values are computed and input to the SPA&CD EP online combining analysis (block 12) which serves to compute a series of different combinational output measures which are in turn output as display indicators (section H) output and also combined with the CE multivariate (block 33) to produce a series of combined EP and CE SPA&CD measures (block 13).

Mediation Analysis Special Considerations:

The multivariate output values can be combined with special arbitration analysis which is designed to weight the influence of each input variable in accordance to a separate value as described in a separate document (reference existent patent application dealing with mediation analysis). In general the arbitration analysis can for example (but not limited to) adjust the weighting of the EP versus CE informational inputs according to a third parameter such as NLD parameters (but not limited to) whereby the NLD parameters (EP and or CE) may broadly indicate the anaesthesia depth phase (consciousness; light anaesthesia; deep anaesthesia) which in turn describes the probable relevance of the MLAEP weighting at any point in time. In particular, the deployment of CE NLD analysis (including different forms of spectral entropy, morphological entropy or type of complexity analysis) can provide an independent computational process less vulnerable to deep-anaesthesia signal instability than conventional MLAEP SNR analysis techniques in terms of mediating multivariate input variables derived from EP and CE signal sources. For example, in circumstances such as deep anaesthesia when MLAEP SNR is known to deteriorate the CE signal will likely be more dominant in terms of reliance upon the computation of SPA&CD indicator values. This type of system helps minimise the reliance upon MLAEP SNR outcomes at periods when even the MLAEP SNR computation is likely to produce erroneous outcomes given the unstable nature of MLAEP signals during deep anaesthesia [30; 31].

The auditory brain-stem response (ABR) MTA (block 20) and associated analysis (block 21) are designed to enable the tracking of ABR signal changes during sedation and anaesthesia. These output measures (block 22) can be more stable than MLAEP during deeper stages of anaesthesia or sedation and therefore can provide superior markers representative of stimulus presentation and AEP signal validity. The ABR functions are outlined in a separate document The evoked potential postauricular muscle (ePAMR) analysis (block 23) computes the signal activity across the early latency period (typically 0 to 28 ms) indicative of PAMR activity as a sensitive evoked measure of sedative or anaesthesia-induced muscle suppression. This analysis can take for form of (but not limited to) spectral and latency filtering, followed by signal amplitude determination (block 25) multivariate analysis (blocks 12 and 13) and output measures presented in block 25. The interconnection between CE ePAMR analysis (block 24) and multivariate analysis (block 33) highlights the important combinational analysis between conventional facial forehead signals, special masseter CE EMG derivation and ePAMR EMG signal determination (blocks 23 and 24) are designed to compute spectral and morphological latency/amplitude tracking of changes during sedation or anaesthesia.

The mismatched negativity real-time (MMNrt) MTA (block 26), associated hierarchical analysis functions (block 27) and output measures (block 28) in general provide a means to disassemble the composite AEP signal into the different functional information channels representative of the lower level ABR sensory responses, the N1 markers indicative of the arrival of the stimulus through the cochlear and auditory nerves to the cerebral cortex (such as N1 presence), the afferent neural responses (such as N1-effect), elevated N1-P2 amplitudes corresponding to increased refractory period (inter-stimulus interval; ISI), MLAEP amplitude-latency changes with deeper anaesthesia, through to the processing contingent potentials (PCP) indicative of the higher order attention states indicative of the laying down of longer term memories implicated during intraoperative recall. These hierarchical analysis function functions are outlined in a separate document.

The block 36 input vital signs, the continuous vital sign and central nervous system (CNS) SPA&CD stress-related risk analysis (block 31) and associated output measures (block 35) typically derive their signal input information from a special integrated sensor attachment (ISA) system. The SPA&CD system incorporates vital sign parameters (pulse rate, respiratory rate, body temperature, and blood pressure) as integral online monitoring functions. In general the vital sign monitoring (per VSM, above) can track patient vital signs (pulse rate, respiratory rate, body temperature, and blood pressure), hemodynamic functions (circulatory measures such as PTT subcortical arousals) and autonomic measures (peripheral nervous system homeostasis functions such as HRV) relevant to anaesthesia. Additionally, the VSM functionality includes the provision to derive a range of vital sign measures based the monitoring functions of the integrated sensor attachment (refer also ISA), integrated reflective plethysmography-waveform oximetry (refer also IRPO) and these measures support the derivation of intraoperative recall factor (refer also IRf). The vital sign functions can be individually displayed as presented in various integrated forms. The ISA system and the IRf system are detailed in separate documents.

The masseter derivation (block 37) is typically derived form the special IAS system. The masseter analysis (block 38) and associated output measures (block 39) can augment the ePAMR analysis as described above and similar to these measures enable sensitive and accurate continuous tracking of the patient's EMG activity. The masseter derivation of EMG level during SPA&CD monitoring are detailed in a separate document.

Block 40 processes the EP (block 6), fast MTA (block 6) and slow MTA (block 9) inputs in order to detect and delineate important online events such as body movements (BM), movement time (MT), arousals, anaesthesia-specific arousals such as noxious stimuli (ArNx), background physiological events such as eye movements; EMG bursts; or EMG intrusion in general, artifact and other signal fluctuation which could be relevant to SPA&CD or reversal. Additionally, the distinctive central nervous system versus peripheral nervous systems signal sources are identified. Block 41 classifies these online events and signals sources, while block 42 applies EP NLD analysis processing as a means to enhance discrimination between different physiological signal sources and online events. Block 43 provides both discrete targets of anaesthesia (such as hypnosis, analgesia, amnesia, immobility, anxiolysis) and combined measures of anaesthetic balance in a form suitable to provide the clinician optimal dosage guidance and patient state information at any point in time, as further outlined in FIG. 14-19.

FIG. 3, Block 44 presents the integrated sensor attachment (ISA) system as further outlined in FIGS. 18 and 19 incorporating a range of embedded sensors to monitor peripheral, central and vital sign signals was established. These requirements included integrated oximetry and associated output products including plethysmography waveform, pulse transit time (PTT), pulse arterial tone (PAT), heart rate variability (HRV), heart rate HR, subcortical (autonomic) arousals (sAr), along with associated blood-pressure derivatives. The provision for airflow monitoring as an integral ISA function was formulated as a means to enable online respiration measurements. The monitoring of these parameters coupled with masseter and PAMR (EMG) activity, EEG and AEP neurophysiological parameters, and ECG signals derived from these signals, were described as a means to accommodate the essential measures relevant to A&CD monitoring. Additionally, ISA system requirements included onboard signal quality indicators, embedded pressure-activated cells capable of regelling and re-abrading electrode connections, and "concertina-type" size-adjustment functionality. Special requirements included intuitive light emitting diode (LED) indicators capable of localised-sensor quality status indication.

Figure 4:
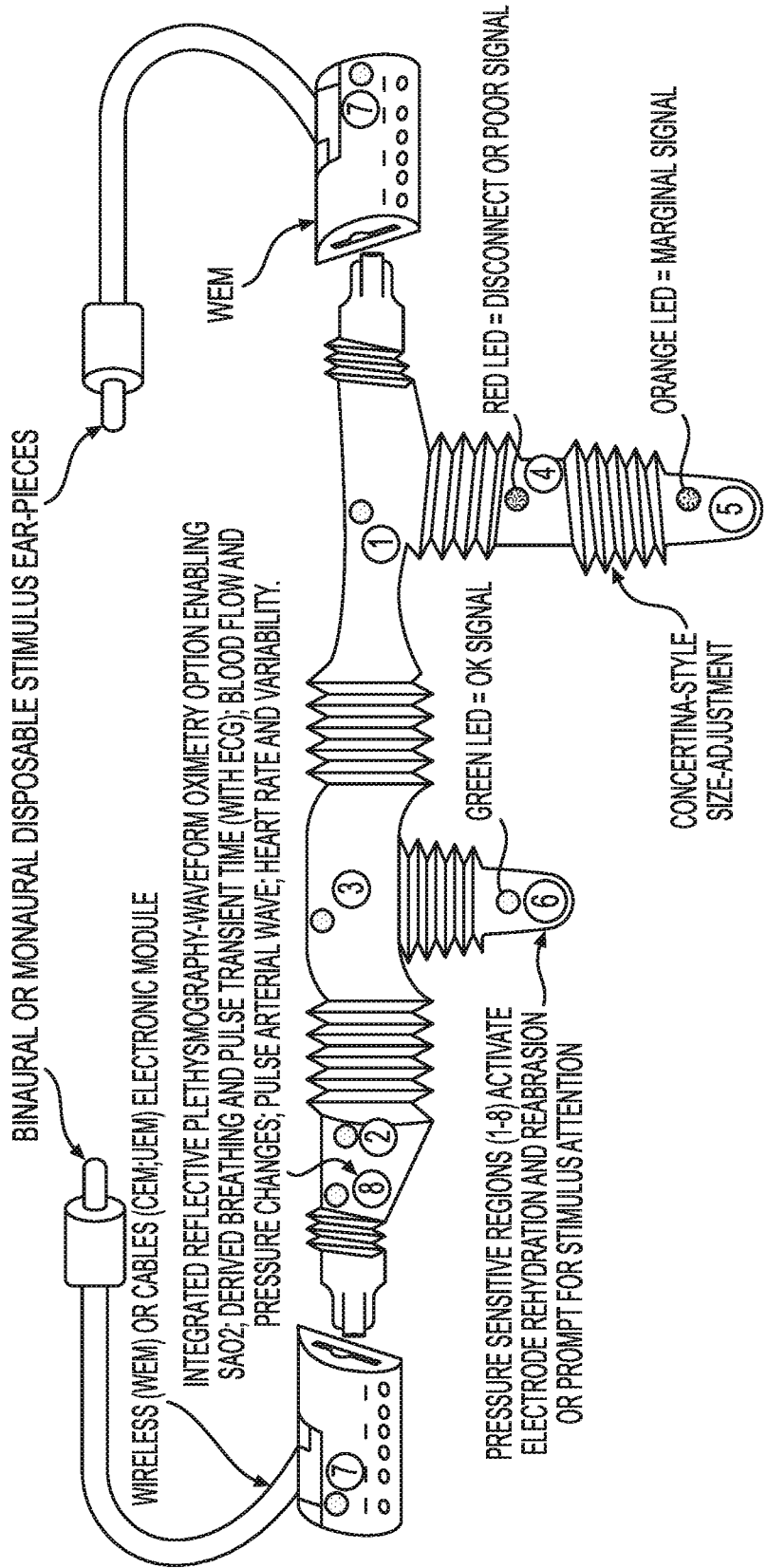
FIG. 4 Integrated sensor attachment (ISA) system with signals quality indicators. The illustration presents the ISA system encompassing reflective oximeter (8); embedded electrophysiological electrodes with re-hydration and abrasion pressure pad functions (1-6); stimulus (7) and integrated oximeter (8), and LED quality status indicators.

FIG. 4:

FIG. 4 presents the integrated sensor attachment (ISA) system with signals quality indicators, with markers highlighting the integrated reflective oximeter (8); embedded electrophysiological electrodes with re-hydration and abrasion pressure pad functions (1-6); stimulus (7) and integrated oximeter (8), and LED quality status indicators. The ISA system comprises of a low-cost, diposable patient-applied part encompassing anaesthesia-specific and appropriately placed EEG/AEP, EMG and vital sign sensors, integral signal quality management systems, and provisions for airflow monitoring, as outlined here.

From a construction perspective the ISA incorporates a single-substrate flexible membrane capable of conforming to a wide range of different facial profiles, in order to prevent buckling and gaps which can deteriorate the crucial electrode to skin contact impedance or connection status. A series of quality control LEDS (functions described below) need to be located near each of the monitoring sensors, along with a series of embedded electrode-gel pressure-pad cells (functions described below). The design of the ISA interface connector is extremely important and allow highly reliable user-friendly interconnectivity. Guidelines and standards relating to these disposable devices are important consideration, particularly in the context of environmental standards controlling disposable material and recycling requirements.

A special "concertina-style" or other type of retractable or expandable size-adjustment element enables a limited range of ISA sizes to be configured to the demand of the wider population.

The ISA electrode placements are critical and accommodate the monitoring requirements relevant to electrode registrations outlined in In particular the standard range of ISA sensors accommodate both hybrid (EEG/AEP) and EEG-based configurations. A hybrid advanced configuration (see FIG. 4-5) incorporating additional electrodes such as Iz (posterior EEG), facilitate special analysis functions such as EEG neural source estimation (NSE; described below) [32].

The ISA system incorporates LED indicators which indicate the signal status computed by the signal quality estimation (SQE) and corresponding indicator and control systems (SQI&C; requirements outlined below). The ISA LED indicators intuitively alert the user of the sensor signal quality and connection status whereby (for example) green LED illumination could signify acceptable quality, orange for marginal and red for failure or disconnection status. The ISA system is presented below in FIG. 4, while an illustration of the UEM with integrated signal quality LEDS is presented in FIG. 5.

The provision for an integrated reflective plethysmography-waveform oximetry (IRPO) system (described below) enable vital sign monitoring as an integral ISA function.

The provision for an optional airflow sensor using thermosensitive material such as (but not limited to) thermocoupler, thermistor or PVDF materials for the more specialised and more advanced ISA versions.

One embodiment of the disposable ISA system includes a backup battery which is designed to be activated when opening the secured and sealed ISA packaging. This feature enables a degree of battery life predictability based on the packaging use-by-date information as introduced in the related background intellectual property publications [7].

The integrated sensor attachment (ISA) system originated as part of the related background IP publications [7; 8].

The AEP stimulus can be included as part of the electronic interface module (UIM; WEM), incorporated as a small speaker driver as part for the ISA substrate, or alternatively be included as a wireless earpiece or headphone system. In the case of the wireless earpiece option up to 2 earpieces can be provided. Each earpiece can comprise of two separable parts consisting of a reusable and a disposable element. The disposable element can include the patient-applied parts which are subject to cross-infection risk where reuse is deployed. Furthermore, in one embodiment the battery, which can be a disposable or rechargeable part, can be interconnected with the disposable earpiece section so that operation is simplified by attaching the disposable and reusable parts at the start of monitoring and then disposing of the disposable parts at the end of monitoring. For example, a low cost silicon earpiece could be attached to a miniature electronic wireless stimulus module to enable quick attachment, minimal obtrusion but reliable operation.

The UEM, WEM and CEM incorporate similar functionality except for the cable versus wireless interface connectivity options as the naming convention suggest. The UEM term can be substituted for WEM or CEM in the following text, except where specific reference to interconnectivity and power functions apply. UEM functions include signal pre-amplification and filtering, data acquisition, digital filtering, signal quality management functions, stimulus generation, and battery and wireless management functions outlined here.

A quick-connect and release system enables reliable and user-friendly interconnection with the ISA and UEM.

While the ISA is designed to be a low-cost disposable device, the patient interface electronic module is designed to be a reusable system and contains more expensive electronics circuitry.

Cable connection can be deployed at anytime without disrupting monitoring, enabling a convenient and high-dependent monitoring backup provision for circumstances where battery recharging or wireless interference a concern.

Figure 5:
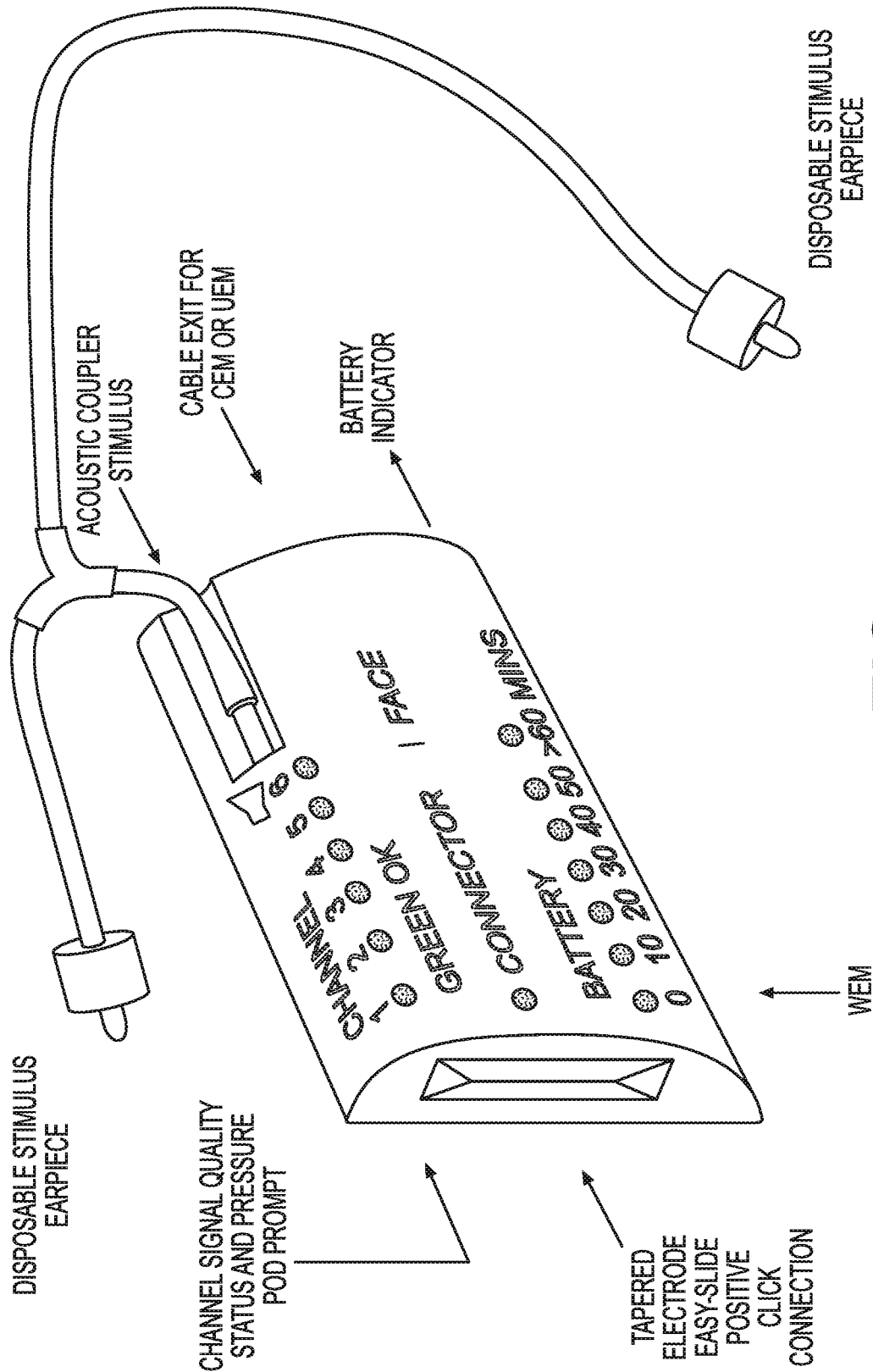
FIG. 5 Conceptual overview of UEM module incorporating (LHS panel) binaural stimulus "Y" adaptor acoustic-coupler circuit, electrode assembly connection status, battery display indicator, signal quality status and user prompt indicators (5; 6).

The UEM enables stereo or monaural stimulus operation using "Y-junction" interface adaptor as shown in FIG. 5. The UEM acoustic coupling function can be combined with provision for disposable ear-pieces and interconnecting tubing, to mitigate patient cross-infection risks.

The following FIG. 5 presents a conceptual overview of the UEM module incorporating stimulus acoustic-coupler, IAS connection status indicator, battery display indicator signal quality status and user prompt indicators.

Figure 6:
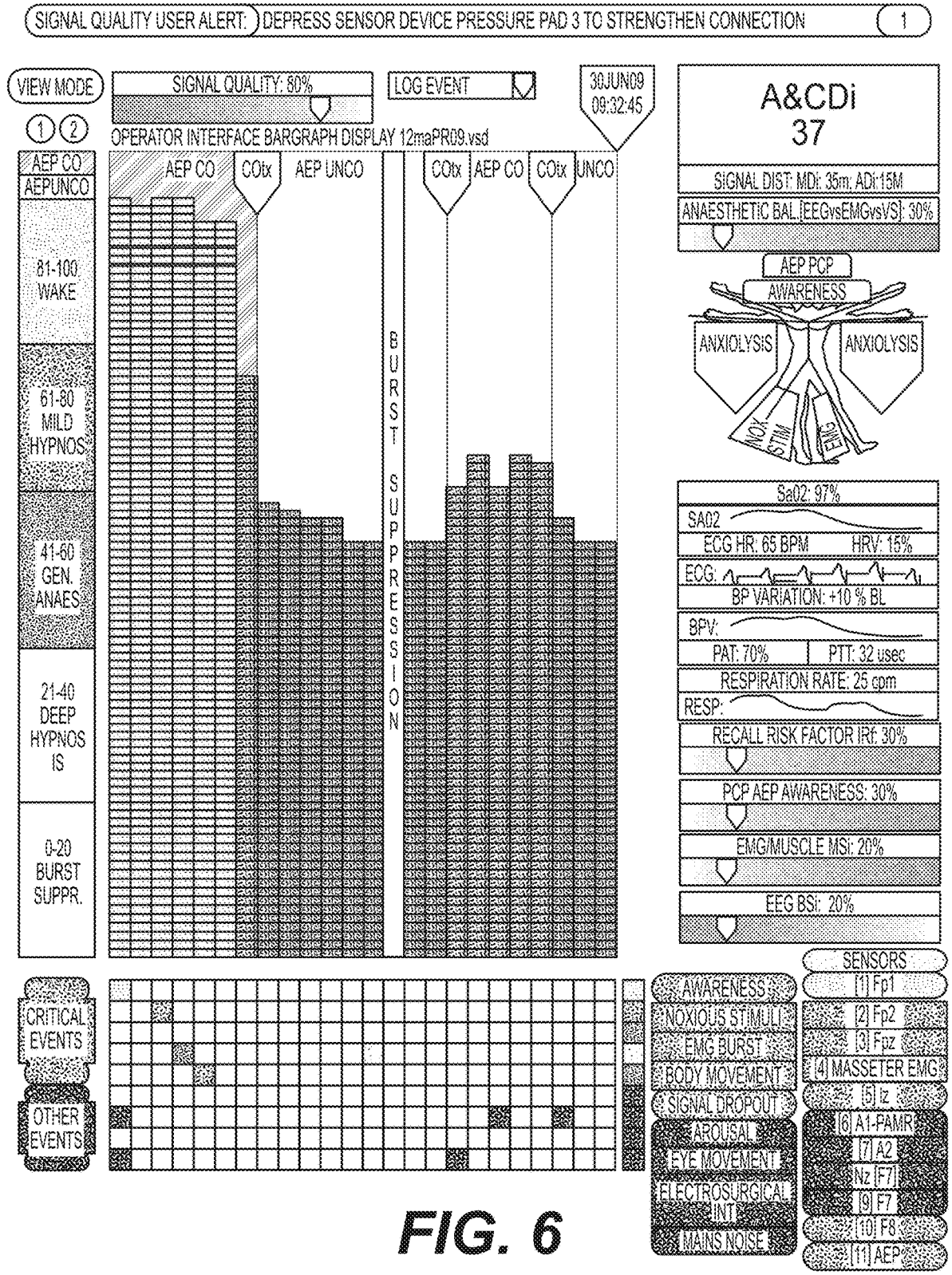
FIG. 6 Main system diagnostic-mode graphic user interface.
Figure 7:
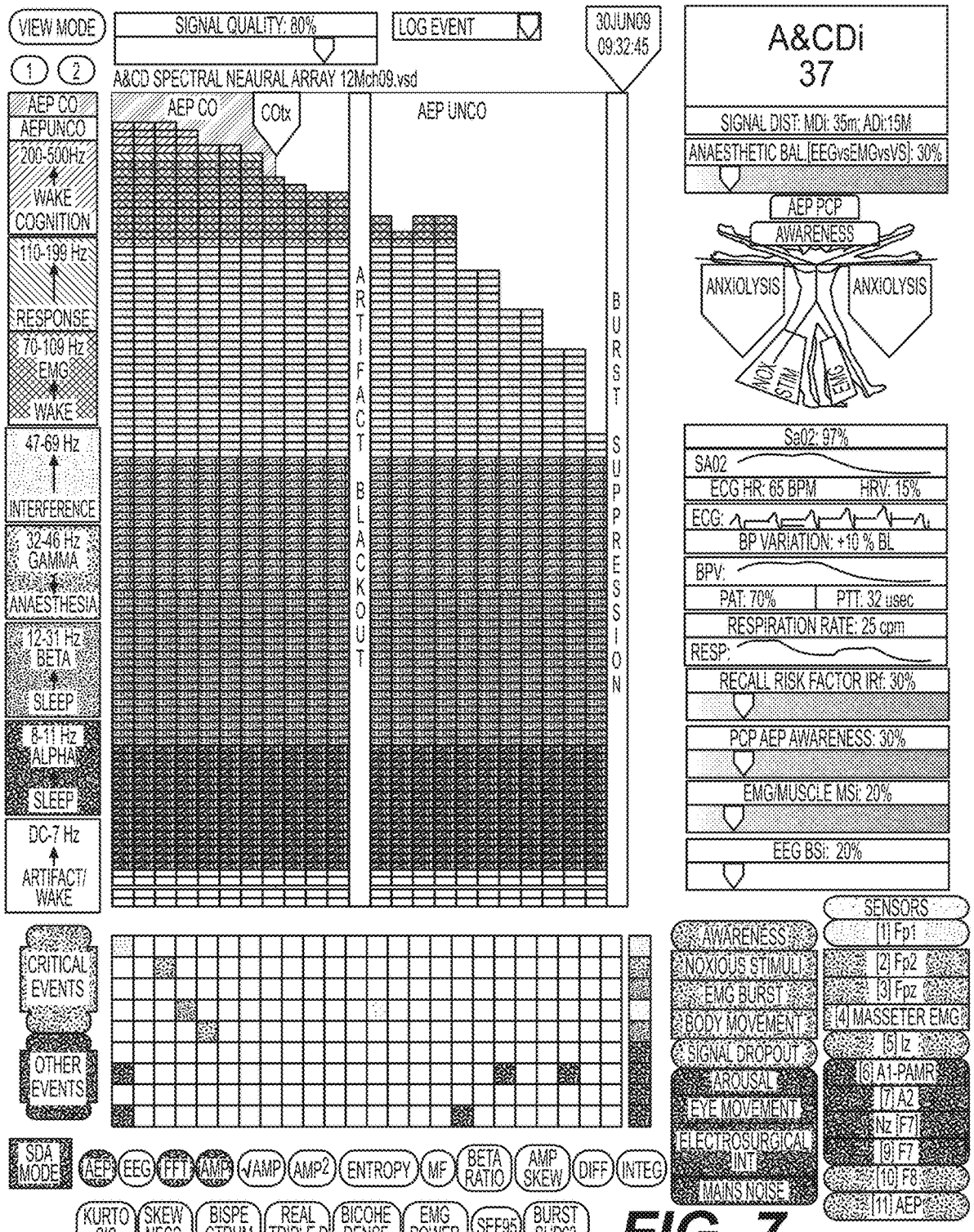
FIG. 7 The Neural spectral display (NSD) presented as function of the A&CD display (A&CDD) system with frequency histogram.

FIG. 6:

FIG. 6 and FIG. 7 share similar elements except that FIG. 7 provides a more comprehensive diagnostic mode of monitoring whereby the main display area can be assigned to display many additional analysis functions, as depicted by the row of display selections at the base of the main screen display area.

FIG. 7:

FIG. 7 presents an extended display mode referred to as the neural spectral display (NSD) and provides a number of special display tools designed to examine various events, special-case monitoring periods and other display views relevant to more detailed monitoring.

The NSA and the A&CDD functions as a useful tool for the investigation of anaesthesia monitoring as outlined here.

The A&CD system is configured to enable the computation, recording of and display of a range of analysis histogram outcomes including frequency/FFT amplitude and power, bisprectum and related output products, and non-linear dynamic analysis (entropy), as illustrated in the selection options presented in the lower panel of FIG. 7.

Online histogram display indication together with corresponding reports present information in a graphic or tabular format.

One example of an important display mode is the need for a spectral display whereby relevant anaesthesia spectral parameters such as the spectral band of DC to 8 Hz (increases during alertness [21] wake activity and opioid usage [23]), alpha and beta bands (increase during wake), gamma (increases during anaesthesia).

AEP (including ABR) and EEG spectral displays distinguish 50, 100, 150, 60, 120 and 180 Hz mains-cycle frequencies are presented.

The NSA display format is available for all physical or derived channels including output noise control and stimulus audio channels.

The NSA spectral display accommodates DC to 8 Hz delta and theta bands region which are believed to be representative of alertness [21] or artifact regions such as arousals and eye movements [23], 8 to 12 Hz alpha and 16 to 32 beta band regions which are believed to be markers of anaesthesia depth [23] and sleep states [14], 30 to 47 Hz regions believed to be markers of gamma [10; 28], 70 Hz to 110 Hz EMG spectrum [2], 11 to 210 Hz, and 201 to 500 Hz as a marker of cognitive function and/or capacity [21].

The NSA system as presented in FIG. 7 displays a power distribution histogram. The percentage of the total power (100%) for each of the spectral bands relevant to A&CD determination is displayed for each consecutive or 1 s overlapped 8 s interval. The spectral bands are decomposed into frequencies ranging from DC (white) to 500 Hz (red), as outlined in the scale presented in the left section of the display panel. The upper right section of the diagram displays the overall integrated A&CDi representative of a summary anaesthesia depth indication, while the lower bargraph and corresponding meter display representative (top to bottom of panel) of other relevant factors including EMG muscle suppression index (MSi). EEG burst-suppression index (EEG BSi), intraoperative-recall risk factor (IRf), signal quality factor (SQf) and cerebral silence factor (CSf).

Fast consciousness transitional detection status, together with crucial artifact signal drop out and burst suppression periods can be displayed concurrently with slower moving histogram bargraph changes, by way of a background colour change and corresponding alerts as demonstrated in FIG. 7, where the consciousness transitions (COtx) and burst suppression periods are clearly indicated.

The lower panel of FIG. 7 presented here demonstrates a series of screen-buttons representative of sample range of physiological variables and analysis parameter selections available for the online NSA and A&CDD investigator mode.

Figure 8:
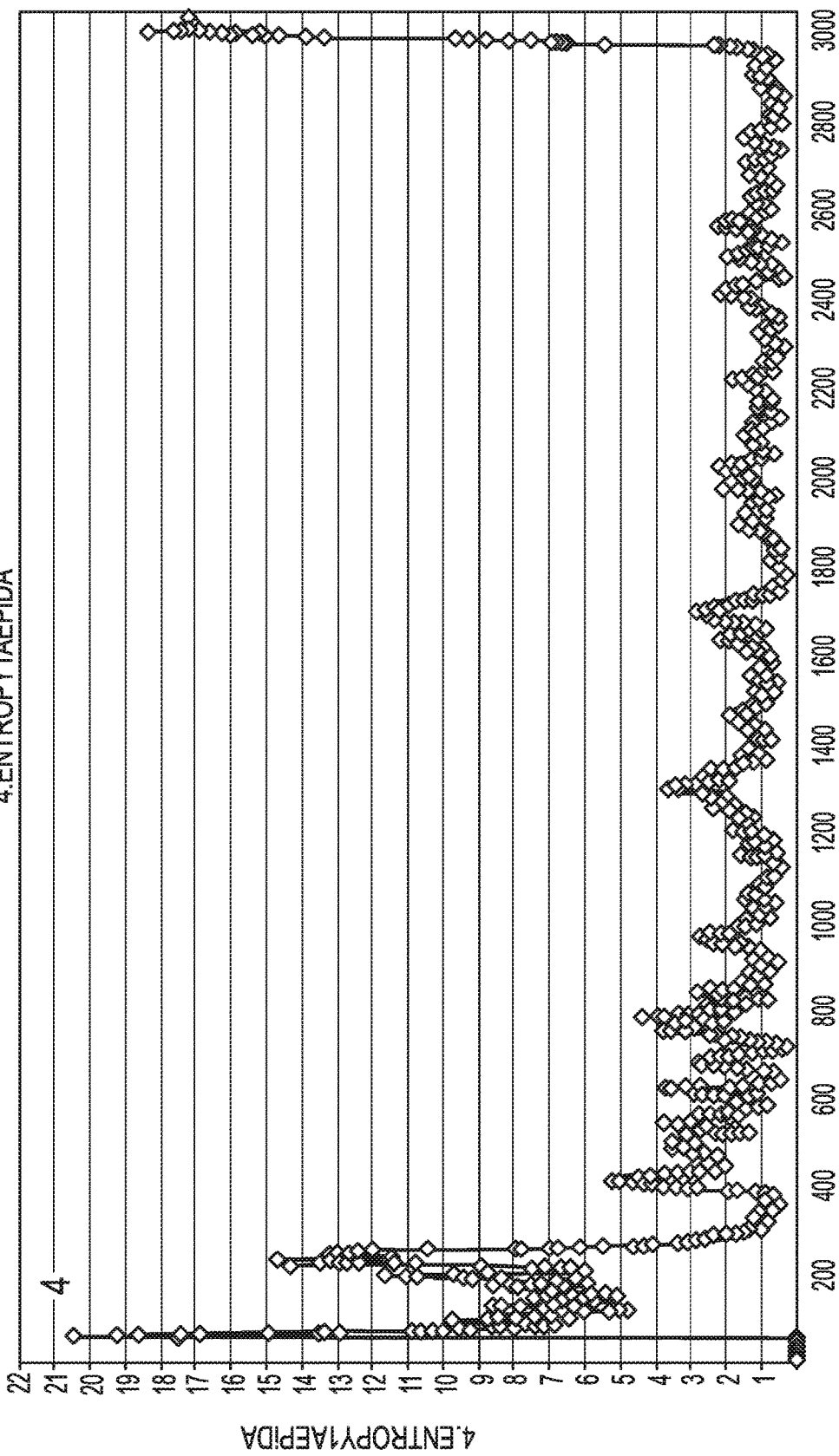
Figure 9:
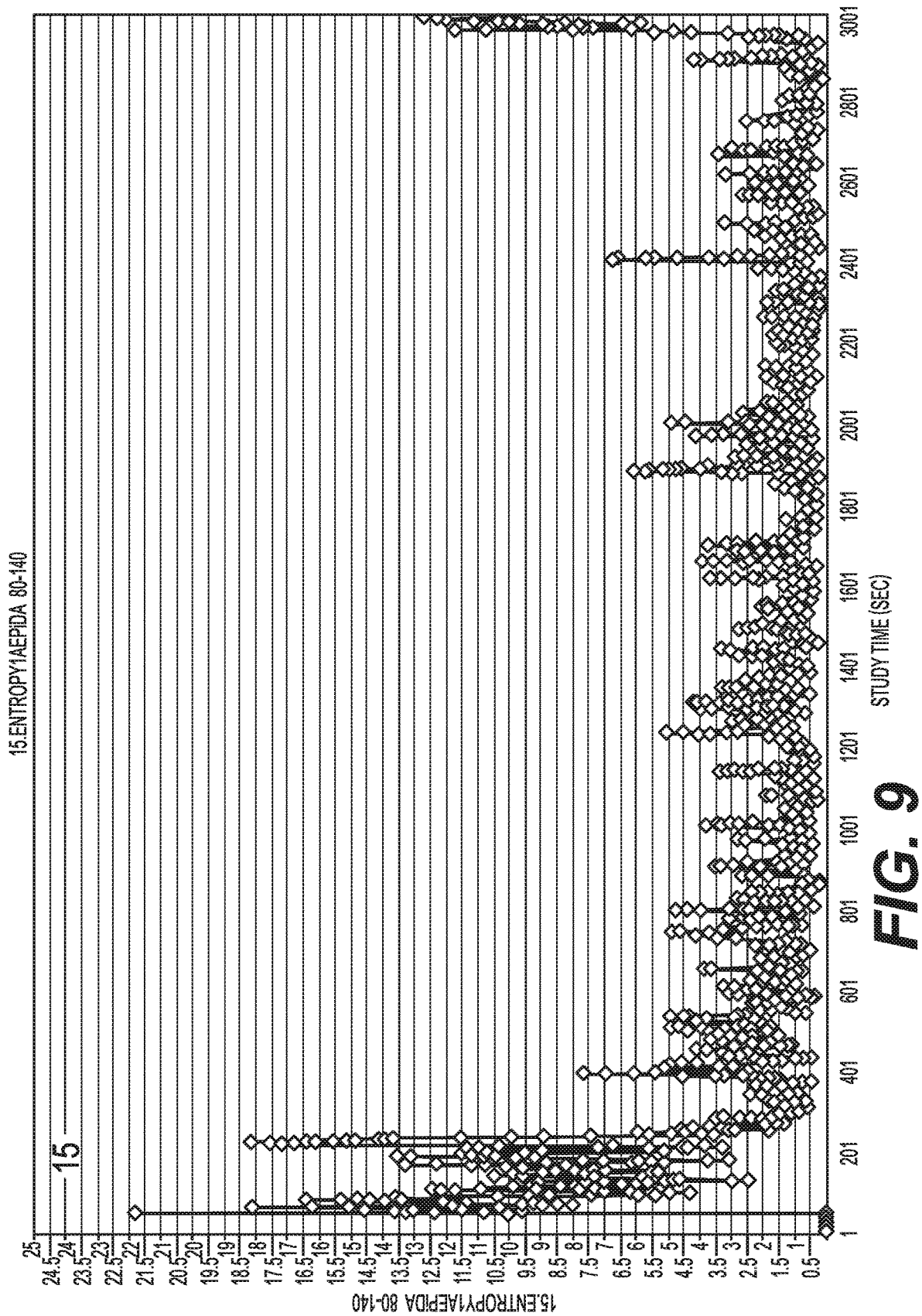

FIG. 8:

FIG. 8 presents 256-sweep AEP averages plotted from anaesthetised surgical patient data recording showing study time (s) on x-axis and AEP NLD anaesthesia-depth indicator values on y-axis. This example data plot demonstrates the value of applying non-linear dynamical analysis processes to evoked-response signals and combining these processes with the unique latency-interval analysis processes. Additionally, the sample plot demonstrates in this case the use of differential amplitude analysis techniques used in conjunction with the non-linear dynamical auditory evoked potential (AEP) and AEP time-interval dependent processes. The non-linear dynamic process can include entropy, spectral entropy, time-series complexity-analysis, time series spectral complexity analysis or other variants of the non-linear dynamic transformation. Additionally, the other processes which can be used in conjunction with this analyses methods include integration, power, square root or direct AEP amplitude computations.

Figure 10:
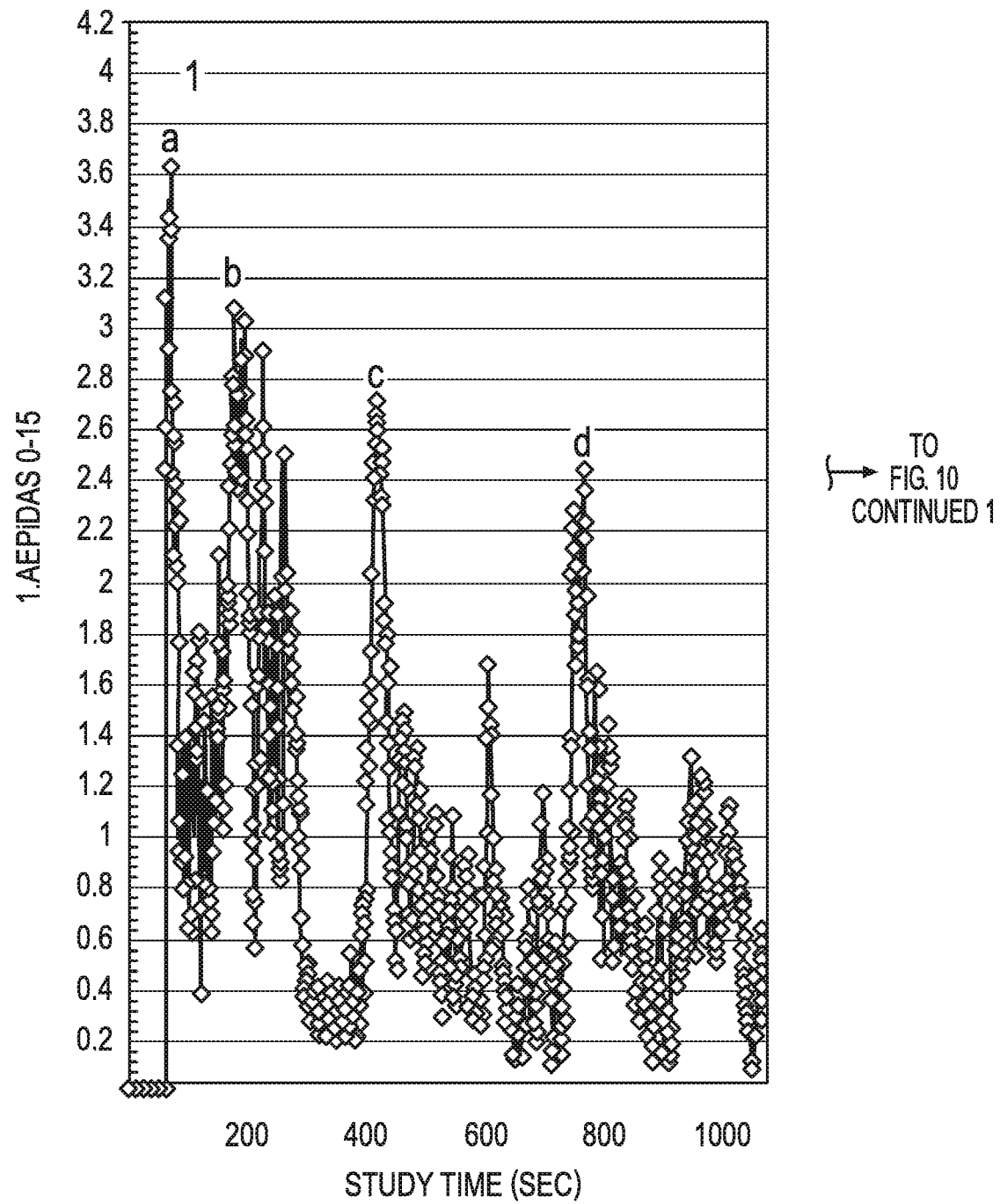
FIG. 10 Patient-13 AEPiDAS latency-dependent detection of data peaks denoted 'a' to 'd'. These series of graphs demonstrate the different A&CD data trajectory variances corresponding to SIDTM output (Graph 9) and the 8 AEPiDAS latency variances. REF: REG PAT13DIFF 8 LAT&4ANAYL&BIS 4sep08COMP PT2.xls.
Figure 10:
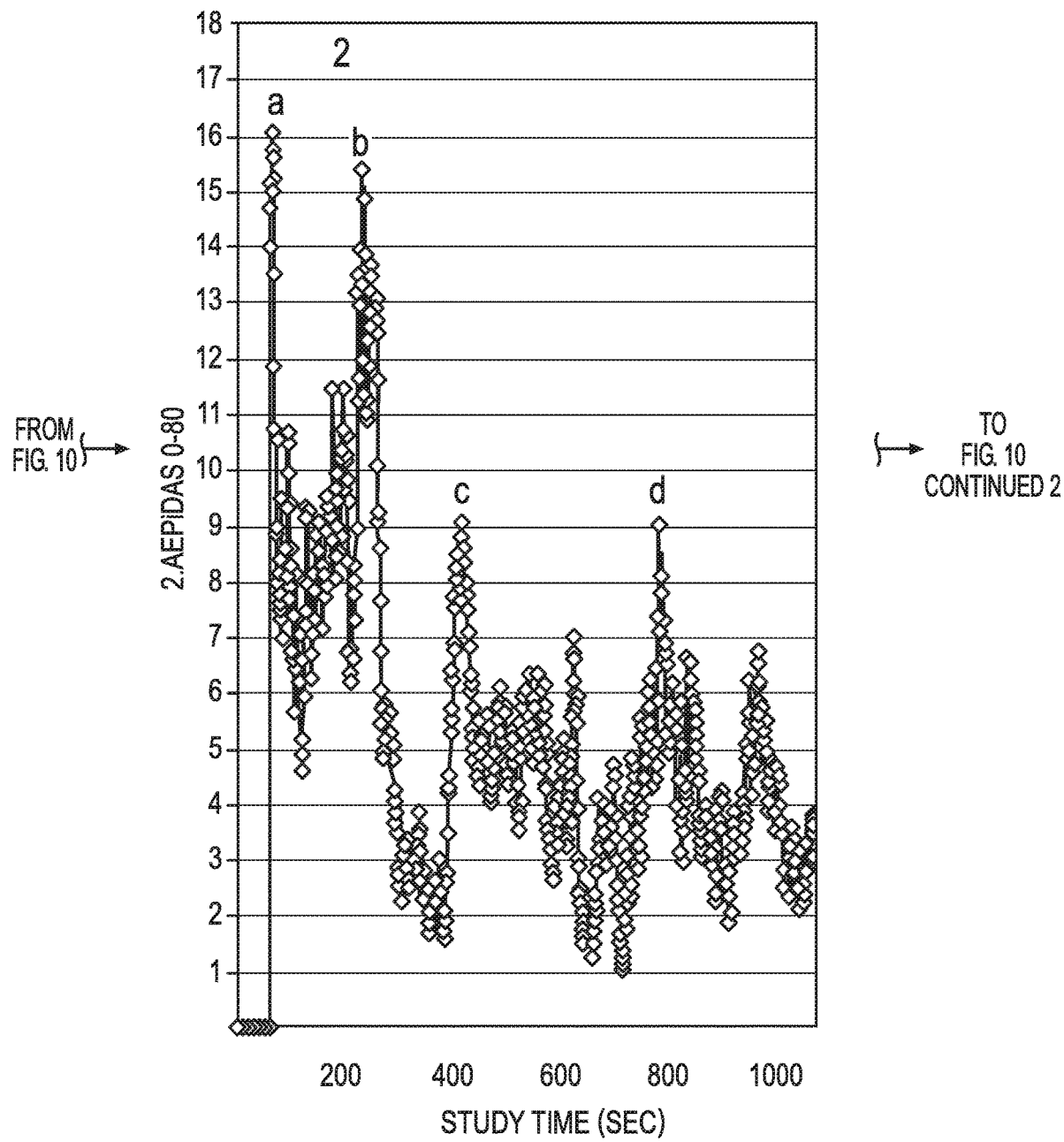
Figure 10:
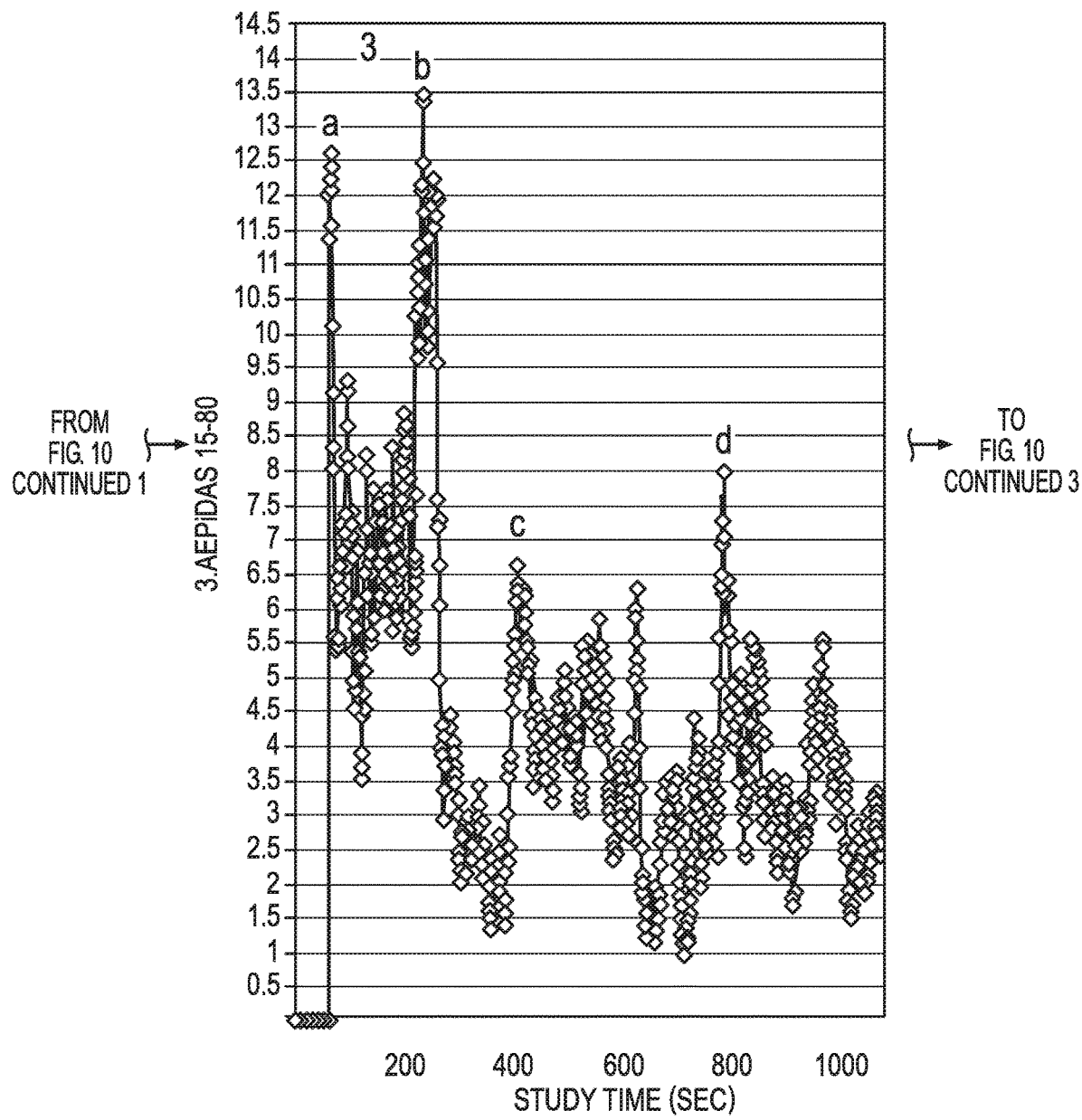
Figure 10:
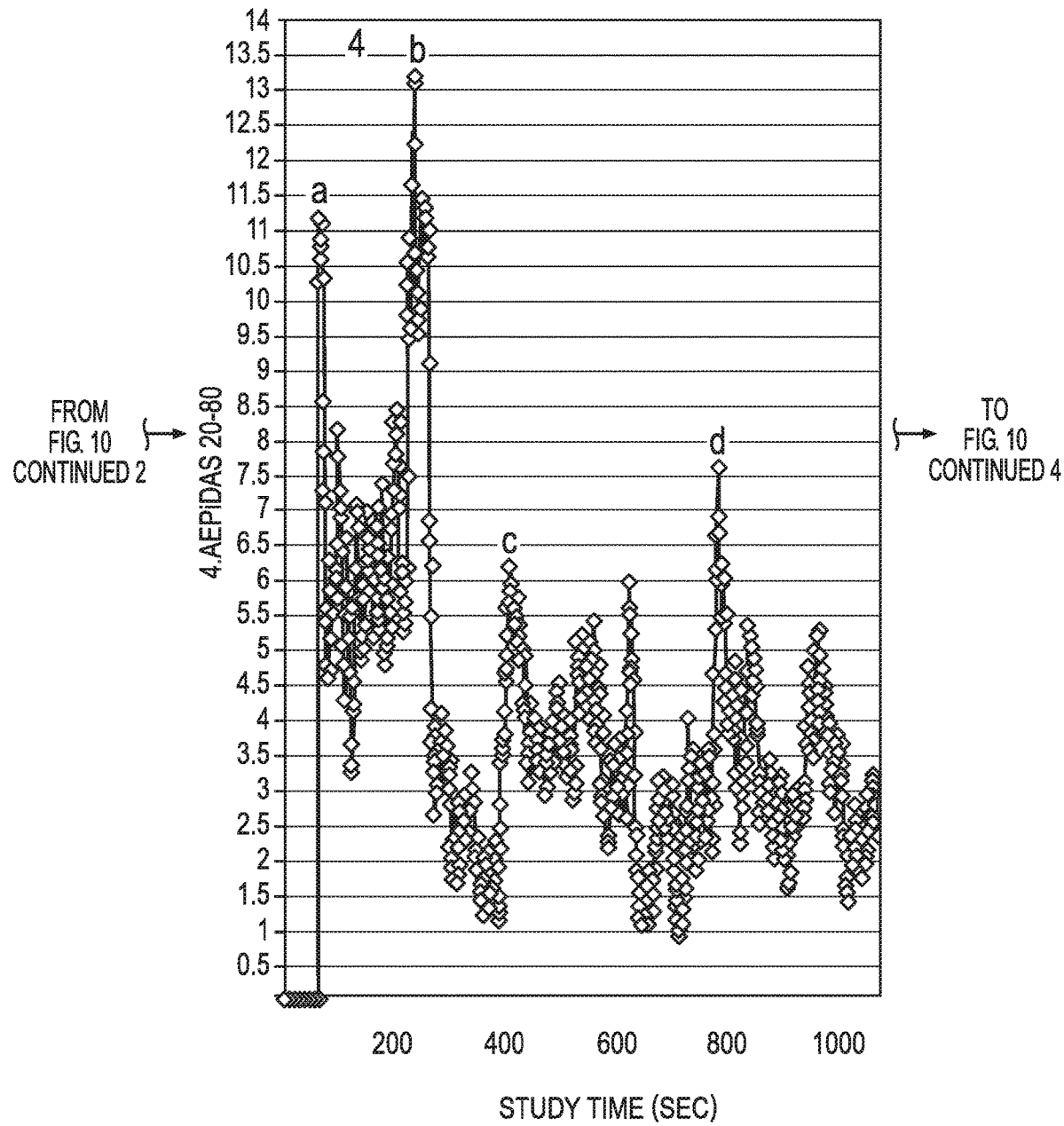
Figure 10:
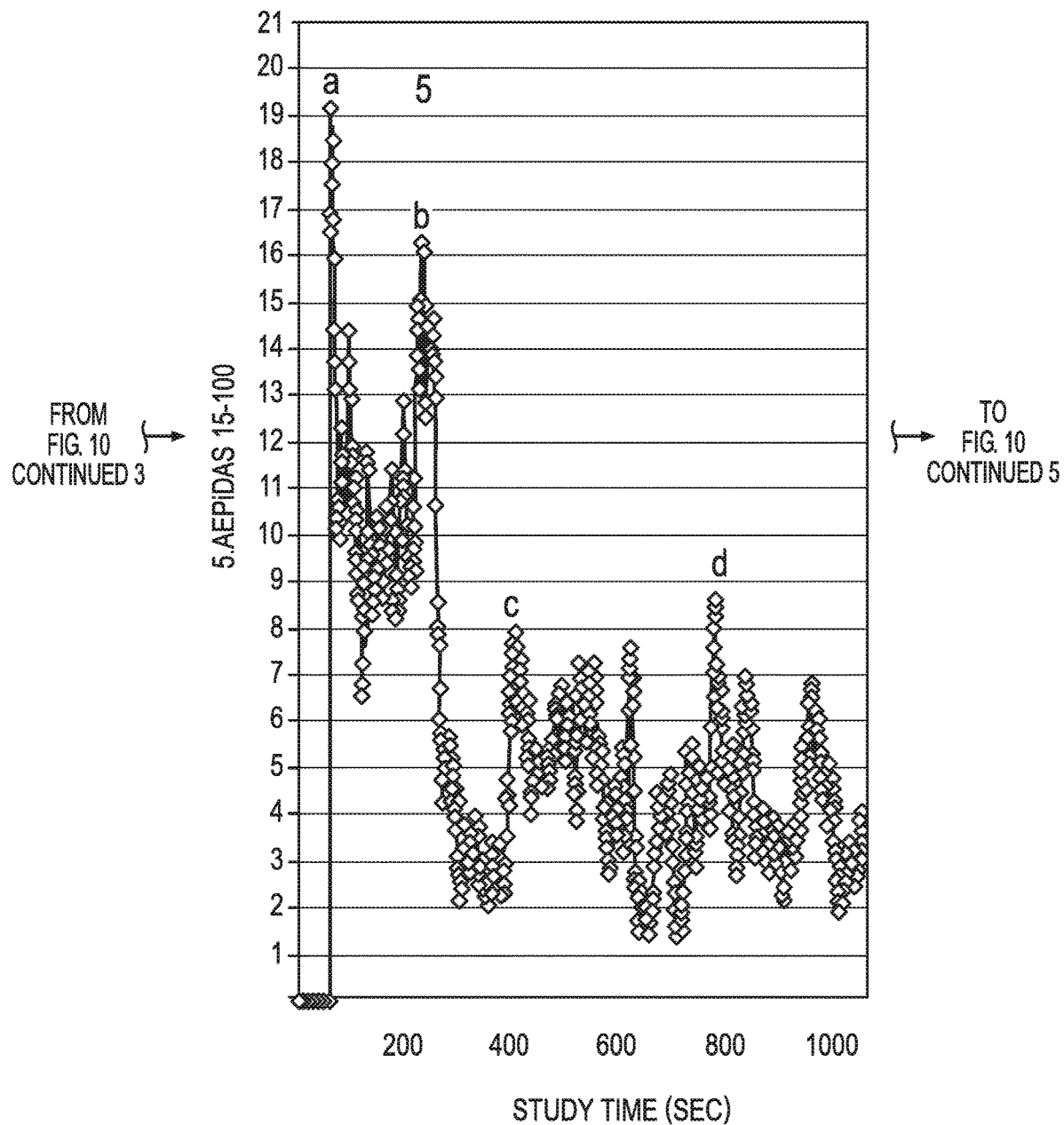
Figure 10:
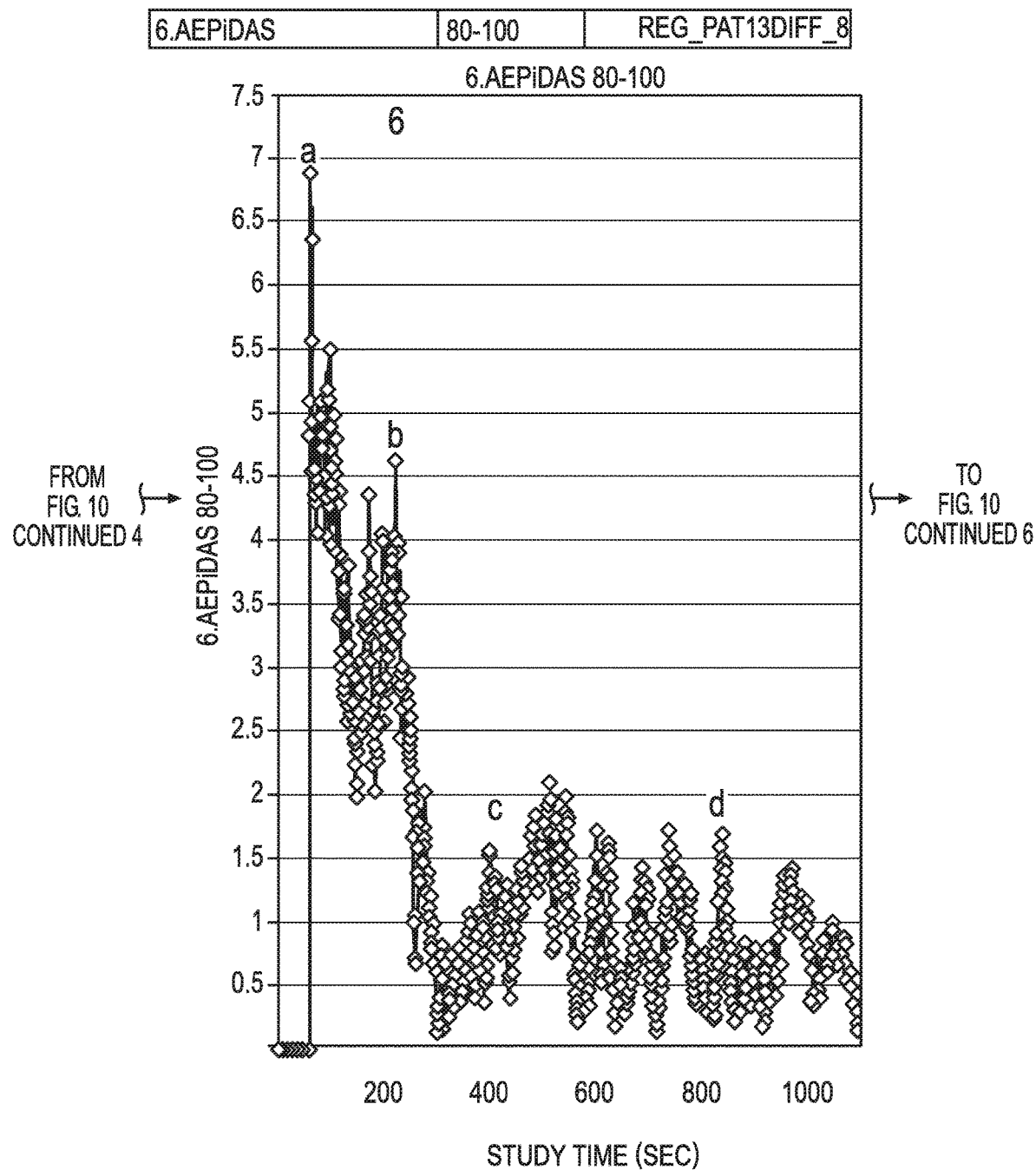
Figure 10:
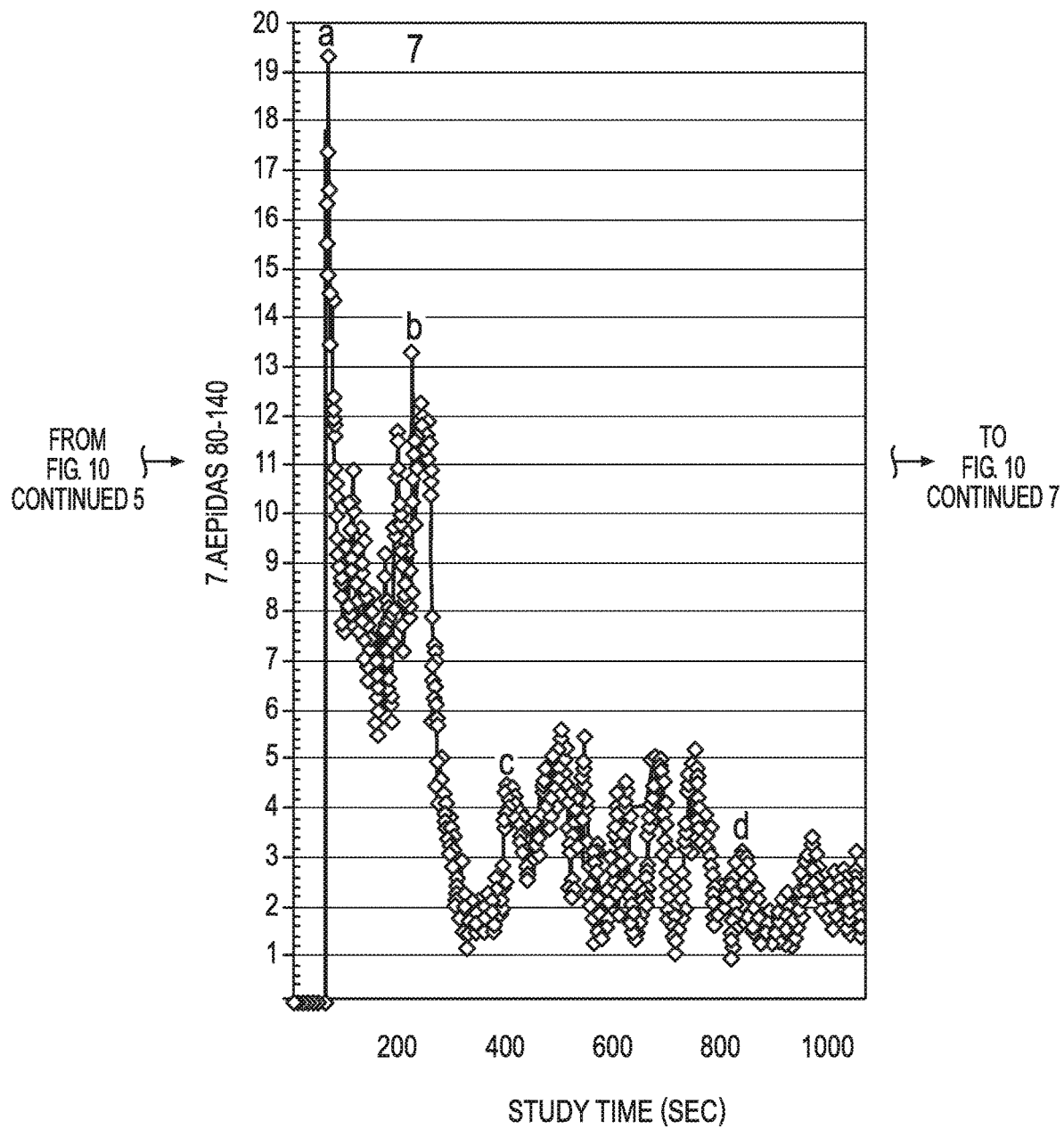
Figure 10:
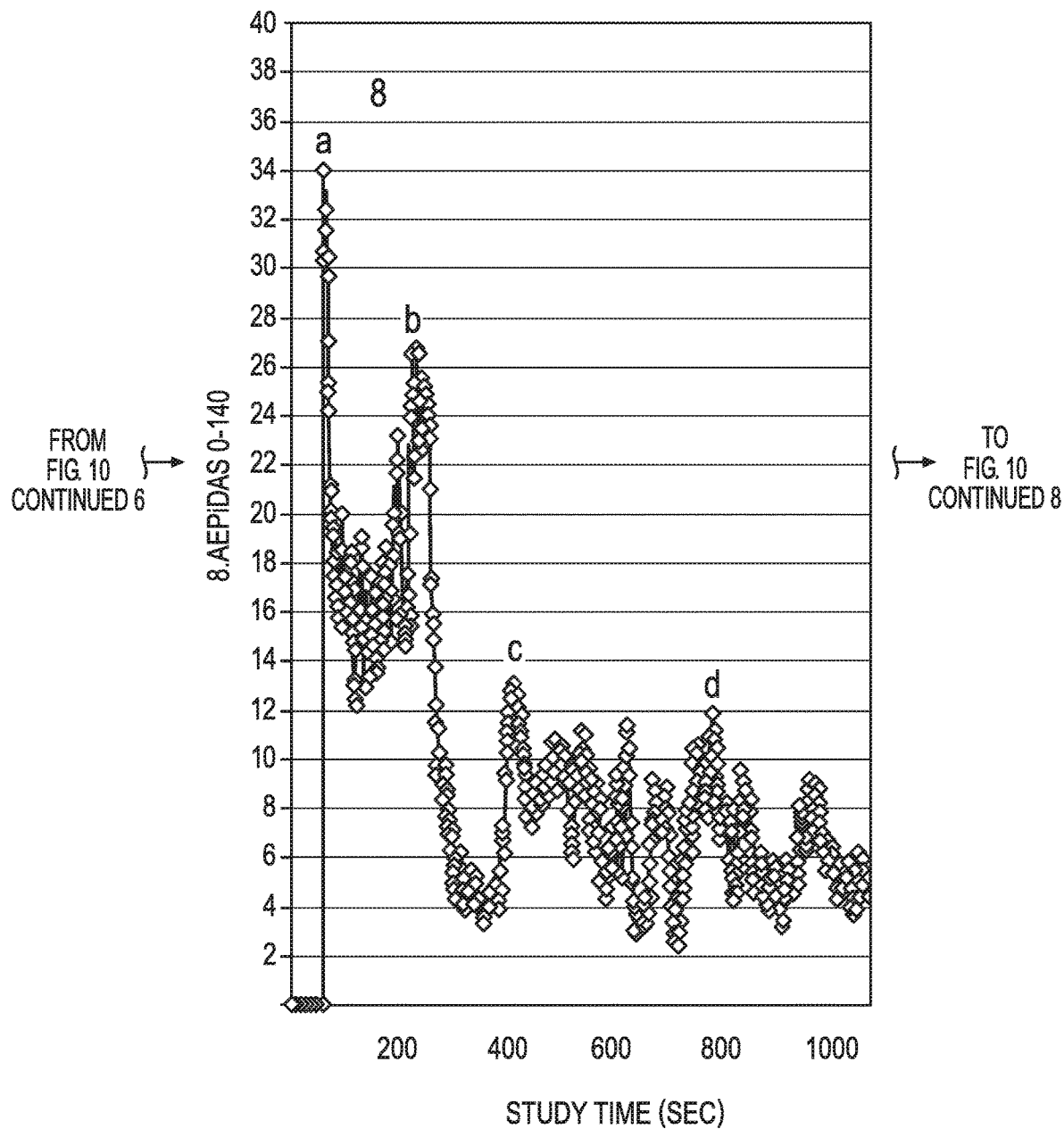
Figure 10:
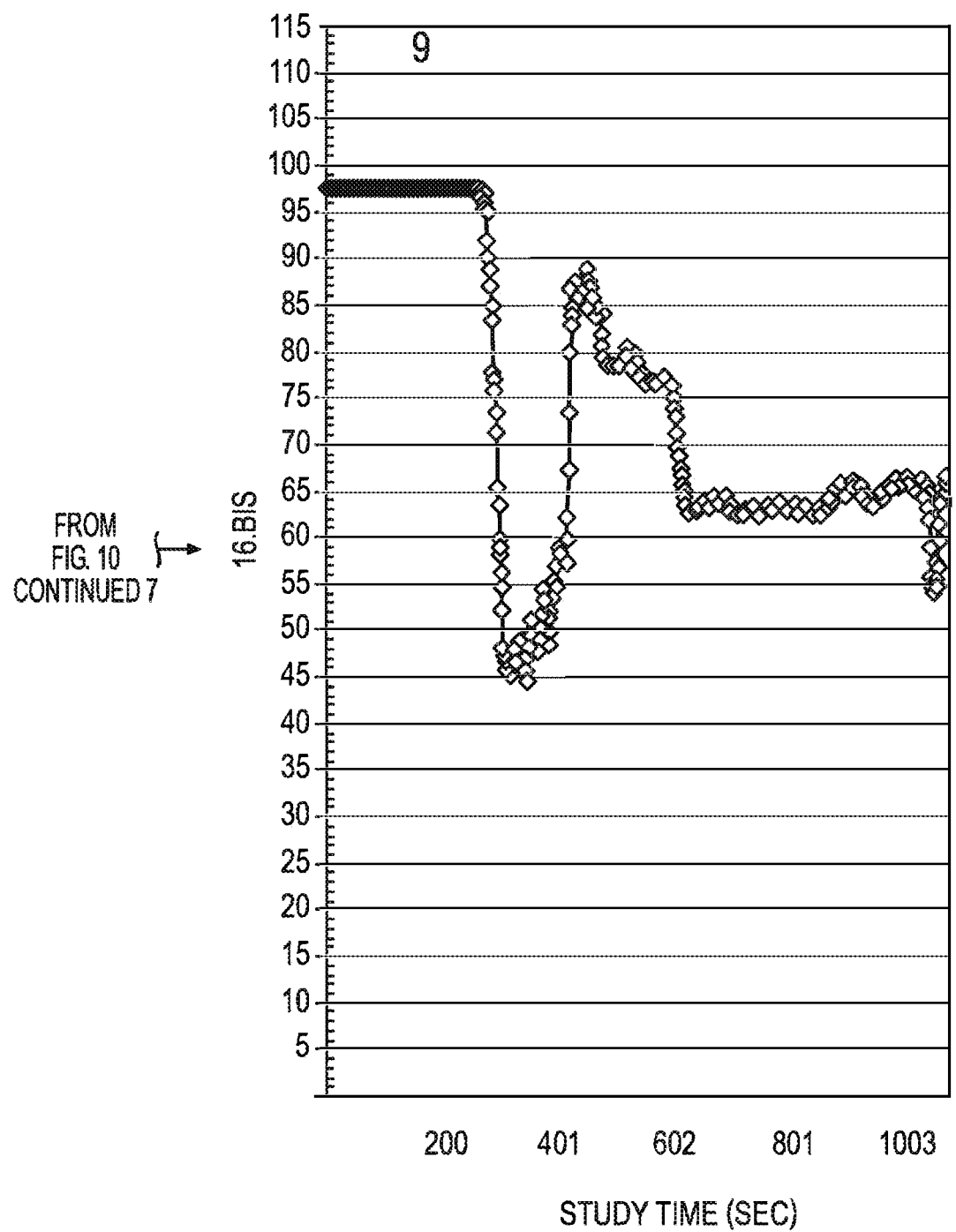
Figure 11:
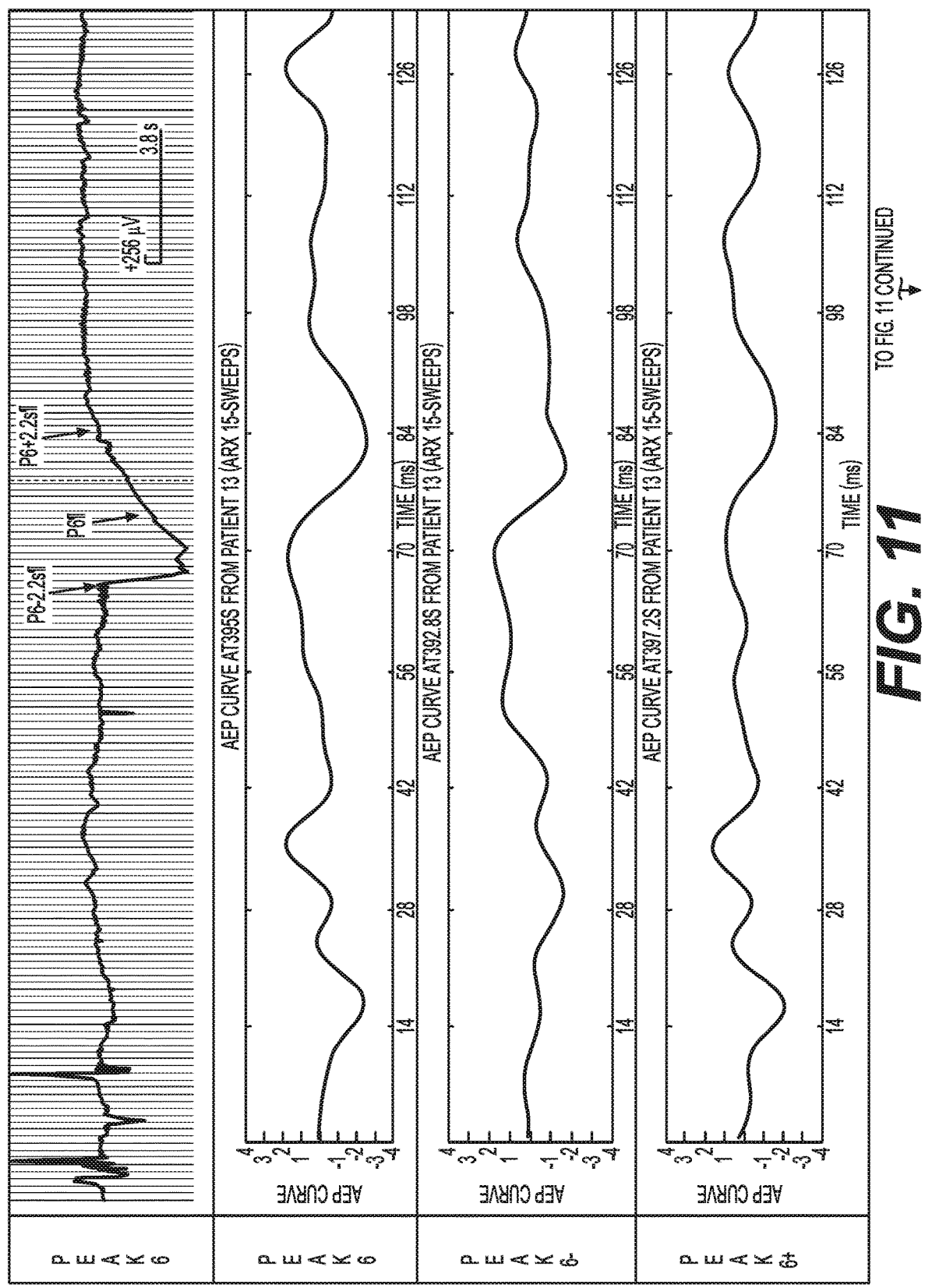
FIG. 11 Latency-interval dependent (LID) analysis and online event discrimination properties. Data traces DEMOSNTRAPAT-13 EEG and ARX 15-SWEEP AEP peak 6 (395 s) and peak 8 (779 s). Data traces shown in descending order (from top) EEG peak 6 (395 s), AEP peak 6 (395 s)
Figure 11:
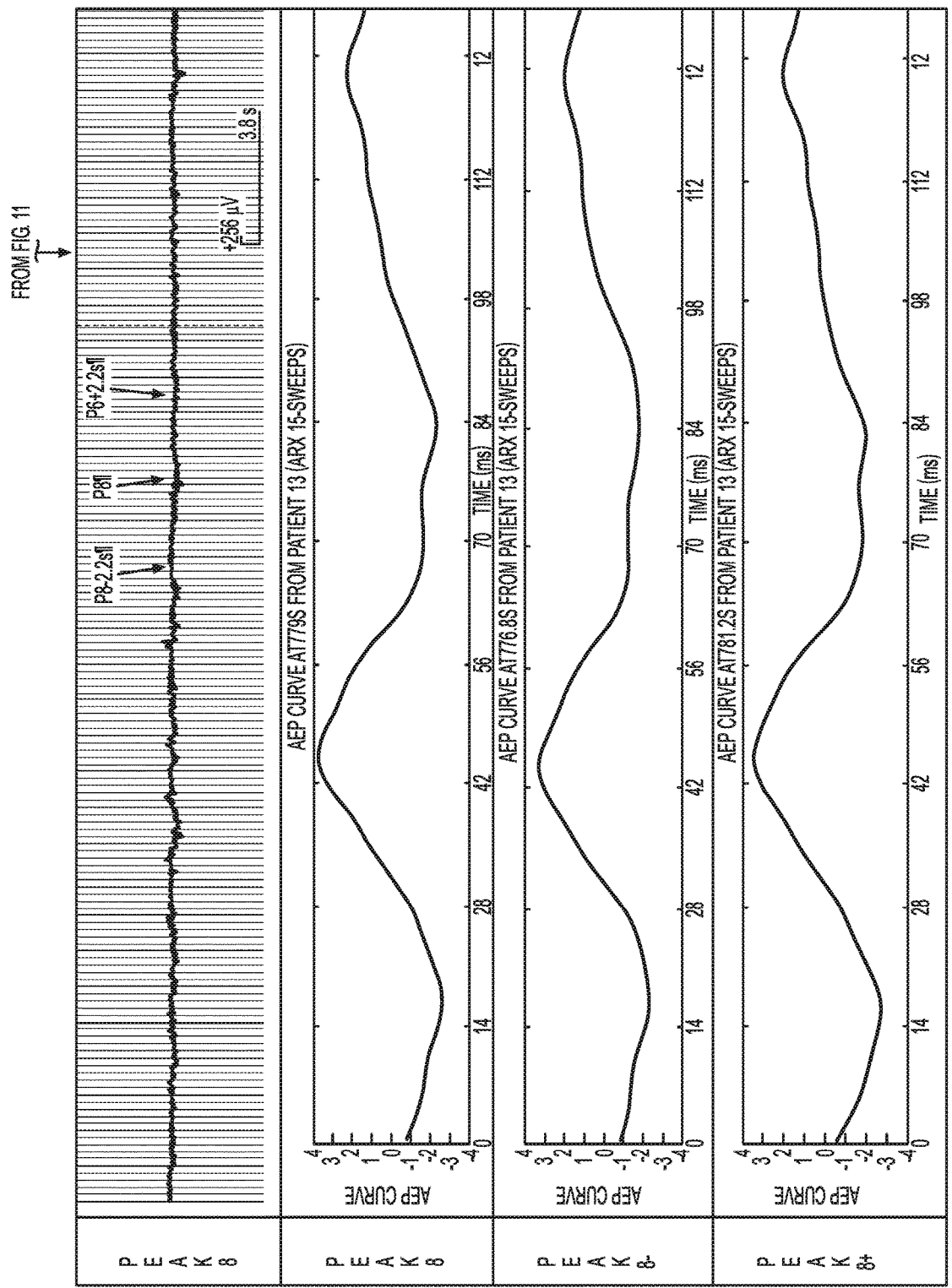

FIG. 10 and FIG. 11 Description:

FIG. 10 and FIG. 11 presents 15-sweep arx AEP averages plotted from anaesthetised surgical patient data recording showing study time (s) on x-axis and AEP NLD anaesthesia-depth indicator values on y-axis.

FIG. 10:

FIG. 10 presents a sample patient AEPiDAS latency-dependent detection of data peaks denoted 'a' to 'd', and demonstrates the unique computation of important monitoring data using the unique AEP latency-interval processes.

FIG. 10 and FIG. 11 Description:

FIG. 10 shows that the same monitoring event appears to be emphasised or deemphasised according to the latency-parameter. For example, the data peak denoted 'a' is greater in amplitude than 'b' in all graphs except 3 (15-80 ms) and 4 (20-80 ms) but graph 4 seems to be a more sensitive detector of event 'b' than graph 3.

In general these results demonstrate the high detection sensitivity for all latency-interval versions of the 256-sweep AEPiDAS averages compared to the commercially deployed BIS™ monitoring system. Additionally, examination of the data peaks (a to d) demonstrated that AEP latency-interval did influence the sensitivity of AEP detection sensitivity. Based on the higher 'd' versus 'c' data peak in graphs '3' (for example), the opposite relationship between these data peaks evident in graph '1', and the lower frequency characteristic of signal artifact associated with the raw data 'c' disturbance signals versus the higher frequency raw data nature of the 'd' artifact signal (per waveform examples (FIG. 11). The latency-interval parameter appears to exhibit unique artifact detection capabilities. In particular, based on these findings, the lower frequency data peak (per 'c' in graph 1) appears to be deemphasised with lower latency-interval parameters (0-15 ms) compared to the higher frequency 'd' artifact, while the graph-4 higher latency-interval parameters (15-80 ms) in contrast appear to emphasise the higher frequency artifact (d) and deemphasised the lower frequency 'c' artifact. These factors have value in the context of identifying online event relevant to anaesthesia-monitoring.

AEP Indicator Fluctuations

AEP noxious stimuli events can represent valuable markers of pain or pain-onset and can provide the anaesthetist one of the last lines of defence against awareness. In particular, intraoperative awareness can be accompanied with anaesthesia-induced muscle-suppression, preventing purposeful responses from a patient, even during consciousness states. Moreover, while reports note the superior detection of noxious stimuli using AEP parameters compared to those of continuous EEG, this investigation highlighted the challenge in discriminating between signal disturbances and anaesthesia-specific events such as those associated with noxious stimuli.

The value of non-linear dynamic and conventional amplitude-specific event detection has been demonstrated here (FIG. 12). As a means to examine the event-detection sensitivity during anaesthesia monitoring data peaks corresponding to patient-13 256-sweep AEP-average waveforms (FIG. 12, graphs 4 and 11), and arx 15-sweep averaged scatter-plot (FIG. 12, graph 6 and 14) were examined. As a means to examine the responsiveness to online events the comparative ratio of two indicator data peaks (IP) corresponding to the events identified in the following patient-13 (per format of FIG. 11 example) were computed. The earlier data peak is denoted IP1 and the latter IP2. Based on observing the quick body movement (BMq) classification and raw data characteristics of IP (per format of FIG. 11) and IP2 (per format of FIG. 11 example) events, as outlined in the following section, IP1 and IP2 appear similar except IP2 appears to contain a significant low frequency baseline shift, which may be related to movement artifact associated with start of anaesthesia injection, noted around this time.

FIG. 12:

FIG. 12 presents online event discrimination and delineation between any combination of CNS, PNS, MT. BM, Ar, ArNx, eye-movement, EMG intrusion or burst event discrimination and classification. In particular this data plot demonstrates the unique apparatus and associated processes to deploy non-linear dynamic AEP analysis transforms to detect and classify a range of online arousal, body movement, physiological and background noise artifact disturbances relevant during monitoring.

The non-linear dynamic process can include entropy, spectral entropy, time-series complexity-analysis, time series spectral complexity analysis or other variants of the non-linear dynamic transformation. Additionally, the other processes which can be used in conjunction with this analysis method include AEP time-interval dependent transforms, integration, power, square root or direct AEP amplitude computations.

AEP noxious stimuli events can represent valuable markers of pain or pain-onset and can provide the anaesthetist one of the last lines of defense against awareness. In particular, intraoperative awareness can be accompanied with anaesthesia-induced muscle-suppression, preventing purposeful responses from a patient, even during consciousness states. Moreover, while reports note the superior detection of noxious stimuli using AEP parameters compared to those of continuous EEG, this investigation highlighted the challenge in discriminating between signal disturbances and anaesthesia-specific events such as those associated with noxious stimuli.

The IP1 and IP2 indicator detection sensitivity are described here in terms of the ration between these two event data peaks computed for the most sensitive 256-sweep (FIG. 12, upper graphs) and 15-sweep (lower graphs) AEP-averages.

IP2:IP1 256-Sweep AEP-Average Analysis Types:

Based on 256-sweep AEP MTA (38 s response) AEP analysis types the most significant IP2:IP1 ratio was found to be 1.2 (13.1/11.1) resulting from $AEPi_{DAS\ [ave256;\ 20\text{-}80\ ms]}$ (graph 4), followed by 1.1 resulting from Entropy1 $AEPiDAS_{[ave256;\ 15\text{-}80\ ms]}$ (type 11) values (FIG. 12, top left graphs).

IP1:IP2 256-Sweep AEP-Average Analysis Types:

Based on 256-sweep AEP MTA (38 s response) AEP analysis types the most significant IP1:IP2 ratio was found to be 1.7 resulting from both Entropy1$AEPi_{DA[ave256;\ 80\text{-}140\ ms]}$ (type 15) and Entropy1 $AEPi_{DA[ave256;\ 80\text{-}100\ ms]}$ (type 14) values (FIG. 12, top right graphs).

IP2:IP1 arx 15-sweep AEP Analysis Types:

Based on arx 15-sweep AEP MTA (2.2 s response) AEP analysis methods the most significant IP2:IP1 ratio was found to be 1.1 resulting from both $AEPiDAS_{[arx;\ 80\text{-}100\ ms]}$ (graph 6) and Entropy1$AEPiDA_{[arx15;\ 80\text{-}100\ ms]}$ (graph 14) values (FIG. 12, lower left graphs).

IP1:IP2 Arx 15 Sweep AEP Analysis Types:

Based on arx 15-sweep AEP MTA (2.2 s response) AEP analysis methods the most significant IP1:IP2 ratio was found to be 1.6 resulting from both $AEPi_{DaS[arx15;\ 20\text{-}80\ ms]}$ (graph 4) values and Entropy1$AEPi_{DAS[arx15;\ 15\text{-}80\ ms]}$ (graph 3) values (FIG. 12, lower right graphs).

FIG. 13:

FIG. 13 presents an external noise sensing and cancellation system.

The noise cancellation system incorporates circuitry and algorithms capable of eliminating or minimising noise or artifact.

Artifact routines can identify the specific severity level, interval and classification of artifact.

Reduction or removal of the effects of unwanted background physiological artifacts including EMG signal intrusion, eye-blinks, EOG intrusion; arousals (various neural and autonomic categories to be included), body movements, movement time, and unwanted PAMR signal intrusion can be implemented.

Based on the deployment of this noise cancellation system the resulting biological monitoring system can tolerate high levels of electrical, EMF and other environmental interference, particularly as it relates to electrosurgical disturbances and the range of movement artifact typical of the operating theatre.

The A&CD incorporation of an open-ended "noise-sampling channel" can be considered as a means to cancel out unwanted signals as illustrated in FIG. 13. As outlined in FIG. 13 the top block [1] represents the "extraction of external noise disturbance" and comprises of an "input signal channel" and/or "open-ended or external noise sensor" input(s). The "open-ended or external noise sensor" input and corresponding stage [1] are designed to extract cyclic noise such as mains frequencies, RF generation from MRI echo planning stages, electrosurgical equipment disturbances or other sources of cyclic and often predictable noise characteristics. By extracting the specific unwanted noise signal from the broader input signal this can be input to the cancellation stage [2] where the residual extracted noise signal can be phase and amplitude adjusted in order to enable the most effective noise cancellation from the "electrophysiological input signal" input to block [4] (extraction of external noise disturbance). Block [3] denoted "tracking of residual output) enabled the subsequent block [2] to track any residual unwanted cyclic noise signals and consequently the noise cancellation within block [2] can be continuously fine-tuned for maximal noise cancellation at all times.

Noise Cancellation;

The present invention enables synchronisation between one or more external imaging or monitoring system timing reference signal, interleaving of acquisition (including sample and hold timing) whereby data is sampled in a predetermined or dynamically computed manner, whereby said interleaving or said acquisition timing can be (but not limited to) adjusted in order to enable input signals to be captured at an optimal time when unwanted signal disturbances are acquisitioned at a time when unwanted signals are able to be minimised.

Interleaving and Synchronisation During Low-Noise High-Sample Rate Data-Acquisition:

Synchronisation between one or more external imaging or monitoring system timing reference signal, interleaving of acquisition (including sample and hold timing) whereby data is sampled in a predetermined or dynamically computed manner, whereby said interleaving or said acquisition timing can be (but not limited to) adjusted in order to enable input signals to be captured at an optimal time when unwanted signal disturbances are acquisitioned at a time when unwanted signals are able to be minimised. While existent systems sample at lower sampling rates with lower subsequent lowpass frequency bandwidth characteristics (such as 5 Khz lowpass), and existent systems sample at higher sample-rates (such as 10 Khz or 20 Khz), and some systems also enable a means to synchronise the timing relationship between the acquisition sampling (sample and hold/acquisition) time and external equipment signals, a nub of the present invention is an Apparatus (or method) for monitoring or analysing biosignals comprising of any combination of the means (or method) to provide the means or steps to adjust/optimise the sychronisation between the Apparatus' acquisition relative timing and any external timing systems or timing of a sensed noise source; the interleaving of the timing between the external system or noise source timing and the optimal noise reduction trough or timing cycle; or the use of high Apparatus sampling frequencies up to and beyond 20 Khz samples per second.

FIG. 14

FIG. 14 presents a top level overview of the structured approach to sedation, pain and anaesthesia (SPA) monitoring based on the conventional approach

FIG. 15

FIG. 15 Structured Approach to Effective Sedation, Pain and Anaesthesia (SPA) Monitoring (contemporary approach) demonstrating monitoring key outcomes (goals), causal mechanisms, together with corresponding underlying measurement markers as they relate to both discrete and interrelated measurements based on a this invention's contemporary approach.

FIG. 16

FIG. 16 presents a top level flow diagram of a structured approach to sedation, pain and anaesthesia (SPA) monitoring demonstrating monitoring key outcomes (goals), causal mechanisms, together with corresponding underlying measurement markers as they relate to both discrete and interrelated measurements, with deciphering of monitored signals to ultimately track the essential clinical monitoring objectives and end-points, based on a this invention's contemporary approach.

FIG. 17

FIG. 17 presents a top level flow diagram of traditional trial and error approaches deployed during sedative, pain-suppressor and anaesthetic drug development or patient monitoring are likely to be augmented or replaced with the more specific biomarker assessment approaches, capable of teasing out the independent and interrelated effects, along with implicated cognitive/psychological mechanism and measurements, based on a this invention's contemporary approach.

FIG. 18:

FIG. 18 presents a mapped overview of the principal A&CD functional measurement requirements applicable to direct and interactive anaesthetic effects.

A series of multivariate analyses is designed to combine the applicable parameters (refer FIG. 14-FIG. 17) applicable to the essential online A&CD functional measurement and indicator criteria (outlined in subsequent requirement section).

In general, the combining analysis is capable of capturing central (AEP, EEG), peripheral (EMG) and haemodynamical information relevant to the goals and essential measures of A&CD monitoring: At least a first continuous and second evoked neurological variable monitored and processed parameters in such a manner that the monitored signals can be dissected into discrete and elementary information constituents, and then reassembled after selective emphasis and de-emphasis of the information elements. The reconstitution of one or more signals can be further enhanced using a combining method not limited to a switched process but incorporating an arbitration (weighting process) (see also SDA, below) [7; 8]. The contribution of each original signal information element can be arbitrated in accordance to the specific physiological function under of interest or under measure.

A&CD Essential Online Functional Measurement Criteria:

The A&CD functional measures can monitor direct and interrelated anaesthetic physiological effects, events, crucial or characteristic anaesthesia periods, signal quality, a provision for an overall integrated index, and integrated vital sign monitoring as outlined here.

Direct Anaesthetic Effects:

The principal measurement functions of A&CD monitoring can be arranged into 5 categories comprising of anaesthetic effects, interrelated anaesthetic effects, arousals and movement, artifact, and special A&CD features, as outlined in Direct Anaesthetic effects include hypnosis, amnesia, analgesia, immobility, anxiolysis [13; 20], while important interrelated effects include those of anxiolysis and hypnosis, and also immobility and hypnosis.

Interrelated Anaesthetic Effects:

Interrelated effects of anaesthesia including intraoperative awareness accompanied by anaesthetic muscle suppression or elevated anxiolysis. During these periods of intraoperative awareness accompanied by either anaesthetic induced muscle paralysis or elevated stress/anxiolysis the patient can be hyper-sensitive to the laying of long-term memories, leading to adverse health sequelae such as post trauma stress disorder. These functions are described elsewhere under central-peripheral-vital sign balance (CPVB) and intraoperative-recall risk factor (IRf) requirements (see also of FIG. 6).

The computation of conventional facial EMG power, combined with discrete masseter EMG and PAMR measures can be computed and registered as an EMG power/muscle suppression index (MSi) as shown in the lower right panel of FIG. 6).

A&CD Important Events Including Arousals, Body Movements, Movement Time and Artifacts:

Arousals and movement detections include arousals (total group), cortical arousals, microarousals, noxious stimuli arousals (anaesthesia-specific) body movements, movement time.

Artifact detection and indicators can be enabled for EOG signal contamination, eye-movements, 50/60 cycle or related interference, electrosurgical disturbances and EMG bursts (EMGi) [15; 24]. All signal dropout periods can be indicated.

Crucial Anaesthesia Periods and Important Measurement Characteristics:

Special A&CD feature identification and indications encompass pharmacodynamic tracking, signal quality estimation measures, periods of iso-electric conical silence and near silence, burst suppression periods, wake disturbance periods, gamma power as a measure of consciousness state, neural source estimation as a measure of A&CD anteriorisation [33].

The most critical arousals, artifact and special feature occurrences (such as markers of anaesthesia intraoperative awareness or pain/noxious stimuli) can be tracked and both indicated as an event but also as an index value. The index values can indicate relevant rates of such events based on an appropriate time base such as 30 s or 1 minute. These events include artifact in general, and specifically EOG, eye-movements. 50/60 Hz cycle or related interference, electrosurgical disturbances, and EMG bursts or wake periods (EMGi) [15; 24]. An example of the event detection and an overall arousal index is presented in the lower section of trending section of FIG. 6).

Signal Quality Measures:

In terms of signal quality an overall measure can be displayed at all times (per top section of FIG. 6) along with individual input channels signal connection and quality status as presented in lower right section of FIG. 6.

A&CDi Integrated Index:

The A&CDi can display an integrated consciousness transition marker, along with an intuitive colour display system (per A&CDi; FIG. 6). The display can be divided into 100 bargraph steps, with 5 patient states ranging from wake (A&CDi=100) through to flat-line EEG (A&CDi=0). The A&CDi values ranging from 0 to 100 can be divided into 10 segments. The highest values correspond to wake state when a patient responds to normal voice, while the next level or 20 bar-graph segments correspond to mild-hypnotic state when the patient responds to a loud voice; nudging or shaking, the next 20 bar-graph segments reflective of the general-anaesthesia state period where the patient is unresponsive to verbal stimulus and has a low probability of explicit recall, followed by deep hypnotic state.

Simultaneous Slow Trending and Fast Detection:

The display can indicate slower trending (10 s to 20 s) based on longer data smoothing requirements as graduated dosage guidance (main bar-graph display in FIG. 6), and also fast detection and indicator requirements suitable to capture rapid consciousness transitions and other fluctuations such as noxious stimuli (see AEP COtx in FIG. 6).

Display User Prompt and Event Logging:

The display can prompt user in terms of special or relevant signal status alerts such as signal quality estimation (SQE), artifact compensation and rejection (AC&R), signal/sensor quality indicator and control (SQI&C), automatic identification and channel characterisation (AICC), and the status of AEP servo-stimulus control (ASC). The special alert requirements can be displayed as part of the screen indicators and also where appropriate as part of the user prompt notification per example presented at the top of FIG. 6).

The display can alert the operator in circumstances where special user interventions such as pressure-sensitive electrode activation (PSEA; electrode re-hydration and re-abrasion requirements), wireless/battery/safety override (WBSO) and automatic mode determination (AMD) may be required. These user prompts can alert the user by way of indication such as presented in the top panel of FIG. 6 and FIG. 7 for example.

The user interface screen can enable seamless event entry capability (see also OEM requirements) as shown here in the upper screen section FIG. 6.

Vital Signs:

The ISA) with integrated reflective plethysmography-waveform oximetry (refer also IRPO) and the optional provision for airflow sensing can enable continuous monitoring and display of a range of vital sign variables (FIG. 6, right). These variables include oxygen saturation, heart rate and variability derived from the plethysmography waveform.

The ECG signal can be derived from the existent ISA surface electrode signals or supplementary ECG special-purpose ECG electrode(s), if required.

Pulse arterial tone (PAT) can be derived from the pulse waveforms, pulse transit time (PTT), and PTT-derived autonomic arousals can be possible using a combination of the oximeter and ECG parameters.

The respiration rate can be monitored where the provision for an airflow sensor is incorporated within the ISA device.

Blood pressure variation can be derived from the processed ECG and PTT parameters along with other plethysmography oximeter output products as a measure of blood pressure changes from a predefined running average base-line value (see also IRPO requirements).

Other A& CD Online Monitoring Considerations:

Reliability and Consistency: Measurement validity and consistency can be applicable to greater than 95% of patients and independent of surgery and anaesthetic drugs [9]. Strong inter- and intra-patient consistency, reliability and precision can be evident across large broadly stratified population groups and across a diverse range of anaesthetics types and mixtures.

Responsiveness to Noxious Stimuli and Other Important Spurious Signals:

Fast and accurate measures responsive to noxious stimuli will be required.

High Tolerance to Signal Disturbances:

There shall be a high tolerance to signal interference corresponding to electro-surgical (ES) intervention enabling continuous monitoring and index measures during ES. Fast recovery from ES intervention and other periods of severe signal interference must be evident, and signal blackout periods can be abolished or minimised. Discrimination between important event detections such as the presence of noxious stimuli, versus unwanted signal disturbances is an essential design consideration.

Continuous Display of Artifact Status and Online Response Delay Factor:

Under extreme monitoring conditions, where the A&CD data smoothing times must be extended to cope with the signal disturbances, appropriate display indications can alert the operator who otherwise may miss important events and not understand the change in monitoring conditions.

Consistent and Fast Online Responsiveness:

Consistent, fast (<15 s), online response delay and data smoothing characteristics, with clear indication of response delays at all times.

Operator Clutter and Overload Factors:

In general the system operator can not be overloaded or confused by cluttered or excessively "busy" displays, but rather must be clearly alerted when required. FIG. 6 can be considered in the context of a researcher interface or diagnostic display mode, but can be subjected to comprehensive user feedback a streamlined and suitable routine clinical version is deployed.

AEP Click Detection (Relevant to AEP Monitoring):

In the case of hybrid monitoring configurations accurate and reliable verification of valid AEP responses and the corresponding detection of stimulus connection.

Hierarchical Analysis Reflective of Awareness (Relevant to AEP Monitoring):

Responsive and accurate discrimination between obligatory ABR sensory, versus N1-effect (afferent; Bulter effect) changes, and higher level PCP changes, representative of awareness states, are essential aspects of the hierarchical AEP processing.

Diagnostic-Mode Graphic User Interface:

The A&CD graphic user interface can present the measures as illustrated here in FIG. 6.

The top right of panel display can indicate an overall integrated index representation (A&CDi). The top left portion of the display can activate the "view mode" function, enabling a range of useful preconfigured anaesthesia-specific operator complexity levels (OICL) as also here in FIG. 6. More streamlined and simplified A&CD display formats can be provided for routine clinical purposes, but these formats are subject to extensive studies involving clinician and researcher feedback.

FIG. 19
Classification of Conventional and Anaesthesia-Specific Online Events

Based on examining anaesthesia indicator AEP trajectories (pat, n=16) across all patients it has been demonstrated that both arx 15-sweep and slower 256-sweep AEP MTA indicator values appropriately represent arousal, body movement, and artifact fluctuations, while bispectral index EEG-based measures tend to cancel these rapid changes. In particular, anaesthesia-specific events were established based on quick body movements (BMq), quick arousals (Arq) and noxious stimuli (Nx) arousals. In terms of noxious stimuli events both body movement (NxBM) and cortical (NxC) types were observed, which has implications in terms of detecting CNS generated markers representative of A&CD reversal effects as opposed to signal disturbances generated by clinical staff patient intervention and subsequent movement events. The classification of these events has important implications in terms of capturing markers of anaesthesia-specific pain or anaesthesia reversal and consequential intraoperative awareness. While these results implicate the importance of anaesthesia-specific online monitoring it is also evident that these new online event detection methods can improve not only true positive prediction outcomes, but also minimize false negatives and false positives.

FIG. 19 summarises the conventional and anaesthesia-specific arousal, artifact and movement events based on established (conventional) and anaesthesia-specific (proposed) classification methods. The lower section of the figure presents a series of proposed online anaesthesia-specific indices.

A&CD 14 Aug. 10 Provisional Claim Group Abstract/Over Views

The earlier generation anaesthesia monitoring incorporated clinical signs such as pupil response, patterns of respiration, quality of the pulse and movement augmented by direct measurement of physiologic endpoints including blood pressure, heart rate and respiratory rate and volume. Further developments lad to the deployment of pulse oximetry and capnography, enabling precise assessment of the ventilatory system while a patient underwent anaesthesia. Additionally, the use of end-tidal agent analysis and the stimulation of peripheral nerve enables the anaesthetist to measure pharmacologic agent concentration and effect. In more recent times cardiac function can be assessed during anaesthesia using pulmonary artery catheters and transesophageal echocardiography to enable continuous blood pressure and cardiac output monitoring. Moreover, the latest developments provide neurophysiological monitoring of the central nervous system enabling a direct measure of brain status during anaesthesia and sedation, and enable an even finer perioperative dosage control. However, while it has been recognised that more accurate monitoring of brain effect in combination with traditional monitoring can provide a more complete approach to the optimal adjustment of anaesthesia, sedatives and analgesic agents published studies now articulate some of the earliest evidence demonstrating the benefits of correlating and combining some specific physiological dimensions and tracking more specific anaesthesia-effects and events. The ISA device and subsequent processing devices and algorithms covered by this PCT outline a series of these new developments in the form of a number of new patent claims as detailed in claim section.

Claim Series 1: Integrated Sensor Attachment Device

The $1^{st}$ series of subsequent diagnostic device claims per claim section relate to a patient-applied integrated sensor attachment (ISA) device for the assessment of an individual's psychological and/or physiological state during anaesthesia, sedation, or meditation or un-meditated states, comprising sensors integrated into a single flexible substrate and the sensors include at least one electrophysiological evoked or continuous electroencephalography (EEG) monitoring sensor, at least one electromyography (EMG) monitoring sensor segregated from EEG signal regions, including the electrode sensor registrations located over the masseter and/or postauricular regions, and the provision for an integrated vital sign monitoring sensor, as a means to track 2 or more 2 or more physiological groups of parameters applicable to hypnosis, amnesia, analgesia, immobility, axiolysis and vital sign changes.

Claim Series 2: Integrated Sensor Attachment Method

The $2^{nd}$ series of subsequent diagnostic process per claim section relate to a patient-applied integrated sensor attachment (ISA) for the assessment of an individual's psychological and/or physiological state during anaesthesia, sedation, or meditation or un-meditated states, comprising sensors integrated into a single flexible substrate and the sensors include at least one electrophysiological evoked or continuous electroencephalography (EEG) monitoring process, at least one electromyography (EMG) monitoring process segregated from EEG signal processes, including masseter processes and/or postauricular processes, and the provision for an integrated vital sign monitoring process, as a means to track 2 or more 2 or more physiological groups of parameters applicable to hypnosis, amnesia, analgesia, immobility, axiolysis and vital sign changes.

Claim Series 3: Preamplifier Device

The $3^{rd}$ series of diagnostic device claims listed in claim section relate to a compact patient interface device (module) designed to provide interconnection between the said "patient-applied" ISA device, enabling multidimensional (parameters include two or more hypnosis, amnesia, analgesia, immobility, anxiolysis functions) processing, measurement, and associated system display functions. (ie device claims for electronic interface module between ISA and processing unit)

Claim Series 4: Preamplifier Method

The 4 series of diagnostic method claims listed in claim section relate to a patient preamplifier signal processing methods including adaptable input electrosurgical filtering processes, processes enabling interlinking between online detection of electrode connections, signal quality, and close proximity LED or other display indicators intuitively signaling system user's need to attend to electrode or sensor attachment or patient top sensor attachments systems (such as but not limited to activation of pressure regelling and/or re-abrasion pressure pads or direct movement and/or pressure to electrode or sensors to optimise signal monitoring), etc (INCLUDES SPECIAL PREAMPLIFIER METHODS SUCH AS ADAPTABLE INPUT ELECTROSURGICAL INPUT FILTERS, ETC)

Claim Series 5: ER Hierarchical/Multidimensional Psychological and Physiological Monitoring Device The $5^{th}$ series of diagnostic device claims listed in claim section relate to a hierarchical evoked response analysis system including parts designed to disassemble composite AEP signals into the different functional information channels representative of the lower level ABR sensory responses, the N1 markers indicative of the arrival of the stimulus through the cochlear and auditory nerves to the cerebral cortex (such as N1 presence), the afferent neural responses (such as N1-effect), elevated N1-P2 amplitudes corresponding to increased refractory period (inter-stimulus interval; ISI), MLAEP amplitude-latency changes with deeper anaesthesia, through to the processing contingent potentials (PCP) indicative of the higher order attention states indicative of the laying down of longer term memories implicated during intraoperative recall.

Neurophysiological responses evoked during anaesthesia and/or consciousness depth, sedation or other activities result from ensembles of signals generated from underlying non-linear synaptic actions. However, while these resulting neurophysiological responses are assembled and then segregated in accordance to their psychological and physiological origins, they have mainly been dealt with in an overall or blunted manner.

For example, adverse anaesthesia sequelae such as intraoperative awareness and associated post traumatic stress disorder recall remain a primary risk, along with the inability to administer anaesthesia in cases where the small margin of safe deployment is too risky in trauma cases, where cardiac or respiratory function are already stressed.

Therefore the present invention is designed to overcome such limitations by monitoring an individual's physiological and psychological parameters in such a way that the user is able to track the essential events and conditions relevant to changes within the sensory, central nervous, and other peripheral and vital sign systems applicable to the safe medical procedures and deployment of mind or physiological altering therapeutics. In particular, the conventional discrete and not integrated measures of A&CD are enhanced with more specific markers and measures of both the independent and integrated correlates applicable to A&CD monitoring.

The series of diagnostic device claims listed in claim section relate to a hierarchical evoked response analysis system including parts designed to disassemble composite AEP signals into the different functional information channels representative of the lower level ABR sensory responses, the N1 markers indicative of the arrival of the stimulus through the cochlear and auditory nerves to the cerebral cortex (such as N1 presence), the afferent neural responses (such as N1-effect), elevated N1-P2 amplitudes corresponding to increased refractory period (inter-stimulus interval; ISI), MLAEP amplitude-latency changes with deeper anaesthesia, through to the processing contingent potentials (PCP) indicative of the higher order attention states indicative of the laying down of longer term memories implicated during intraoperative recall.

Neurophysiological responses evoked during anaesthesia and/or consciousness depth, sedation or other activities result from ensembles of signals generated from underlying non-linear synaptic actions. However, while these resulting neurophysiological responses are assembled and then segregated in accordance to their psychological and physiological origins, they have mainly been dealt with in an overall or blunted manner.

For example, adverse anaesthesia sequelae such as intraoperative awareness and associated post traumatic stress disorder recall remain a primary risk, along with the inability to administer anaesthesia in cases where the small margin of safe deployment is too risky in trauma cases, where cardiac or respiratory function are already stressed.

Therefore the present invention is designed to overcome such limitations by monitoring an individual's physiological and psychological parameters in such a way that the user is able to track the essential events and conditions relevant to changes within the sensory, central nervous, and other peripheral and vital sign systems applicable to the safe medical procedures and deployment of mind or physiological altering therapeutics. In particular, the conventional discrete and not integrated measures of A&CD are enhanced with more specific markers and measures of both the independent and integrated correlates applicable to A&CD monitoring.

The eleventh series of diagnostic method claims listed in claim section relate to a hierarchical evoked response analysis processes (read in the context of the above device claim series) designed to disassemble composite AEP signals into the different functional information channels representative of the lower level ABR sensory responses, the N1 markers indicative of the arrival of the stimulus through the cochlear and auditory nerves to the cerebral cortex (such as N1 presence), the afferent neural responses (such as N1-effect), elevated N1-P2 amplitudes corresponding to increased refractory period (inter-stimulus interval; ISI), MLAEP amplitude-latency changes with deeper anaesthesia, through to the processing contingent potentials (PCP) indicative of the higher order attention states indicative of the laying down of longer term memories implicated during intraoperative recall.

Claim Series 6: ER Hierarchical/Multidimensional Psychological and Physiological Monitoring Method The $6^{th}$ series of diagnostic method claims listed in claim section relate to a hierarchical evoked response analysis processes (read in the context of the above device claim series) designed to disassemble composite AEP signals into the different functional information channels representative of the lower level ABR sensory responses, the N1 markers indicative of the arrival of the stimulus through the cochlear and auditory nerves to the cerebral cortex (such as N1 presence), the afferent neural responses (such as N1-effect), elevated N1-P2 amplitudes corresponding to increased refractory period (inter-stimulus interval; ISI), MLAEP amplitude-latency changes with deeper anaesthesia, through to the processing contingent potentials (PCP) indicative of the higher order attention states indicative of the laying down of longer term memories implicated during intraoperative recall.

Claim Series 7: Environmental Noise Sensing and Cancellation (ENS&C) Biological Monitoring Device Title: Environmental noise sensing and cancellation (ENS&C) system.

The $6^{th}$ series of claims listed here relate to an environmental noise sensing and cancellation (ENS&C) system incorporating a noise sensing input and/or other signal input whereby the unwanted noise within a biological monitoring environment can be senses or monitored and then be processed in such a way as to enable unwanted noise to be cancelled out from signals of interest.

Claim Series 8: Environmental Noise Sensing and Cancellation (ENS&C) Biological Monitoring System Method Abstract

Claim Series 9: Spectral Stimulus Validation System Device

Claim Series 10: Spectral Stimulus Validation Method

Claim Series 11: Spectral Noise and Distortion Tracking and Dynamically Linked Signal Processing Device

Claim Series 12: Spectral Noise and Distortion Tracking and Dynamically Linked Signal Processing Method

Claim Series 13: Adaptable Aperture Acquisition System Device

Title: Adaptable Acquisition Aperture (AAA) system.

The 13th series of claims deals with an adaptable acquisition aperture (AAA) biological monitoring apparatus enabling minimization of unwanted environmental or external system noise, by way of automatic, manual or computer-assisted data acquisition sample and hold aperture adjustment. In particular, the sample and hold aperture window can be adjusted in such a manner that the input signal is captured at successive points in time which are synchronized and positioned to sample and hold the input signal between cyclic noise peaks. Consequently the AAA system can interleaves the aperture window between unwanted cyclic external noise peaks in order to minimize the corresponding interference effects within signals of interest.

Claim Series 14: Adaptable Aperture Acquisition Method

Claim Series 15: Earlier Version is a Patent Claim Group: A&CD Biological Awareness Monitoring System Device

Claim Series 16: Earlier Version is a Patent Claim Group: A&CD Biological Awareness Monitoring System Device EARLIER CLAIM VERSION PATENT CLAIM GROUP 3: INTRAOPERATIVE RECALL SUSCEPTIBILITY MEASURES. CURRENT CLAIMS INCLUDE ER HIERACHICAL/MULIDIMENSIONAL PSYCHOLOGICAL AND PHYSIOLOGICAL MONITORING DEVICE CLAIM GROUP.

Claim Series 17: Biological Monitoring System Combinational Analysis Method

The 17TH series of diagnostic method claims listed in claim section relate to the method associated with processing incorporating means of extracting individual measures and combinational measures corresponding to multidimensional (parameters include two or more hypnosis, amnesia, analgesia, immobility, anxiolysis functions) processing (computational algorithms) and display (raw data and various derived indices) functions.

Claim Series 18: Earlier Version (A&OC&OD Monitoring System Combinational Analysis Method

Claim Series 19: Earlier Version (A&OC&OD Monitoring & Drug Delivery Device

The 19th series of drug delivery device claims listed in claim section relate to the device associated with the online determination of the optimal combination of drug delivery compounds corresponding to multidimensional (parameters include two or more hypnosis, amnesia, analgesia, immobility, anxiolysis functions) parameters derived from the said "device", "diagnostic method", and "diagnostic design" claims covering diagnostic monitoring, processing (computational algorithms) and display (raw data and various derived indices) functions. (ie device claims for drug delivery bio-feedback system corresponding to deployment of any of described ISA device, ISA design, patient-interface device, patient-interface method, and/or A&CD monitoring method as a means of contributing to the mixing and delivery rates of anaesthetic compounds (anaesthetic compounds responsible for A&CD-effects including those of hypnosis, amnesia, analgesia, immobility, anxiolysis functions).

Claim Series 20: Earlier Version (A&OC&OD Monitoring & Drug Delivery Method

The 20th series of drug delivery method claims listed in claim section relate to the method associated with the online determination of the optimal combination of drug delivery compounds corresponding to multidimensional (parameters include two or more hypnosis, amnesia, analgesia, immobility, anxiolysis functions) parameters derived from the said "device", "diagnostic method", and "diagnostic design" claims covering diagnostic monitoring, processing (computational algorithms) and display (raw data and various derived indices) functions. (ie device claims for drug delivery bio-feedback system corresponding to deployment of any of described ISA device, ISA design, patient-interface device, patient-interface method, and/or A&CD monitoring method as a means of contributing to the mixing and delivery rates of anaesthetic compounds (anaesthetic compounds responsible for A&CD-effects including those of hypnosis, amnesia, analgesia, immobility, anxiolysis functions).

Claim Series 21: Neural Source Estimated (NSE) A&CD Monitoring for Anteriorisation or Difference in Frontal Versus Occipital Lobe Activity and/or Corresponding Changes or Shifts in Brain Activity Device Anterior and Posterior Lobes
Anaesthesia and Dementia Neurological diseases such as dementia present a growing issue amongst anaesthesiologists, especially as the aged population and corresponding prevalence and severity of these diseases increases. Side effects of such diseases include cognitive unbinding [19] or reduction in neurological cohesion, and effects such as anteriorisation [34; 34]. Such changes in turn generate shifts in neural topographic foci, temporal sequences and more general alterations of the EEG spectral composition.

The PSI computation incorporates EEG power, frequency, and phase information from anterior-posterior relationships of the brain, in conjunction with coherence between bilateral regions Pa has been shown (neuromagnetic recordings) to correlate with activity in the supratemporal auditory cortex, while the anterior-posterior plane contributes to changes in Pa waveform morphology.

In another study left and right hemispherical EEG monitoring registrations were recorded using two CSM systems. Despite reports of lateralisation during anaesthesia, strong EEG correlation was found between the left and right brain hemispheres. Other reports have demonstrated poor CSI prediction of autonomic or somatic response to incision.

EEG cerebral lateralisation changes known to occur during cognition, sleep and waking were investigated by Anderson and Jakobsson (2006) during 25 surgically anaesthetised patients (n=584). The researchers recorded brain waves using two CSI monitors, with each monitor configured to record simultaneously, the left-side and right-side EEG electrode registrations simultaneously. In contrast to reports of brain lateralisation during sleep [5; 16; 22; 25], the researchers found very high correlation between the left and right hemispherically registered EEG pairs [1].

The 21$^{st}$ series of drug delivery device claims listed in the proceeding section per claim section relate to a device or method for the determination and/or monitoring of subject's transitional (biphasic or switch-like) or graduated changes of psychological or physiological states corresponding to unmedicated, or medicated states of anaesthesia or sedation, and in particular the changes applicable to neural source localisation changes or differences (hemispherical/lateralisation or changes between the frontal regions or occipital regions or directional shifts of activity associated with these regions. In particular a NSE device or method enable hemispherical/lateralization differences or brain activity shifts using as few as 2 EEG electrodes (such as 2 forehead frontal lobe monitoring electrodes), or frontal to occipital (and visa versa) differences or directional shifts brain activity with a few one additional electrode (total of 3 electrode including 2 left and right forehead electrodes, fro example. This NSE system can be applied to routine ambulatory or clinical applications where the monitoring of brain changes of this nature can combined with other information to assist in the determination of a patient sentient state during anaesthesia, sedation, or un-medicated behavioral assessments.

Claim Series 22: Neural Source Estimated (NSE) A&CD Monitoring for Anteriorisation or Difference in Frontal Versus Occipital Lobe Activity and/or Corresponding Changes or Shifts in Brain Activity Method Claim Series 35: A Structured and Hierarchical System Enabling Independent and Special-Case Interrelated Signal Ensembles Applicable to Sedation, Pain and/or Anaestehsia Monitoring to be Segregated into the Essential Biomarker Information Channels According to Underlying Physiological and Cognitive/Psychological Mechanisms Whereby the SPA Goals Include (but not Limited to):
1. Hypnosis.
2. Amnesia,
3. Analgesia,
4. Immobility,
5. Sedation, and
6. Safe and stable physiological and cognitive function.

Whereby the Underlying SPA Physiological and Cognitive/Psychological Mechanisms Include (but not Limited to):
1. Hypnosis: central nervous system (CNS): cognitive functions, psychological functions
2. Amnesia: autonomic nervous system; other physiologic control systems including central integrative (mainly learning, memory, and possible laterality of brain function), endocrine control mechanisms; adrenal glands (hormones such as Epinephrine/a.k.a adrenaline is a hormone and neurotransmitter, implicated during stress and related memory consolidation).
3. Analgesia: central nervous system (CNS), peripheral nervous system,
4. Immobility: peripheral nervous system, motor systems, muscle systems:
5. Sedation: sensory system;
6. Safe and stable physiological and cognitive function: Integrative Organ Functions (most SPA monitoring) including muscle, heart; circulation, respiration, pulmonary circulation, gas exchange, and control of breathing, regulation of body temperature.

Whereby the SPA Monitoring Biomarkers Include (but are not Limited to):
1. Hypnosis: evoked potential (EP) and continuous EEG signals.
2. Amnesia: evoked and continuous EEG signals in conjunction with vital sign signals indicative of a release of hormones and neurotransmitters, marked by elevated vital sign measures and the risk of intraoperative recall memory consolidation.
3. Analgesia: can be marked by graded or spontaneous changes in EP and/or continuous EEG resulting from nerve impulses arriving at the central nervous system (spine or brain).
4. Immobility: can be marked by graded or spontaneous changes in PAMR and/or continuous EMG resulting from changes in muscle tonicity or activity.
5. Sedation: Can be marked by base-line versus graded or spontaneous elevation of vital sign and other physiological measures.
6. Safe and stable physiological and cognitive function: Can be marked by safe, operational modes of vital sign, physiological cognitive measures.

Whereby Special Case SPA Monitored Biomarker Interrelationships Include (but are not Limited to):
1. Hypnosis accompanied by elevated vital sign and/or other physiological measures. This could be a case of mistaken hypnosis interpretation during pharmaceutically induced muscle paralysis, accompanied with intraoperative awareness.
2. Hypnosis accompanied by elevated measures of mobility. This could be a case of mistaken hypnosis interpretation during intraoperative awareness.
3. Cortical or subcortical arousals accompanied by graded or spontaneous changes in vital sign or other physiological changes, indicative of nerve impulses reaching the spinal chord or brain and the corresponding release of hormones and neurotransmitters (a.k.a adrenaline or endorphins) preventing nerve cells from releasing more pain signals, but also contributing to vital sign changes (such as of increases in heart rate, contracts blood vessels, dilated air passages and other symptoms of intraoperative awareness flight-or-fight drive to the sympathetic nervous system) and the burning of permanent memories (memory consolidation), implicated with intraoperative recall.

4. Monitoring of graded or spontaneous brain signal arousals or other changes indicative of nociception (neural processes of encoding and processing noxious stimuli) associated with electrosurgical processes, stitches and other surgical stimuli.

5. Monitoring of graded or spontaneous brain signal arousals or other changes indicative of nociception (neural processes of encoding and processing noxious stimuli) associated with electrosurgical processes, stitches and other surgical stimuli, by way of associating the time alignment between these stimuli events and the resulting change in physiological or cognitive states of the individual under assessment.

6. Monitoring of graded or spontaneous brain signal arousals or other changes indicative of nociception (neural processes of encoding and processing noxious stimuli) associated with electrosurgical processes, stitches and other surgical stimuli, by way of associating the changes in EEG signal with graded or spontaneous changes in EMG, indicative of pain responses.

ACRONYMS, ABBREVIATION And NOMENCLATURE SUBSTITUTE

| | |
|---|---|
| OAA/S | Observers Assessment of Attention/Sedation |
| PTSD | post-traumatic stress disorder |
| NMDA | N-Methyl-D-aspartate |
| UEM | universal electronic module |
| WEM | wireless electronic module |
| CEM | cable-interfaced electronic module |
| PNS | peripheral nervous system |
| ICU | intensive care unit |
| PVDF | Polyvinyldene fluoride |
| DC | direct current |
| i | index |

AEP indecies:
15 AEP analysis transforms (unshaded cells) generated by applying the 5 secondary transforms (per LHS column dark shaded cells) to the 3 primary transforms corresponding to AEP waveform amplitude (A), differentiated amplitude (DA), and integrated amplitude (DIA), respectively (AEPA; AEPDA and AEPIA per light shaded cells). AEPA; AEPDA and AEPIA are waveform versus the single index (i) representations, as summarised here:

| SECONDARY AEP TRANSFORMS | PRIMARY AEP TRANSFORMS | | |
|---|---|---|---|
| | $AEP_A$ | $AEP_{DA}$ | $AEP_{IA}$ |
| Sum of absolute AEPA values (AS) | $AEPI_{AS}$ | $AEPI_{DAS}$ | $AEPI_{IAS}$ |
| Sum of square root of AEPA values (ASQ) | $AEPI_{ASQ}$ | $AEPI_{DASQ}$ | $AEPI_{IASQ}$ |
| Sum of power of 2 of AEPA values (ASP) | $AEPI_{ASP}$ | $AEPI_{DASP}$ | $AEPI_{IASP}$ |
| Entropy1 AEP values | $\text{Entropy1AEPI}_A$ | $\text{Entropy1AEPI}_{DA}$ | $\text{Entropy1AEPI}_{IA}$ |
| Entropy2 AEP values | $\text{Entropy2AEPI}_A$ | $\text{Entropy2AEPI}_{DA}$ | $\text{Entropy2AEPI}_{IA}$ |

What is claimed is:

1. A biological signal monitoring apparatus for providing biological, neurological, physiological or cognitive state of a subject, comprising:

one or more sensors configured to detect an input signal channel containing a noise signal and a biological input signal evoked in response to a stimulus, the one or more sensor attached to skin of the subject;

a circuitry including a processor executing a computer program including instructions, which when executed by the processor, cause the processor to:

automatically control a width of an aperture window of the biological input signal to determine noise characteristic of the noise signal;

in response to a determination that the noise signal has the noise characteristic based on the controlled aperture window, extract the noise signal from the input signal channel and remove noise;

adjust a phase and an amplitude of the extracted noise signal based on the noise characteristic by removing residual noise to generate an adjusted noise signal;

combine the adjusted noise signal with the biological input signal to generate a combined biological signal;

track the residual noise from the combined biological signal to continuously cancel a subsequent noise signal detected in the input signal channel based on the residual noise;

non-linear dynamic transform the combined biological signal to generate a marker of the biological, neurological, physiological or cognitive state of the subject, wherein the processor is configured to delineate between non-linear dynamic transformed biological signal that are implicated in depth of hypnosis or depth of unconsciousness and the combined biological signal that are reflective of: wake-state, consciousness-state, or states associated with wake-state or consciousness-state and generate the marker based on the delineation; and generate signal quality indicators indicating quality of the combined biological signal after cancelling and adjusting the noise signal and a graphical representation of the marker; and in response to the cancelling and adjusting the noise signal, one or more first light emitting diodes electrically connected to the circuitry and configured to emit visible light representing the quality of the combined biological signal as assessment of the input signal channel; and a display configured to display the graphical representation and the signal quality indicators for a user feedback, wherein the biological signal monitoring apparatus includes: one or more second light emitting diodes configured to indicate a contact status between the one or more sensors and the subject's skin.

2. The biological signal monitoring apparatus of claim 1, wherein the display is configured to display a contact status indicator indicating the contact status of each sensor for the user feedback.

3. The biological signal monitoring apparatus of claim 1, wherein the instructions further cause the processor to: before the determination that the noise signal has the noise characteristic: determine a plurality of points of the input signal channel at which noise is the highest; sample and hold the plurality of points of the input signal channel to generate a timing reference signal; and synchronize the timing reference signal with the biological input signal to generate a synchronized signal.

4. The biological signal monitoring apparatus of claim 3, wherein the synchronized signal is generated by interleaving the biological input signal with the input signal channel at one or more portions between the plurality of points of the input signal channel at which noise is the highest.

5. The biological signal monitoring apparatus of claim 1, wherein the instructions further cause the processor to: based on the adjusted combined biological signal:
   in response to a determination that another noise signal has another noise characteristic, extract the another noise signal from the input signal channel;
   adjust the another noise signal extracted based on the another noise characteristic to generate another adjusted noise signal based on the residual noise;
   combine the another adjusted noise signal with the biological input signal to generate another combined biological signal; and
   track another residual noise from in the another combined biological signal.

6. The biological signal monitoring apparatus of claim 5, wherein the instructions further cause the processor to minimize the noise frequency of the biological input signal.

7. The biological signal monitoring apparatus of claim 5, wherein the instructions further cause the processor to maximize predetermined raw portions of the biological input signal.

8. The biological signal monitoring apparatus of claim 7, wherein the predetermined raw portions of the biological input signal are predetermined by a user of the biological signal monitoring apparatus.

9. The biological signal monitoring apparatus of claim 1, wherein the combined biological signal is non-linear dynamic transformed by quantitative measurement of disorder, an ability to predict future data based on previous data characteristics, a spectral entropy, a complexity analysis; and at least one of entropy delineating between underlying nonlinear neurological signals associated with deep hypnosis and signals reflecting wake or conscious periods.

10. The biological signal monitoring apparatus of claim 1, wherein the source of the noise signal is predetermined by a user of the biological signal monitoring apparatus.

11. The biological signal monitoring apparatus of claim 1, wherein the noise signal is cyclical.

12. The biological signal monitoring apparatus of claim 1, wherein the input signal channel is a channel at which a cyclical signal is generated.

13. The biological signal monitoring apparatus of claim 1, wherein the biological input signal is cyclical.

14. The biological signal monitoring apparatus of claim 1, wherein the source of the noise signal is one or more signals selected from the group consisting of: magnetic resonance imaging echo; equipment disturbance; mains noise; entropy; waveform morphology; electromyography signal intrusion; electrooculography signal intrusion; human body movement; and human body arousal.

15. The biological signal monitoring apparatus of claim 1, wherein the noise signal is extracted from: the frequency spectrum of the input signal channel; or the amplitude values of the input signal channel.

16. The biological signal monitoring apparatus of claim 1, wherein the noise signal is extracted from a phase-shifted version of the input signal channel.

17. A method of monitoring a biological signal using the biological signal monitoring apparatus of claim 1 for providing biological, neurological, physiological or cognitive state of a subject, comprising:
   detecting an input signal channel containing a noise signal and a biological input signal evoked in response to a stimulus, the one or more sensor attached to skin of the subject;
   automatically controlling a width of an aperture window of the biological input signal to determine noise characteristic of a noise signal;
   in response to a determination that the noise signal has the noise characteristic based on the controlled aperture window, extracting the noise signal from the input signal channel and removing noise;
   adjusting a phase and an amplitude of the extracted noise signal based on the noise characteristic by removing residual noise to generate an adjusted noise signal;
   combining the adjusted noise signal with a biological input signal to generate a combined biological signal;
   tracking the residual noise from the combined biological signal to continuously cancel a subsequent noise signal detected in the input signal channel based on the residual noise;
   non-linear dynamic transforming the combined biological signal to generate a marker of the biological, neurological, physiological or cognitive state of the subject, the non-linear dynamic transforming including: delineating between non-linear dynamic transformed biological signal that are implicated in depth of hypnosis or depth of unconsciousness and the combined biological signal that are reflective of: wake-state, consciousness-state, or states associated with wake-state or consciousness-state and generating the marker based on the delineation;
   generating signal quality indicators indicating quality of the combined biological signal after cancelling and adjusting the noise signal, a contact status indicator indicating a contact status of each sensor for the user feedback and a graphical representation of the marker;
   in response to the cancelling and adjusting the noise signal, controlling one or more first light to emit visible light representing the quality of the combined biological signal as assessment of the input signal channel and controlling one or more second light emitting diodes to indicate a contact status between the one or more sensors and the subject's skin; and
   displaying the graphical representation and the signal quality indicators for a user feedback.

18. A non-transitory computer-readable storage medium storing a computer program including instructions, which when executed by a processor of a biological signal monitoring apparatus for providing biological, neurological, physiological or cognitive state of a subject, cause the processor to:
   determine that an input signal channel detected by one or more sensors contains a noise signal, the one or more sensor attached to skin of the subject;
   automatically control a width of an aperture window of the biological input signal to determine noise characteristic of the noise signal;
   in response to a determination that the noise signal has a noise characteristic based on a controlled aperture window, extract the noise signal from the input signal channel and remove noise;
   adjust a phase and an amplitude of the extracted noise signal based on the noise characteristic by extracting residual noise to generate an adjusted noise signal;
   combine the adjusted noise signal with a biological input signal to generate a combined biological signal;
   track the residual noise from the combined biological signal to continuously cancel a subsequent noise signal in the input signal channel based on the residual noise; and non-linear dynamic transform the combined biological signal to generate a marker of the biological, neurological, physiological or cognitive state of the subject, wherein the processor is configured to delineate between non-linear dynamic transformed biological signal that are implicated in depth of hypnosis or depth of unconsciousness and the combined biological signal that are reflective of: wake-state, consciousness-state, or states associated with wake-state or consciousness-state and generate the marker based on the delineation; and generate signal quality indicators indicating quality of the combined biological signal after cancelling and adjusting the noise signal, a contact status indicator indicating a contact status of each sensor for the user feedback and a graphical representation of the marker so that the graphical representation and the signal quality indicators are displayed for a user feedback, one or more first light emitting diodes emit visible light corresponding to the quality of the combined biological signal, and one or more second light emitting diodes configured to indicate a contact status between the one or more sensors and the subject's skin.

* * * * *